United States Patent [19]

Walser

[11] Patent Number: 4,959,361

[45] Date of Patent: Sep. 25, 1990

[54] TRIAZOLO(4,3-a)(1,4)BENZODIAZEPINES AND THIENO (3,2-F)(1,2,4)TRIAZOLO(4,3-a)(1,4)DIAZEPINE COMPOUNDS WHICH HAVE USEFUL ACTIVITY AS PLATELET ACTIVATING FACTOR (PAF) ANTAGONISTS

[75] Inventor: Armin Walser, West Caldwell, N.J.

[73] Assignee: Hoffmann-La Roche Inc., Nutley, N.J.

[21] Appl. No.: 252,964

[22] Filed: Oct. 3, 1988

Related U.S. Application Data

[63] Continuation-in-part of Ser. No. 227,948, Aug. 3, 1988, abandoned, which is a continuation-in-part of Ser. No. 134,726, Dec. 18, 1987, abandoned.

[51] Int. Cl.$^5$ .................... A61K 31/55; C07D 495/14
[52] U.S. Cl. .................... 514/220; 514/211; 514/215; 514/217; 540/488; 540/521; 540/523; 540/525; 540/560; 540/563; 540/564
[58] Field of Search ............. 540/560, 563, 564, 488, 540/521, 523; 514/220, 211, 215, 217

[56] References Cited

U.S. PATENT DOCUMENTS

| | | | |
|---|---|---|---|
| 3,987,052 | 10/1976 | Hester, Jr. ............ | 260/308 R |
| 4,094,984 | 6/1978 | Weber et al. ............ | 260/308 R |
| 4,155,913 | 5/1979 | Hellerbach et al. ............ | 544/146 |
| 4,231,930 | 11/1980 | Hirai et al. ............ | 540/563 |
| 4,321,930 | 11/1980 | Hirai et al. ............ | 260/308 R |
| 4,621,083 | 11/1986 | Casals-Stenzel et al. ............ | 514/320 |
| 4,622,319 | 11/1986 | Casals-Stenzel et al. ............ | 514/220 |
| 4,623,646 | 11/1986 | Casals-Stenzel et al. ............ | 514/220 |

FOREIGN PATENT DOCUMENTS

| | | | |
|---|---|---|---|
| 67845 | 7/1987 | Australia ............ | 514/220 |
| 0254245A1 | 1/1988 | European Pat. Off. ............ | 514/220 |
| 0268242A1 | 5/1988 | European Pat. Off. ............ | 514/220 |
| 0315698 | 5/1989 | European Pat. Off. ............ | 514/220 |
| 3502392A1 | 7/1986 | Fed. Rep. of Germany ............ | 514/220 |
| 2701752 | 7/1987 | Fed. Rep. of Germany ............ | 514/220 |
| 3701344A | 7/1987 | Fed. Rep. of Germany ............ | 514/220 |
| 3610848A1 | 10/1987 | Fed. Rep. of Germany ............ | 514/220 |
| 3724164 A1 | 1/1988 | Fed. Rep. of Germany ............ | 514/220 |
| 2022718 | 7/1985 | Japan ............ | 514/220 |

OTHER PUBLICATIONS

E. Kornecki et al., Science 226, 1454 (1984).

J. Casals-Stenzel, Naun-Schmiedeberg's Arch. Pharmacol. 335 35-355 (1987).
J. Casals-Stenzel et al., Br. J. Pharmacol, 90, 139 (1987).
T. Tahara et al., Chem. Pharm. Bull. 35 2119 (1987).

Primary Examiner—John M. Ford
Assistant Examiner—Zinna Northington Davis
Attorney, Agent, or Firm—George M. Gould; Bernard S. Leon; William G. Isgro

[57] ABSTRACT

The invention relates to compounds of the formula

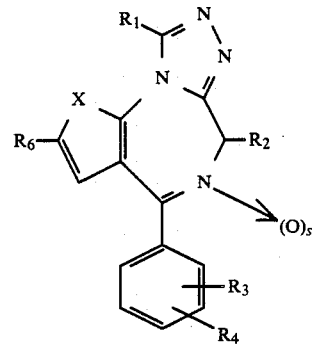

wherein X is —CH=CH— or S;
$R_1$ is lower alkyl, lower alkoxy or trifluoromethyl;
$R_2$ is hydrogen, lower alkyl, lower alkoxy, hydroxy or alkanoyloxy;

$R_3$ and $R_4$, independently, are hydrogen, chlorine, fluorine, lower alkyl or lower alkoxy;

s is an integer from 0 to 1, provided that when s is 1, $R_2$ cannot be hydroxy, lower alkoxy or alkanoyloxy;

$R_5$ is a radical of the formula $R_6$—$(CH_2)_n$— or $R_7$—O—$(CH_2)_m$— wherein $R_6$ and $R_7$ are aryl or a heterocyclic radical, n is an integer of from 0 to 2 and m is an integer of from 1 to 2, provided that, when n is 0, $R_6$ must be attached through a carbon to carbon bond, and provided that $R_7$ is always attached through a carbon to oxygen bond, and, when at least one asymmetric carbon is present, its enantiomers and racemates, and pharmaceutically acceptable acid addition salts thereof.

64 Claims, No Drawings

TRIAZOLO(4,3-a)(1,4)BENZODIAZEPINES AND THIENO (3,2-F)(1,2,4)TRIAZOLO(4,3-a)(1,4)DIAZEPINE COMPOUNDS WHICH HAVE USEFUL ACTIVITY AS PLATELET ACTIVATING FACTOR (PAF) ANTAGONISTS

CROSS-REFERENCE TO RELATED APPLICATION

This application is a continuation-in-part of U.S. application Ser. No. 227,948, filed Aug. 3, 1988 now abandoned, which in turn is a continuation-in-part of U.S. application Ser. No. 134,726, filed Dec. 18, 1987 now abandoned.

BRIEF SUMMARY OF THE INVENTION

The invention relates to compounds of the formula

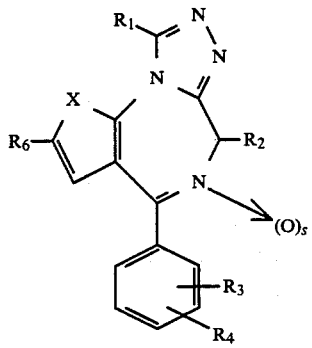

wherein X is —CH=CH— or S;
$R_1$ is lower alkyl, lower alkoxy or trifluoromethyl;
$R_2$ is hydrogen, lower alkyl, lower alkoxy, hydroxy or alkanoyloxy;
$R_3$ and $R_4$, independently, are hydrogen, chlorine, fluorine, lower alkyl or lower alkoxy;
s is an integer from 0 to 1, provided that when s is 1, $R_2$ cannot be hydroxy, lower alkoxy or alkanoyloxy;
$R_5$ is a radical of the formula $R_6$—$(CH_2)_n$ or $R_7$—O—$(CH_2)_m$
wherein $R_6$ and $R_7$ are aryl or a heterocyclic radical, n is an integer of from 0 to 2 and m is an integer of from 1 to 2, provided that, when n is O, $R_6$ must be attached through a carbon to carbon bond, and provided that R is always attached through a carbon to oxygen bond, and, when at least one asymmetric carbon is present, its enantiomers and racemates, and pharmaceutically acceptable acid addition salts thereof.

The compounds of formula I exhibit activity as platelet activating factor (PAF) antagonists and are, therefore, useful in disease states characterized by excess platelet activating factor or for the prevention and treatment of cardiovascular diseases, pulmonary diseases, immunological disorders, inflammatory diseases, dermatological disorders, shock or transplant rejection.

DETAILED DESCRIPTION OF THE INVENTION

As used herein, the term "lower alkyl", denotes a straight or branched chain saturated hydrocarbon containing 1 to 7 carbon atoms, preferably from 1 to 4 carbon atoms, for example, methyl, ethyl, propyl, isopropyl, butyl. t-butyl, neopentyl, pentyl, heptyl, and the like. The term "lower alkoxy" denotes an alkyl ether group in which the alkyl group is as described above, for example, methoxy. ethoxy, propoxy, pentoxy and the like.

The term "aryl" preferably denotes naphthyl, phenyl or phenyl or naphthyl mono-, di- or trisubstituted by chlorine, fluorine. lower alkyl or lower alkoxy.

The term "heterocyclic radical" denotes a monocyclic 5-, 6- or 7-membered heterocyclic or a bi- or tricyclic heterocyclic radical containing one or more hetero atoms, selected from nitrogen, oxygen and sulfur, which radical may optionally be substituted by one or two lower alkyl, lower alkoxy groups, chlorines or fluorines. It is understood that heterocyclic refers to a carbocyclic moiety in which one or more of the carbons are replaced, independently, by oxygen, nitrogen or sulfur.

Exemplary of 5- or 6- membered aromatic heteromonocyclic radicals are pyridinyl, imidazolinyl, thienyl, 2-chlorothienyl, furyl, pyrimidinyl, oxazolinyl or the like.

Exemplary of 5-, 6- or 7-membered non-aromatic hetero monocyclic radicals are

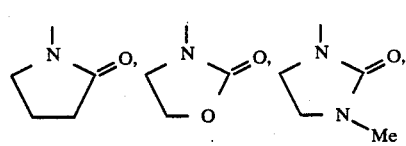

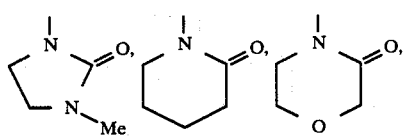

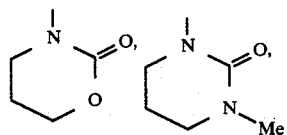

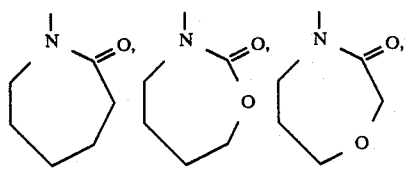

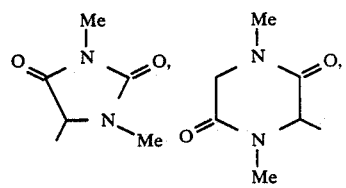

and the like;
Exemplary of hetero-bicyclic radicals are:

(a) 5,5-ringsystem-
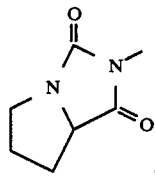
and the like;
(b) 6,5-ringsystem-
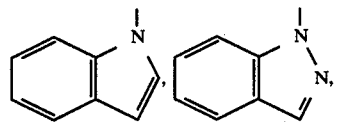
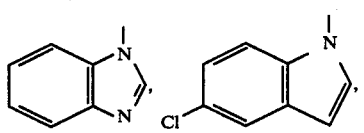
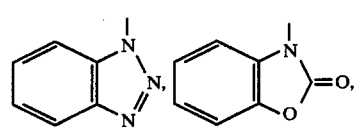
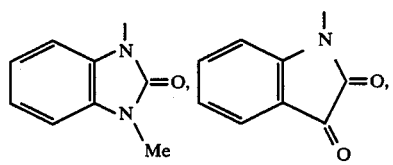
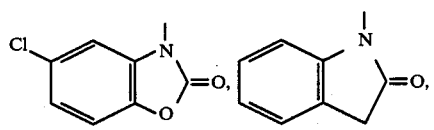
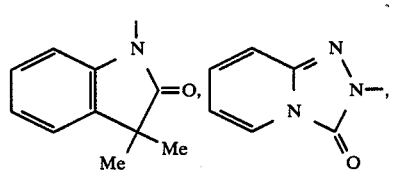
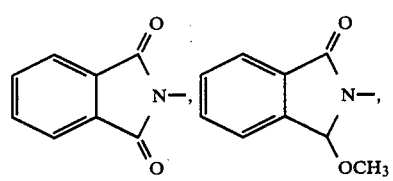
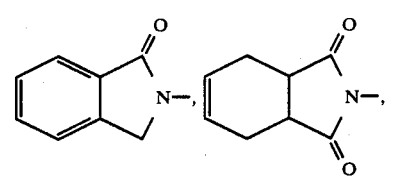
-continued
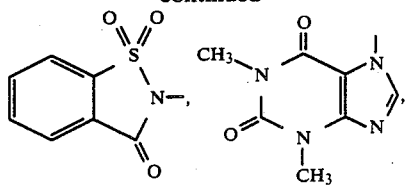
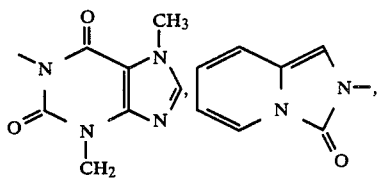
and the like;
(c) 6,6 ringsystem-
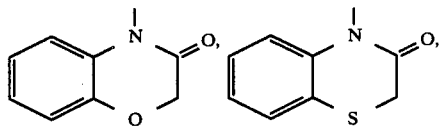
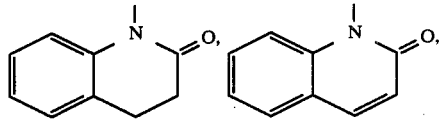
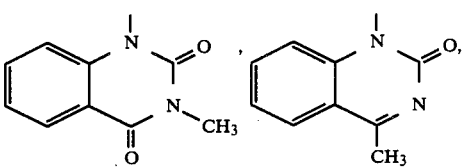
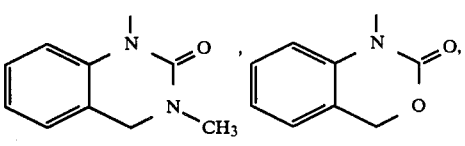
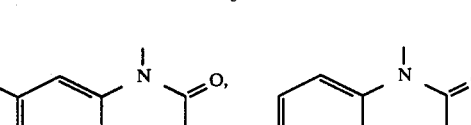
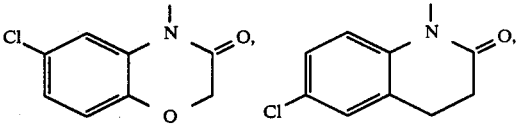
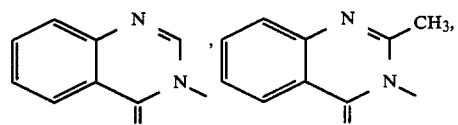
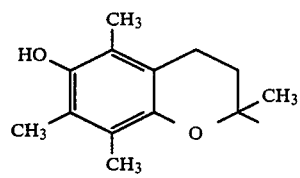
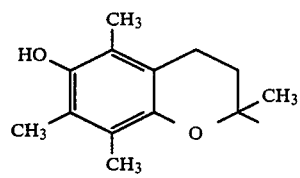
and the like; and -continued
(d) 6,7-ringsystem-
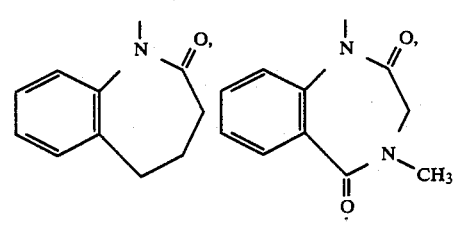
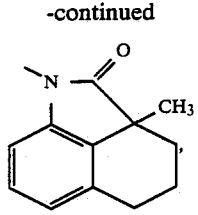
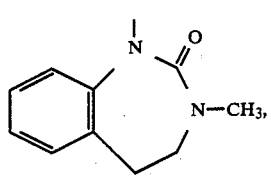
and the like.
Exemplary of hetero-tricyclic radicals are:
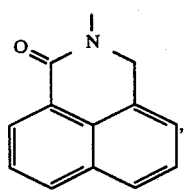
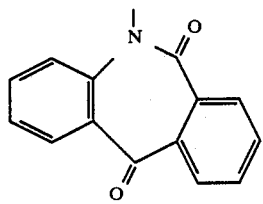
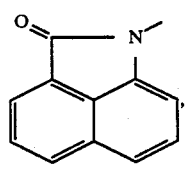
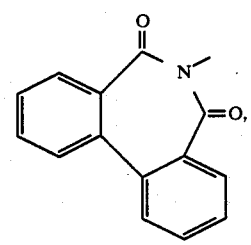
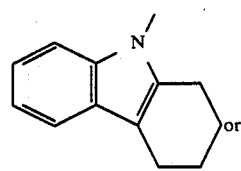
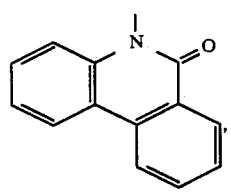
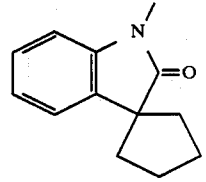 or
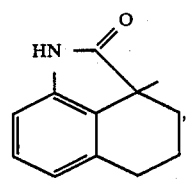
and the like.
As used herein, and as is evident from the nomenclature and structures utilized throughout the specification, the structural representation —≡ is —C≡CH and —≡— is —C≡C—.
The invention relates to compounds of the formula

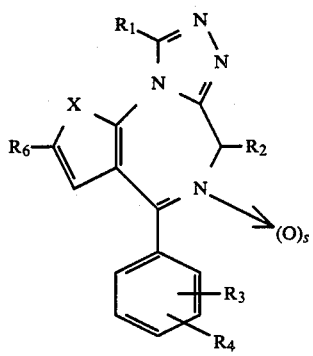

$$R_6-(CH_2)_n\equiv \text{ or } R_7-O-(CH_2)_m\equiv$$

wherein X is —CH=CH— or S;
R₁ is lower alkyl, lower alkoxy or trifluoromethyl;
R₂ is hydrogen, lower alkyl, lower alkoxy, hydroxy or alkanoyloxy;
R₃ and R₄, independently, are hydrogen, chlorine, fluorine, lower alkyl or lower alkoxy;
s is an integer from 0 to 1, provided that when s is 1, R₂ cannot be hydroxy, lower alkoxy or alkanoyloxy;
R₅ is a radical of the formula

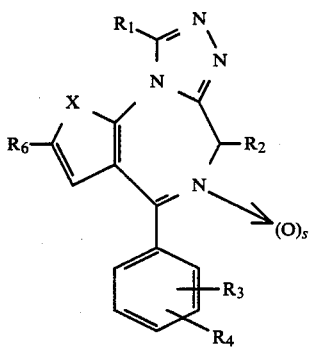

I wherein R₆ and R₇ are aryl or a heterocyclic radical, n is an integer of from 0 to 2 and m is an integer of from 1 to 2, provided that, when n is 0, R₆ must be attached through a carbon to carbon bond, and
R₇ is always attached through a carbon to oxygen bond, and, when at least one asymmetric carbon is present its enantiomers and racemates. and pharmaceutically acceptable acid addition salts thereof.

A preferred group of compounds of formula I are those wherein R₁ is methyl or ethyl; R₂ is hydrogne; R₃ is fluorine or chlorine, R₄ is hydrogen, s is 0 and X and R₅ are as previously described except that n is 1 or 2.

A more preferred group of compounds of formula I are those wherein R₁ is methyl, R₂ is hydrogen, R₃ is fluorine or chlorine at the 2- position of the phenyl moiety, R₄ is hydrogen, s is 0, R₅ is $$R_6-(CH_2)_n\equiv \text{ or } R_7-O-(CH_2)_m\equiv$$

wherein m and n is 1, R₆ is hetero-bicyclic or hetero-tricyclic and R₇ is aryl.

A most preferred group of compounds of formula I are those wherein X is S, R₁ is methyl, R₂ is hydrogen, R₃ is chlorine, s is 0 and at the 2-position of the phenyl moiety, R₄ is hydrogen and R₅ is $$R_6-(CH_2)_n\equiv$$

and n is 1 and R₆ is

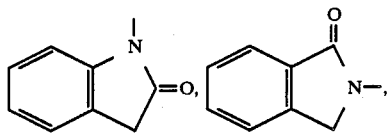

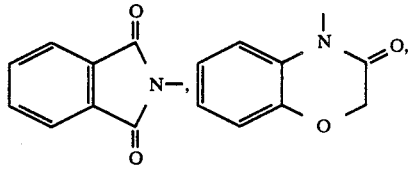

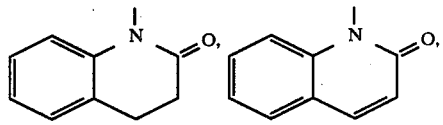

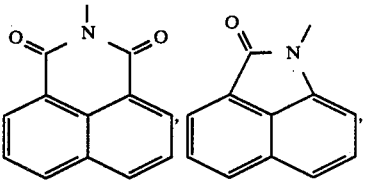

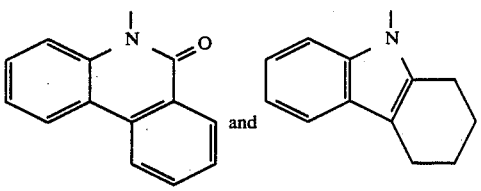 and 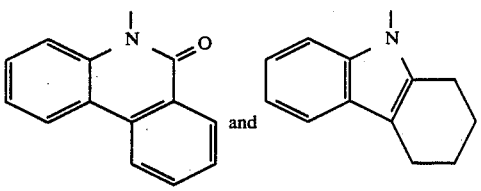

Most preferred compounds of the invention are:
5-{3-[4-(2-chlorphenyl)-9-methyl-6H-thieno-[3,2f][1,2,4]triazolo[4,3-a][1,4]diazepin-2yl]-2-propynyl}phenanthridin-6(5H)-one;
4-(2-chlorophenyl)-2-[3-(1,2,3,4-tetrahydro-9H-carbazol-9-yl)-1-propynyl]-9-methyl-6H-thieno[3,2-f][1,2,4]triazolo[4,3-a][1,4]diazepine;
1-{3-[4-(2-chlorophenyl)-9-methyl-6H-thieno[3,2-f][1,2,4]triazolo[-4,3-a][1,4]diazepin-2-yl]-2-propynyl}-3,4-dihydro-2(1H)-quinolo
2-[3-[4-(2-Chlorophenyl)-9-methyl-6H-thieno[3,2-f][1,2,4]triazolo [-4,3-a][1,4]diazepin-2-yl ]-2-propynyl]-1H-benz[de]-isoquinoline-1,3(2H)-dione;
1-[3-[4-(2-Chlorophenyl)-9-methyl-6H-thieno[3,2-f][1,2,4]triazolo [-4,3-a][1,4]diazepin-2-yl]-2-propynyl]-benz[cd ]-indol-2(1H)-one; and
4-[3-[4-(2-Chlorophenyl)-9-methyl-6H-thieno[3,2-f][1,2,4]triazolo [-4,3-a][1,4]diazepin-2-yl]-2-propynyl]-2H-1,4-benzoxazin-3(4H)-one.

Other preferred compounds of the invention are:
1-[3-[4-(2-Chlorophenyl)-9-methyl-6H-thieno[3,2-f][1,2,4]triazolo [-4,3-a][1,4]diazepin-2-yl]-2-propynyl]-1H-indole2,3-dione;

1-[3-[4-(2-Chlorophenyl)-9-methyl-6H-thieno[3,2-f][1,2,4]triazolo [-4,3-a][1,4]diazepin-2-yl]-2-propynyl]-1,3-dihydro2H-indol-2-one;

2-[3-[4-(2-Chlorophenyl)-9-methyl-6H-thieno[3,2-f][1,2,4]triazolo [4,3-a][1,4]diazepin-2-yl]-2-propynyl]-1,2,4-triazolo[4,3-a]pyridin-3(2H)-one;

2-[3-[4-(2-Chlorophenyl)-9-methyl-6H-thieno[3,2-f][1,2,4]triazolo ]4,3-a][1,4]diazepin-2-yl]-2-propynyl]-1,2-benzisothiazol-3(2H)-one 1,1dioxide;

4-(2-Chlorophenyl)-2-[3-(1H-indazol-1-yl)-1-propynyl]-9-methyl-6H-thieno[3,2-f][1,2,4]triazolo[4,3-a][1,4]diazepine;

2-[3-(1H-Benzimidazol-1-yl)-1-propynyl]-4-(2-chlorophenyl)-9-methyl-6H-thieno[3,2-f][1,2,4]triazolo[4,3-a][1,4]diazepine;

2-[3-[6-(2-Fluorophenyl)-1-methyl-4H-[1,2,4]triazolo[4,3-a][1,4]benzo-diazepin-8-yl]-2-propynyl]-1H-isoindole1,3(2H)-dione; and 4-[3-[6-(2-Fluorophenyl)-1-methyl-4H-[1,2,4]triazolo[4,3-a][1,4]benzodiazepin-8-yl]-2-propynyl]-2H-1,4-benzoxazin3(4H)-one.

Exemplary compounds of formula I of the invention are:

2-[3-(1H-Benztriazol-1-yl)-1-propynyl]-4-(2-chlorophenyl)9-methyl-6H-thieno[3,2-f][1,2,4]triazolo[4,3-a][1,4]diazepine;

4-[3-[6-(2-Fluorophenyl)-1-methyl-4H-[1,2,4]triazolo[4.3-a][-1,4]benzodiazepin-8-yl]-2-propynyl]-2H-1,4-benzo-thiazin-3(4H)-one;

2-[3-[(1-Ethyl-6-(2-fluorophenyl)-4H-[1,2,4]triazolo[4,3-a][-1,4]benzodiazepin-8-yl]-2-propynyl]-1H-isoindole1,3(2H)-dione;

2-[3-[6-(2-Chlorophenyl)-1-methyl-4H-[1,2,4]triazolo[4,3-a][1,4]benzodiazepin-8-yl]-2-propynyl]-1H-isoindole1,3(2H)-dione;

2-[3-[6-(2-Chlorophenyl)-1-methyl-4H-[1,2,4]triazolo[4,3-a][1,4]benzodiazepin-8-yl]-2-propynyl]-1H-benz[de]isoquinolin-1,3(2H)-dione;

2-[3-[6-(2-Fluorophenyl)-1-methyl-4H-[1,2,4]triazolo[4,3-a][-1,4]benzodiazepin-8-yl]-2-propynyl]-1H-benz[de]isoquinolin-1,3(2H)-dione:

3-[3-[6-(2-Fluorophenyl)-1-methyl-4H-[1,2,4]triazolo[4,3-a][1,4]benzodiazepin-8-yl]-2-propynyl]-4(3H)-quinazolinone;

3-[3-[6-(2-Fluorophenyl)-1-methyl-4H-[1,2,4]triazolo[4,3-a][1,4]benzodiazepin-8-yl]-2-propynyl]-2-methyl-4(3H)quinazolinone;

2-[3-[6-(2-Fluorophenyl)-1-methyl-4H-[1,2,4]triazolo[4,3-a][1,4]benzodiazepin-8-yl]-2-propynyl]-2,3-dihydro 1H-isoindol-1-one;

rac-2-[3-[6-(2-Fluorophenyl)-1-methyl-4H-[1,2,4]triazolo[4,3-a][-1,4]benzodiazepin-8-yl]-2-propynyl]-2,3-dihydro-3-methoxy-1H-isoindol-1-one;

2-[3-[6-(2-Fluorophenyl)-1-methyl-4H-[1,2,4]triazolo[4,3-a][1,4]benzodiazepin-8-yl]-2-propynyl]-1,2,4-triazolo[4,3-a]pyridin-3(2H)-one;

2-[3-[6-(2-Fluorophenyl)-1-methyl-4H-[1,2,4]triazolo[4,3-a][1,4]benzodiazepin-8-yl]-2-propynyl]-1,2-benzisothiazol-3(2H)-one 1,1-dioxide;

2-[3-[6-(2-Fluorophenyl)-1-methyl-4H-[1,2,4]triazolo[4,3-a][1,4]benzodiazepin-8-yl]-2-propynyl]tetrahydro-1H-pyrrolo[1,2-c]imidazole-1,3-(2H)-dione;

1-[3-[6-(2-Fluorophenyl)-1-methyl-4H-[1,2,4]triazolo[4,3-a][1,4]benzodiazepin-8-yl]-2-propynyl]-1,3-dihydro-2H-indol-2-one:

2-[3-[6-(2-Fluorophenyl)-1-methyl-4H-[1,2,4]triazolo[4,3-a][1,4]benzodiazepin-8-yl]-2-propynyl]-3a,4,7,7a-tetrahydro-1H-isoindole-1,3(2H)-dione;

1-[3-[6-(2-Fluorophenyl)-1-methyl-4H-[1,2,4]triazolo[4,3-a][1,4]benzodiazepin-8-yl]-2-propynyl]-3,4-dihydro-4-methyl-1H-1,4-benzodiazepine-2,5-dione;

1-[3-[6-(2-Fluorophenyl)-1-methyl-4H-[1,2,4]triazolo[4,3-a][1,4]benzodiazepin-8-yl]-2-propynyl]-3,7-dihydro-3,7-dimethyl-1H-purine-2,6-dione;

2-[4-[6-(2-Fluorophenyl)-1-methyl-4H-[1,2,4]triazolo[4,3-a][1,4]benzodiazepin-8yl]-3-butynyl]-1H-isoindole-1,3(2H)-dione;

8-[3-(1H-Benzimidazol-1-yl)-1-propynyl]-6-(2-chlorophenyl) -1-methyl-4H-[1,2,4]triazolo[4,3-a][1,4]benzodiazepine;

8-[3-(1H-Benzimidazol-1-yl)-1-propynyl]-6-(2-fluorophenyl)-1-methyl-4H-[1,2,4]triazolo[4,3-a][1,4]benzodiazepine;

6-(2-Fluorophenyl)-8-[3-(1H-indol-1-yl)-1-propynyl]-1-methyl-4H-[1,2,4]triazolo[4,3-a][1,4]benzodiazepine;

6-(2-Chlorophenyl)-8-[3-(1H-indol-1-yl)-1-propynyl]-1-methyl-4H-[1,2,4]triazolo[4,3-a][1,4]benzodiazepine;

6-(2-Fluorophenyl)-8-[3-(1H-indazol-1-yl)-1-propynyl]-1-methyl-4H-[1,2,4]triazolo[4,3-a][1,4]benzodiazepine;

3-[3-[6-(2-Fluorophenyl)-1-methyl-4H-[1,2,4]triazolo [4,3-a][1,4]benzodiazepin-8-yl]-2-propynyl]-2,3-dihydro-1,3benzoxazol-2-one;

3-[3-[6-(2-Chlorophenyl)-1-methyl-4H-[1,2,4]triazolo[4,3-a][1,4]benzodiazepin-8-yl]-2-propynyl]-2,3-dihydro-1,3-benzoxazol-2-one;

1-[3-[6-(2-Fluorophenyl)-1-methyl-4H-[1,2,4]triazolo[4,3-a][1,4]benzodiazepin-8-yl]-1,3-dihydro-3-methyl-benzimidazol-2(2H)-one;

3-[3-[4-(2-Chlorophenyl)-9-methyl-6H-thieno[3,2-f][1,2,4]triazolo[4,3-a][1,4]diazepin-2-yl]-2-propynyl]-2,3-dihydro-1,3-benzoxazol-2-one;

1-[3-[4-(2-Chlorophenyl)-9-methyl-6H-thieno[3,2-f][1,2,4]triazolo[4,3-a][1,4]diazepin-2-yl]-2-propynyl]-1,3-dihydro-3-methyl-benzimidazol-2(2H)-one;

4-[3-[4-(2-Chlorophenyl)-9-methyl-6H-thieno[3,2-f][1,2,4]triazolo[4,3-a][1,4]diazepin-2-yl]-2-propynyl]-2H-1,4-benzothiazin-3(4H)-one;

2-[3-[4-(2-Chlorophenyl)-9-methyl-6H-thieno[3,2-f][1,2,4]triazolo[4,3-a][1,4]diazepin-2-yl]-2-propynyl]-1H-isoindol1,3(2H)-dione;

3-[3-[4-(2-Chlorophenyl)-9-methyl-6H-thieno[3,2-f][1,2,4]triazolo[4,3-a][1,4]diazepin-2-yl]-4(3H)-quinazolinone;

3-[3-[4-(2-Chlorophenyl)-9-methyl-6H-thieno[3,2-f][1,2,4]triazolo[4,3-a][1,4]diazepin-2-yl]-2-propynyl]-1,3-dihydro-1-methylquinazolin-2,4-dione;

1-[3-[4-(2-Chlorophenyl)-9-methyl-6H-thieno[3,2-f][1,2,4]triazolo[4,3-a][1,4]diazepin-2-yl]-2-propynyl]-1,3-dihydro-3-methylquinazolin-2,4(2H,4H)-dione;

2-[3-[4-(2-Chlorophenyl)-9-methyl-6H-thieno[3,2-f][1,2,4]triazolo[4,3-a][1,4]diazepin-2-yl]-2-propynyl]-2,3-dihydro-1H-isoindol-1-one;

2-[3-[4-(2-Chlorophenyl)-9-methyl-6H-thieno[3,2-f][1,2,4]triazolo[4,3-a][1,4]diazepin-2-yl]-2-propynyl]-tetrahydro-1H-pyrrolo[1,2-c]imidazole-1,3(2H)-dione;

2-[3-[4-(2-Chlorophenyl)-9-methyl-6H-thieno[3,2-f][1,2,4]triazolo[4,3-a][1,4]diazepin-2-yl]-2-propynyl]-3a,4,7,7a- tetrahydro-1H-isoindole-1,3(2H)-dione;

1-[3-[4-(2-Chlorophenyl)-9-methyl-6H-thieno[3,2-f][1,2,4]triazolo[4,3-a][1,4]diazepin-2-yl]-2-propynyl]-3,4-dihydro-4-methyl-1H-1,4-benzodiazepine-2,5-dione;

2-[4-[4-(2-Chlorophenyl)-9-methyl-6H-thieno[3,2-f][1,2,4]triazolo[4,3-a][1,4]diazepin-2-yl]-3-butynyl]-1H-isoindole1,3(2H)-dione;

1-[3-[4-(2-Chlorophenyl)-9-methyl-6H-thieno[3,2-f][1,2,4]triazolo[4,3-a][1,4]diazepin-2-yl]-2-propynyl]-2(1H)-quinolinone;

1-[3-[4-(2-Chlorophenyl)-9-methyl-6H-thieno[3,2-f][1,2,4]triazolo[4,3-a][1,4]diazepin-2-yl]-2-propynyl]-3,4-dihydro-2(1H)-quinolinone;

1-[3-[4-(2-Chlorophenyl)-9-methyl-6H-thieno[3,2-f][1,2,4]triazolo[4,3-a][1,4]diazepin-2-yl]-2-propynyl]-4-methyl-2(1H)-quinazolinone;

1-[3-[4-(2-Chlorophenyl)-9-methyl-6H-thieno[3,2-f][1,2,4]triazolo[4,3-a][1,4]diazepin-2-yl]-2-propynyl]-1,4-dihydro-2H-3,1-benzoxazin-2-one;

1-[3-[4-(2-Chlorophenyl)-9-methyl-6H-thieno[3,2-f][1,2,4]triazolo[4,3-a][1,4]diazepin-2-yl]-2-propynyl]-3,4-dihydro-3-methyl-2(1H)-quinazolinone;

1-[3-[4-(2-Chlorophenyl)-9-methyl-6H-thieno[3,2-f][1,2,4]triazolo[4,3-a][1,4]diazepin-2-yl]-2-propynyl]-3,7-dihydro-3,7-dimethyl-1H-purin-2,6-dione;

7-[3-[4-(2-Chlorophenyl)-9-methyl-6H-thieno[3,2-f][1,2,4]triazolo[4,3-a][1,4]diazepin-2-yl]-2-propynyl]-1,3-dihydro-1,3-dimethyl-1H-purine-2,6-dione;

5-[3-[4-(2-Chlorophenyl)-9-methyl-6H-thieno[3,2-f][1,2,4]triazolo[4,3-a][1,4]diazepin-2-yl]-2-propynyl]-dibenz[b,e]-azepine-6,H (5H)-dione;

2-[3-(9H-Carbazol-9-yl)-1-propynyl]-4-(2-chlorophenyl)-9-methyl-6H-thieno[3,2-f][1,2,4]triazolo[4,3-a][1,4]diazepine;

6-(2-Chlorophenyl)-1-methyl-8-(3-phenoxy-1-propynyl)-4H-[1,2,4]triazolo[4,3-a][1,4]benzodiazepine;

6-(2-Chlorophenyl)-1-methyl-8-[3-(1-naphthyloxy)-1-propynyl]-4H-[1,2,4]triazolo[4,3-a][1,4]benzodiazepine;

6-(2-Chlorophenyl)-1-methyl-8-[3-(3-pyridinyloxy-)-1propynyl]-4H-[1,2,4]triazolo[4,3-a][1,4]benzodiazepine;

6-(2-Fluorophenyl)-1-methyl-8-[3-(2-pyrimidyloxy)-1-propynyl]-4H-[1,2,4]triazolo[4,3-a][1,4]benzodiazepine;

4-(2-Chlorophenyl)-9-methyl-2-(3-phenoxy-1-propynyl)-6H-thieno[3,2-f][1,2,4]triazolo[4,3-a][1,4]diazepine;

4-(2-Chlorophenyl)-9-methyl-2-[3-(3-pyridyloxy-1-propynyl]-6H-thieno[3,2-f][1,2,4]triazolo[4,3-a][1,4]diazepine;

4-(2-Chlorophenyl)-9-methyl-2-[3-(2-pyrimidyloxy)-1-propynyl]-6H-thieno[3,2-f][1,2,4]triazolo[4,3-a][1,4]diazepine;

6-(2-Fluorophenyl)-1-methyl-8-[3-(8-quinolinyloxy)-1-propynyl]-4H-[1,2,4]triazolo[4,3-a][1,4]benzodiazepine;

6-(2-Chlorophenyl)-1-methyl-8-(2-thienylethynyl)-4H-triazolo[4,3-a][1,4]benzodiazepine;

6-(2-Fluorophenyl)-1-methyl-8-(5-pyrimidinyl)ethynyl-4H-triazolo[4,3-a][1,4]benzodiazepine;

6-(2-Fluorophenyl)-1-methyl-8-(2-pyridylethynyl)-4H-triazolo[4,3-a][1,4]benzodiazepine; 4-(2-Chlorophenyl)-9-methyl-2-(2-thienylethynyl)-6H-thieno2-f][1,2,4]triazolo[4,3-a][1,4]diazepine; and 4-(2-Chlorophenyl)-9-methyl-2-(1-naphthylethynyl)-6H-thieno[3,2-f][1,2,4]triazolo[4,3-a][1,4]diazepine.

The compounds of formula I can be prepared as hereinafter described in Reaction Schemes I and II.

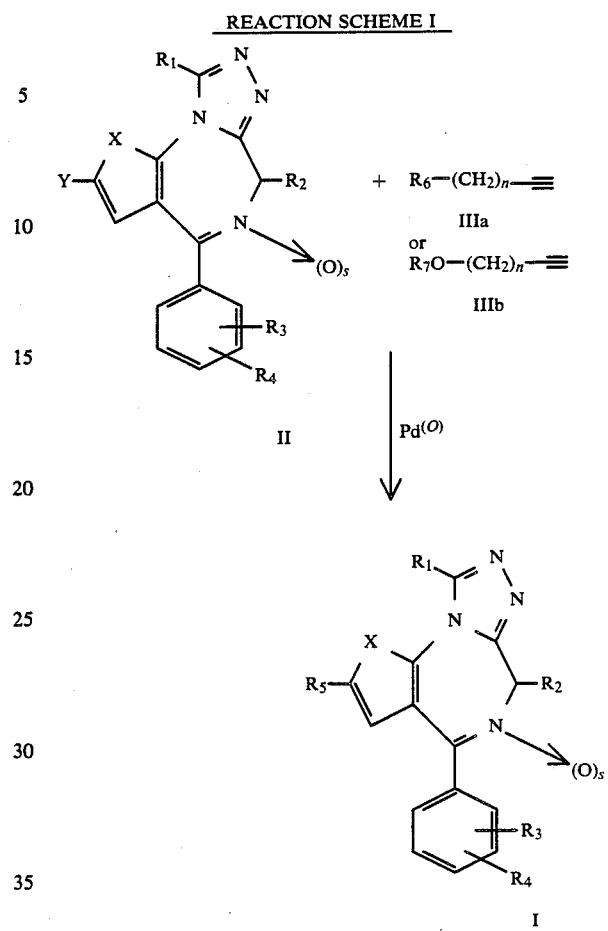

REACTION SCHEME I wherein $R_1$, $R_2$, $R_3$, $R_4$, $R_5$, $R_6$, $R_7$, X and s are as previously described, and Y is bromo or iodo.

In Reaction Scheme I, a triazolothieno- or a triazolobenzodiazepine of formula II, wherein Y is bromo or iodo, is reacted with a terminal acetylene of formula IIIa or IIIb utilizing transition metal catalysis according to procedures known in the art, to yield the corresponding compound of formula I.

The reaction of a bromo or preferably an iodo compound of structure II with an acetylene of formula IIIa or IIIb is carried out in an inert solvent, preferred solvents are acetonitrile, tetrahydrofuran and dimethylformamide, at a temperature in the range of from room temperature to about 100° C., depending on the nature of Y and X in formula II, in the presence of a palladium catalyst, for example bis(triphenylphosphine)palladium dichloride or diacetate, optionally in the presence of a catalytical amount of cuprous iodide and an excess of a proton acceptor, such as, triethylamine. Alternatively, a compound of formula I, wherein s is 0 and $R_5$ is other than a moiety containing a basic nitrogen atom, can be converted, if desired, to the corresponding N-oxide by treatment with an peroxy acid such as m-chloroperoxybenzoic acid, peroxyacetic acid and the like in an inert solvent such as methylene chloride, chloroform acetic acid and the like, at a temperature in the range of from about 0° to 80°. In addition, a compound of formula I, wherein $R_2$ is alkanoyloxy, can also be prepared by treating the corresponding N-oxide according to known procedures, for example, with an alkanoic acid anhydride such as acetic anhydride, at a temperature in the range of from about 50° to about 100°, optionally in the presence of pyridine. A compound of formula I, wherein $R_2$ is hydroxy, can also be prepared by hydrolysis of a corresponding compound of formula I, wherein $R_2$ is alkanoyloxy.

The resulting product of formula I can be isolated by conventional methods for example, chromatography or crystallization.

The starting materials of formula II are known compounds or can be prepared in analogy to published procedures. This applies also to the acetylene compounds of formulas IIIa and IIIb. The acetylenes of formula IIIa, wherein n is 1, are conveniently prepared by alkylation of the corresponding heterocyclic system with propargyl bromide following known methods. The compounds of formula IIIa, wherein n is 2, can be similarly prepared by alkylation of the corresponding heterocyclic ring system, for example, with 4-tosyloxy-1-butyne.

It is noted that when a compound of formula I and/or formula II possess an asymmetric carbon, it may be convenient to utilize an enantiomer in place of the racemic mixture as the starting materials.

REACTION SCHEME II

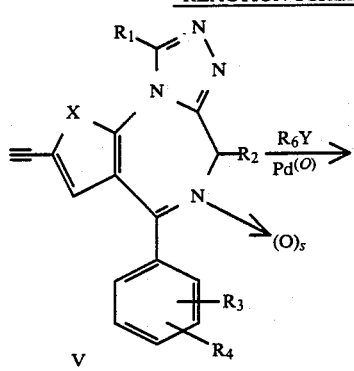

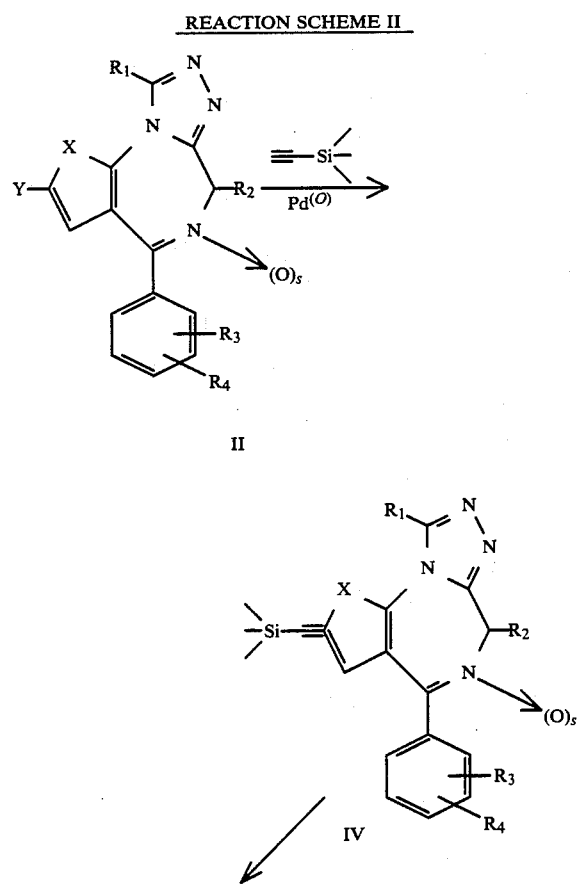

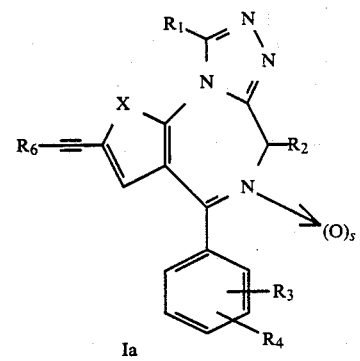

wherein $R_1$, $R_2$, $R_3$, $R_4$, $R_6$, Y and s are as previously described.

In Reaction Scheme II, a compound of formula I, wherein n is zero, can alternately be prepared as set forth. A compound of formula II, wherein Y is bromo or iodo, is coupled by palladium catalysis with trimethylsilylacetylene to yield the corresponding product of formula IV. The reaction parameters are essentially the same as described above for Reaction Scheme I. More particularly, a compound of formula IV is desilylated by treatment with an aqueous alkali solution to yield the corresponding ethynyl compound of formula V. The conversion of a compound of formula IV to a compound of formula V is carried out by hydrolysis, preferably by treatment with an aqueous alkali hydroxide solution in a water miscible solvent, such as, alcohol, tetrahydrofuran, dioxane or the like with the exclusion of oxygen. The temperature at which the reaction is carried out is not critical, but a temperature in the range of from about 0° to 100° C. is preferred. A resulting compound of formula V is subjected to another palladium catalized coupling with an aryl or heteroaryl halide $R_6Y$. wherein Y is either bromo or iodo or and $R_6$ is aryl or a heterocyclic radical.

The resulting compound of formula Ia can be isolated by known procedures, for example, crystallization or chromatography.

The compounds of formula I can form acid addition salts with strong inorganic or organic acids. Thus, they form pharmaceutically acceptable acid addition salts with both pharmaceutically acceptable organic and inorganic acids, for example, with hydrohalic acids, such as, hydrochloric acid hydrobromio acid, hydroiodic acid, other mineral acids, such as, sulfuric acid, phosphoric acid, perchloric acid or the like, alkyl and mono-aryl sulfonic acids such as, ethanesulfonic acid, toluenesulfonic acid, benzenesulfonic acid, or the like. Non-pharmaceutically acceptable acid addition salts of a compound of formula I can be converted into pharmaceutically acceptable acid addition salts via conventional metathetic reactions whereby the non-pharmaceutically acceptable anion is replaced by a pharmaceutically acceptable anion; or alternatively, by neutralizing the non-pharmaceutically acceptable acid addition salt and then reacting the so-obtained free base with a reagent yielding a pharmaceutically acceptable acid addition salt.

The compounds of formula I exhibit activity as platelet activating factor (PAF) antagonists and are, therefore, useful in disease states characterized by excess platelet activating factor or for the prevention and treatment of cardiovascular diseases, pulmonary diseases, immunological disorders inflammatory diseases, dermatological disorders, shock or transplant rejection.

The useful activity of the compounds of formula I can be demonstrated by the following procedures:

Binding Assay (a) Assay

The binding assay was done in 400 λl polyethylene microcentrifuge tubes (Beckman) containing 50 μl of an oil mixture of 2 parts Siliconol AR200 (Serva): 1 part Silicone Fluid (Arthur H. Thoma). Buffer, standards, or analogs (150 μl total volume) were added to the tubes. Radiolabelled H-PAF (50 μl) was then added to the tubes. The reaction was started by the addition of 50 μl of dog platelets ($2\times10^7$ platelets). The tubes were capped, inverted several times to mix, and incubated for 10 minutes at room temperature. The platelets were separated from the incubation mixture by centrifuging 1 minute in a Beckman Microfuge B centrifuge. The tip of the microfuge tube was cut off, and the platelets were washed out of the tip with 200 μl of 50% methanol (Burdick and Jackson). Aquasol (NEN, 10 ml) was added and the radioactivity in the samples was determined using an LS 8100 Beckman liquid scintillation counter linked to a Techtran tape recorder Data was processed through an in-house computer system. Alternatively, radioactivity was determined using a Searle Mark III liquid scintillation counter linked to a Iso-Data microprocessor. Results are set forth in Tables I and II.

(b) preparation of platelets

Blood was collected from anesthesized or unanesthesized dogs into 50 ml plastic centrifuge tubes containing 3.8% sodium citrate as the anticoagulant (1 volume of citrate/9 volumes of blood). The red cells were removed by centrifugation for 15 minutes at 600 rpm (100-125 g) at room temperature. An aliquot of the supernatant platelet rich plasma (PRP) was saved for cell counting and the remainder was acidified to pH 6.5 with 0.15M citric acid. The platelet pellet was obtained after a 10 minute centrifugation at 2000 rpm (1000 g) at room temperature. Washed platelets were prepared by resuspending the platelet pellet once with pBS containing 1 mM EDTA, centrifuging as noted, and then resuspending the platelets in 0.1% BSA pBS. An aliquot of the washed platelets was counted. Platelets used for binding assays were diluted to $2\times10^7$ platelets/assay tube ($4\times10^8$ platelets/ml). platelet countinq was done using a Royco Cell-Crit 921.

PAF Induced Bronchoconstriction Assay

Male animals (Hartlet Strain, 400-500 g were anesthetized with urethane (2 g/kg, i.p.). Each animals' trachea was cannulated and the guinea pigs were respirated using a Harvard small animal rodent respirator (3.0 cc stroke volume, 40 breaths per min.). Tracheal pressure was recorded from a cannula inserted in the trachea and connected to a Statham pressure transducer.

The jugular vein was cannulated for administering compounds. Spontaneous breathing was arrested with succinylcholine (1.2 mg/kg, i.v.) administered 2 minutes prior to intravenous injection of platelet activating factor PAF). Since propranolol has been shown to enhance bronchoconstrictor responses, all animals were pretreated five minutes prior to challenge with propranolol (0.1 mg/kg, i.v.).

For the intravenous testing, the guinea pig is given a 1-minute pretreatment with propranolol at a dose of 0.1 mg/kg intravenously. The test compound is administered with a 1 minute pretreatment prior to intravenous challenge with PAF. The animal is then challenged with a 1 μg/kg intravenous dose of PAF and the change in tracheal pressure is measured.

For the oral testing, the procedure includes a 1-hour pretreatment period with the test compound administered through an oral gavage tube. propranolol or succinylcholine and PAF are administered intravenously, and the change in tracheal pressure measured.

The change in tracheal pressure is determined by subtracting the steady state baseline achieved after administration of succinylcholine from the peak broncho. constriction seen after challenge with PAF. The mean is calculated for each test compound and compared to the mean of the control animals to give the percent inhibition of bronchoconstriction. The standard error is calculated as the standard error of the mean.

The results obtained are set forth in Tables 1 and 2 which follow:

TABLE I
TRIAZOLOTHIENODIAZEPINES

| R | PAF-binding IC-50 (nM) | Bronchoconstriction ID-50, mg/kg | |
|---|---|---|---|
| | | i.v. | p.o. 2 hr |
| naphthalimide-N-propargyl | 12 | <0.1 | 0.025 |
| isatin-N-propargyl | 7 | <0.1 | 0.060 |
| naphtholactam-N-propargyl | 5 | <0.1 | 0.042 |
| —C≡C—Si(CH₃)₃ | 20 | 0.28 | |
| —C≡CH | 10 | 0.02 | (17%)* |
| benzimidazole-N-propargyl | 4.5 | | 0.12 |
| oxindole-N-propargyl | 3.0 | | 0.05 |

TABLE I-continued
TRIAZOLOTHIENODIAZEPINES

| R | PAF-binding IC-50 (nM) | Bronchoconstriction ID-50, mg/kg | |
|---|---|---|---|
| | | i.v. | p.o. 2 hr |
| *N-propargyl-N-sulfonyl benzamide* | 4 | | (27%)* |
| *N-propargyl-triazolopyridinone* | 11 | | (79%)* |
| *N-propargyl-indazole* | 1.0 | 0.002 | 0.015 |
| *N-propargyl-benzoxazinone* | 0.7 | 0.007 | 0.019 |
| *N-propargyl-dimethylxanthine (isomer 1)* | 20 | 0.043 | (27%)* |
| *N-propargyl-methylxanthine* | 7.0 | 0.018 | (38%)* |

TABLE I-continued
TRIAZOLOTHIENODIAZEPINES
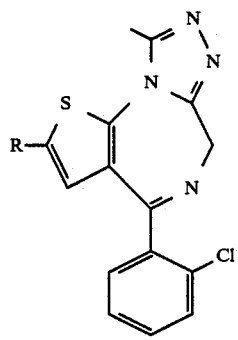
| R | PAF-binding IC-50 (nM) | Bronchoconstriction ID-50, mg/kg | |
|---|---|---|---|
| | | i.v. | p.o. 2 hr |
| ![structure] | 2.0 | 0.006 | 0.016 |
| ![structure] | 0.2 | 0.004 | 0.015 |
| ![structure] | 3.5 | 0.01 | 0.009 |
| ![structure] | 0.3 | 0.004 | 0.043 |
| ![structure] | 0.7 | 0.008 | (24%)* |
| ![structure] | 12 | 0.013 | 0.03 |

TABLE I-continued
TRIAZOLOTHIENODIAZEPINES
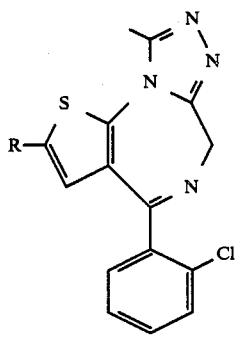
| R | PAF-binding IC-50 (nM) | Bronchoconstriction ID-50, mg/kg | |
|---|---|---|---|
| | | i.v. | p.o. 2 hr |
| (N-propargyl carbazolyl) | 120 | 0.016 | 0.016 |
| (propargyloxy phenyl) | 3.0 | 0.006 | (67%)* |
| (N-propargyl dibenzazepinedione) | 51 | 0.01 | 0.015 |
| (N-propargyl phenanthridinone) | 13 | 0.016 | 0.012 |
| (N-propargyl quinazolinedione) | 0.6 | 0.007 | 0.017 |
| (propargyl chromanol) | 45 | 0.027 | |

TABLE I-continued
TRIAZOLOTHIENODIAZEPINES
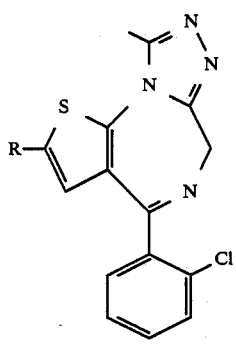
| R | PAF-binding IC-50 (nM) | Bronchoconstriction ID-50, mg/kg | |
|---|---|---|---|
| | | i.v. | p.o. 2 hr |
| (phenylpropargyl) | 100 | >0.1 | |
| 5-oxide (propargyl phenanthridinone) | 15 | 0.017 | |
| 6-hydroxy (propargyl phenanthridinone) | 25 | 0.022 | |
| (propargyl chloro benzoxazinone) | <1 | 0.004 | 0.049 |
| (propargyl benzoxazinone) | 4.0 | 0.007 | 0.076 |
| (propargyl Ph-benzimidazolone) | <1 | 0.008 | 0.015 |

TABLE I-continued

TRIAZOLOTHIENODIAZEPINES

[Structure of triazolothienodiazepine core with R group on thiophene and 2-chlorophenyl substituent]

| R | PAF-binding IC-50 (nM) | Bronchoconstriction ID-50, mg/kg i.v. | Bronchoconstriction ID-50, mg/kg p.o. 2 hr |
|---|---|---|---|
| [N-propargyl naphthalimide] | 10 | | (66%)* |
| [N-propargyl phthalimide-like diketone] | 6 | 0.008 | 0.026 |
| [2-ethynylpyridine] | 250 | 0.056 | (5%)* |
| [N-propargyl isoquinolin-1(2H)-one] | 1.0 | 0.007 | 0.029 |
| [N-propargyl benzoxazinone with F] | 4 | 0.005 | 0.016 |
| [N-propargyl dichloro-dihydroquinolinone] | <1 | 0.006 | 0.021 |

TABLE I-continued
TRIAZOLOTHIENODIAZEPINES

[Structure: triazolothienodiazepine core with R group on thiophene and 2-chlorophenyl substituent]

| R | PAF-binding IC-50 (nM) | Bronchoconstriction ID-50, mg/kg i.v. | Bronchoconstriction ID-50, mg/kg p.o. 2 hr |
|---|---|---|---|
| [3,4-dihydro-1-oxo-2(1H)-isoquinolinyl with N-propargyl] | 5 | 0.008 | 0.016 |
| [1,2,3,4-tetrahydrocarbazolyl with N-propargyl] | 7 | 0.005 | 0.006 |
| [chloro-phenanthridinone with N-propargyl] | | 0.008 | |
| [dibenzazepinone with N-propargyl] | | 0.01 | |

Numbers as percentages indicate % inhibition of bronchoconstriction at a dose of 0.3 mg/kg p.o.

TABLE II
TRIAZOLOBENZODIAZEPINES

| R1 | R2 | X | PAF-binding IC-50 (nM) | Bronchoconstriction ID-50, mg/kg i.v. | Bronchoconstriction ID-50, mg/kg p.o. 2 hr |
|---|---|---|---|---|---|
| N-propargyl phthalimide | Me | Cl | 20 | 0.019 | 1.4 |
| N-propargyl phthalimide | Me | F | 10 | 0.013 | 0.52 |
| N-propargyl phthalimide | Et | F | 100 | 0.054 | 1.5 |
| N-propargyl-3-methoxy-isoindolinone | Me | F | 100 | (99%)* | (100%)* |
| N-propargyl benz[cd]indol-2(1H)-one | Me | F | 20 | (99%)* | (57%)* |
| N-propargyl benzo[de]isoquinoline-1,3-dione | Me | Cl | 15 | | (99%)* |

TABLE II-continued
TRIAZOLOBENZODIAZEPINES
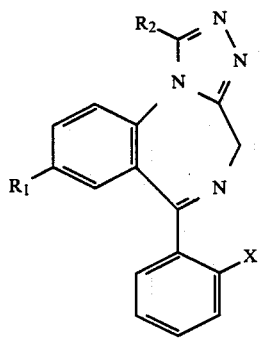
| R1 | R2 | X | PAF-binding IC-50 (nM) | Bronchoconstriction ID-50, mg/kg i.v. | p.o. 2 hr |
|---|---|---|---|---|---|
| 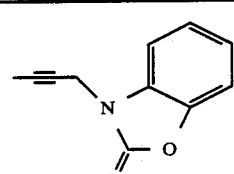 | Me | Cl | 20 | | (91%)* |
| 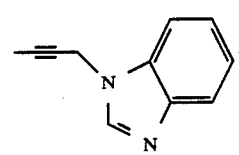 | Me | Cl | 15 | | |
| 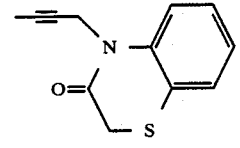 | Me | F | 7 | (99%)* | (99%)* |
| 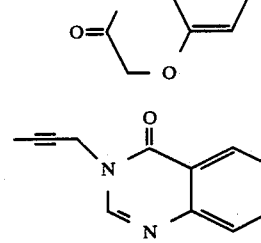 | Me | F | 5 | (100%) | (98%)* |
| 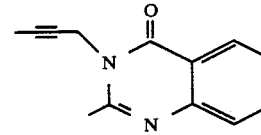 | Me | F | 70 | | |
| 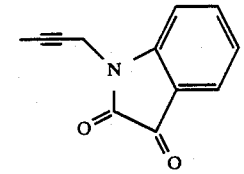 | Me | F | 50 | | |
|  | Me | Cl | 350 | (100%)* | |

TABLE II-continued
TRIAZOLOBENZODIAZEPINES
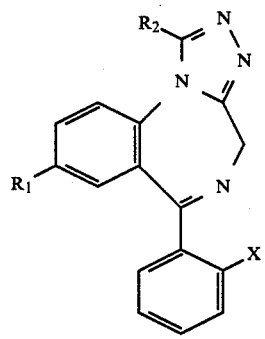
| R1 | R2 | X | PAF-binding IC-50 (nM) | Bronchoconstriction ID-50, mg/kg i.v. | p.o. 2 hr |
|---|---|---|---|---|---|
| (N-propargyl indolinone) | Me | Cl | <10 | | |
| (N-propargyl benzo-fused lactam) | Me | F | 160 | | |
| (propargyloxy pyridine) | Me | Cl | 130 | 0.005 | −3 |
| (N-propargyl pyrrolidinyl hydantoin) | Me | F | 200 | | (99%)* |
| (N-propargyl benzosultam) | Me | F | 150 | | |
| (N-propargyl isoindolinone) | Me | F | 225 | | (100%)* |

TABLE II-continued
TRIAZOLOBENZODIAZEPINES

| R1 | R2 | X | PAF-binding IC-50 (nM) | Bronchoconstriction ID-50, mg/kg i.v. | p.o. 2 hr |
|---|---|---|---|---|---|
| (propargyl-triazolo-pyridinone) | Me | F | 350 | | (43%)* |
| (propargyl-indazole) | Me | F | <10 | | |
| (propargyl-tetrahydrophthalimide) | Me | F | 50 | | (99%)* |
| (propargyloxy-phenyl) | Me | Cl | <10 | | (37%)** |
| (propargyl-oxindole) | Me | F | <10 | | (32%)** |
| (propargyl-indole) | Me | F | | | >>0.3 |
| (propargyl-methylxanthine) | Me | F | | | >>0.3 |

TABLE II-continued
TRIAZOLOBENZODIAZEPINES

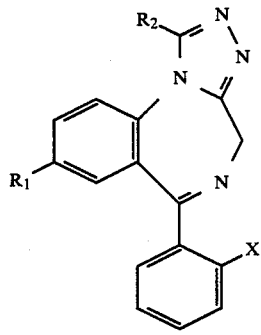

| R1 | R2 | X | PAF-binding IC-50 (nM) | Bronchoconstriction ID-50, mg/kg i.v. | Bronchoconstriction ID-50, mg/kg p.o. 2 hr |
|---|---|---|---|---|---|
| N-(but-2-ynyl)phthalimide | Me | F | | | (54%)** |
| 2-(prop-2-ynyloxy)pyrimidine | Me | F | | | |
| (3-phenylprop-2-ynyl) | Me | F | <1 | 0.006 | >>0.3 |
| 1-(prop-2-ynyl)-3,4-dihydroquinolin-2(1H)-one | Me | F | 20 | 0.015 | 0.44 |
| N-(prop-2-ynyl)phthalimide | CF₃ | F | 5.0 | 0.44 | 0.30 |
| 1-(prop-2-ynyl)-3,4-dihydroquinolin-2(1H)-one, 4-methyl(S) | Me | F | 6.0 | 0.008 | |
| (2,5,7,8-tetramethyl-6-methoxychroman-2-yl)propynyl | Me | F | 70 | 0.03 | |

*Number in percentages indicate % inhibition of bronchoconstriction at 0.1 mg/kg i.v. and 3 mg/kg p.o.
**numbers in percentages indicate % inhibition of bronchoconstriction at an oral dose of 0.3 mg/kg.

**numbers in percentages indicate % inhibition of bronchoconstriction at an oral dose of 0.3 mg/kg.

It is to be understood that formula I as used herein, includes racemates and enantiomers, when one or more asymmetric carbons are present in a compound of formula I.

A compound of formula I, or a salt or a composition containing a therapeutically effective amount of a compound of formula I, an enantiomer or a racemate or a salt thereof can be administered by methods well known in the art. Thus, a compound of formula I, or a salt thereof can be administered either singly or with other pharmaceutical agents, for example, antihistamines, mediator release inhibitors, methyl xanthines, beta agonists or antiasthmatic steroids such as prednisone and prednisolone, orally, parenterally, rectally, or by inhalation, for example in the form of an aerosol, micropulverized powder or nebulized solution. For oral administration they can be administered in the form of tablets, capsules, for example, in admixture with talc, starch, milk sugar or other inert ingredients. that is, pharmaceutically acceptable carriers, or in the form of aqueous solutions, suspensions, elixirs or aqueous alcoholic solutions, for example, in admixture with sugar or other sweetening agents, flavoring agents, colorants, thickeners and other conventional pharmaceutical excipients. For parenteral administration, they can be administered in solutions or suspension, for example, as an aqueous or peanut oil solution or suspension using excipients and carriers conventional for this mode of administration. For parenteral administration, they can be administered in solution or suspension for example as an aqueous or peanut oil solution or suspension using excipients and carriers conventional for this mode of administration. For administration as aerosols, they can be dissolved in a suitable pharmaceutically acceptable solvent, for example, ethyl alcohol or combinations of miscible solvents, and mixed with a pharmaceutically acceptable propellant. Such aerosol compositions are packaged for use in a pressurized container fitted with an aerosol valve suitable for release of the pressurized composition. Preferably, the aerosol valve is a metered valve, that is one which on activation releases a predetermined effective dose of the aerosol composition.

In the practice of the invention, the dose of a compound of formula I or a salt thereof to be administered and the frequency of administration will be dependent on the potency and duration of activity of the particular compound of formula I or salt to be administered and on the route of administration, as well as the severity of the condition, age of the mammal to be treated and the like. Oral doses of a compound of formula I or a salt thereof contemplated for use in practicing the invention are in the range of from about 0.5 to about 1000/mg per day, preferably about 0.5 to about 100 mg per day, preferably about 0.5 to about 10 mg either as a single dose or in divided doses.

Furthermore, since compounds of, formula I of the invention, when $R_2$ is lower alkyl or lower alkoxy, possess an asymmetric carbon atom, they are ordinarily obtained as racemic mixtures. It is to be understood that when $R_6$ and $R_7$ are a heterocyclic group, that group may also have one or more asymmetric carbons, and the resulting racemates enantiomers and diastereomers also form part of this invention. The resolution of such racemates into the optically active isomers can be carried out by known procedures. Some racemic mixtures can be precipitated as eutectics and can thereafter be separated. Chemical resolution is, however, preferred. By this method, diastereomers are formed from the racemic mixture of a compound of formula I, with an optically active resolving agent. The formed diastereomers are separated by selective crystallization or chromatography and converted to the corresponding optical isomer. Thus, the invention covers the racemates of the compounds of formula I as well as their optically active isomers (enantiomers).

The examples which follow further illustrate the invention. All temperatures are in degrees Centigrade, unless otherwise specified.

EXAMPLE 1

2-[3-[6-(2-Fluorophenyl)-1-methyl-4H-[1,2,4]triazolo[4,3-a][1,4-]benzodiazeDin-8-yl]-2-propynyl]-1H-isoindole-1,3(2H)-dione

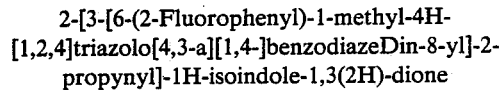

A mixture of 1.68 g (4 mmol) of 6-(2-fluorophenyl)8-iodo-1-methyl-4H-[1,2,4]triazolo[4,3-a][1,4]benzodiazepine, 0.88 g (4.8 mmol) of N-propargylphthalimide, 2 ml of triethylamine, 0.36 g of triphenylphosphine, 0.08 g of cuprous iodide and 40 ml of dimethylformamide was stirred and degassed by a slow stream of arqon for 15 minutes. At this point 0.12 g of palladium acetate was added and the mixture was stirred under argon for 16 hours at room temperature. The reaction mixture was partitioned between 200 ml of methylene chloride and 100 ml of saturated aqueous sodium bicarbonate solution. The organic phase was separated. dried over sodium sulfate and evaporated under reduced pressure, at the end azeotropically with xylene. The crude product was chromatographed over 120 g of silica gel (Merck 70–230 mesh) using 5% (V/V) of ethanol in methylene chloride. The clean fractions of product were combined and evaporated and the residue was crystallized from ethyl acetate to yield 1.6 g (84%) of 2-[3-[6-(2-fluorophenyl)-1-methyl-4H-[1,2,4]triazolo[4,3-a][1,4]-benzodiazepin8-yl]-2-proynyl]-1H-isoindole-1,3(2H)-dione with m.p. 253°–255° C.

The preparation of the starting material is described in Examples 2, 3 and 4.

EXAMPLE 2

1,3-Dihydro-5-(2-fluorophenyl)-7-iodo-1,4-benzodiazepine2(2H)-thione

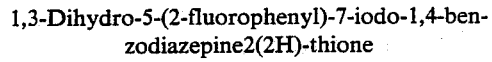

A mixture of 31 g (0.08 mol) of 1,3-dihydro-5-(2-fluoro phenyl)-7-iodo-1,4-benzodiazepin-2(2H)-one [ref. G. F. Field and L. H. Sternbaoh, Swiss patents Nos. 561,706; May 1975; and 562,222; April 1975], 20 g (0.09 mol) of phosphorus pentasulfide, 20 g of sodium bicarbonate and 300 ml of diglyme was stirred and heated to 80°–85° C. for 3 hours. The reaction mixture was then poured onto ice and diluted with water. After stirring for 30 minutes, the solid yellow product was filtered off, washed with water, 2-propanol and little ether. It was sucked dry in the funnel and further dried in vacuum to leave 26 g (80%) of 1,3-dihydro-5-(2-fluorophenyl)-7-iodo-1,4-benzodiazepine-2(2H)-thione which was further transformed as described below. Pure material was obtained by recrystallization from tetrahydrofuran/ethanol and had m.p. 242°–244° C.

EXAMPLE 3

5-(2-Fluorophenyl)-2-hydrazino-7-iodo-3H-1,4-benzodiazepine

Hydrazine, 3 ml, was added to a suspension of 8 g of the above thione in 40 ml of 2-propanol and 100 ml of tetrahydrofuran. After stirring for 15 minutes at room temperature, the reaction mixture was filtered over 20 g of silica gel using tetrahydrofuran for elution. The filtrate was evaporated and the residue was crystallized from ether to yield 6.7 g (83 %) of 5-(2-fluorophenyl)-2-hydrazino-7-iodo 3H-1,4-benzodiazepine with m.p. 179°–181° C.

EXAMPLE 4

6-(2-Fluorophenyl)-8-iodo-1-methyl-4H-[1,2,4]triazolo[4,3-a][1,4]benzodiazepine

A mixture of 4 g of the above hydrazino compound, 20 ml of triethyl orthoacetate, 30 ml of toluene and 4 g of silica gel was heated to reflux with stirring for 3 hours. The silica gel was filtered off and washed with ethanol. The filtrate was evaporated and the residue was crystallized from methylene chloride/ethyl acetate to yield 3.9 g (92%) of 6-(2-fluorophenyl)-8-iodo-1-methyl-4H-[1,2,4]triazolo[4,3-a][1,4]benzodiazepine with m.p. 235°–238° C.

EXAMPLE 5

2-[3-[6-(2-Chlorophenyl)-1-methyl-4H-[1,2,4]triazolo[4,3-a][1,4]benzodiazepin-8-yl]-2-propynyl-]1H-isoindole-1,3(2H)dione semihydrate Reaction of 6-(2-Chlorophenyl)-8-iodo-1-methyl-4H-[1,2,4]triazolo[4,3-a][1,4]benzodiazepine with N-propargylphthalimide as described in example 1 gave the desired 2-[3-[6-(2-chlorophenyl)-1-methyl-4H-[1,2,4]triazolo[4,3 a][1,4]benzodiazepin-8-yl]-2-propynyl]-1H-isoindole-1,3(2H)dione semihydrate, which was purified by chromatography and crystallized from methanol/ethyl acetate to give off-white crystals with m.p. 248°–250° C.

The preparation of the starting material is described in Examples 6 through 8.

EXAMPLE 6

(2-Amino-5-iodophenvl)(2-chlorophenyl)methanon

Iodine monochloride, 15 ml (21 g), was added to a solution of 23 g (0.1 mol) of (2-aminophenyl)(2 chlorophenyl)methanone [ref. E. Reeder and L. H. Sternbach, U.S. Pat. No. 3,371,085; February 1968] in 500 ml of methylene chloride cooled to −60° C. After stirring with cooling for 5 hours, the cooling bath was removed and the temperature of the reaction mixture was allowed to reach 0° C. Following the addition of 300 ml of aqueous sodium bisulfite solution, the two phase system was stirred for 10 minutes. The organic phase was separated, dried over sodium sulfate and evaporated. The residue was crystallized from ether/hexane to yield 20 g (56%) of (2-amino-5-iodophenyl) (2-chlorophenyl)methanone with m.p. 120°–122° C.

EXAMPLE 7

5-(2-Chlorophenyl)-1,3-dihydro-7-iodo-2H-1,4-benzodiazepin-2-one

Bromoacetyl bromide, 15 ml, was added to a solution of 52 g (0.145 mol) of (2-amino-5-iodophenyl)(2-chlorophenyl) methanone in 300 ml of methylene chloride cooled to 0° C. A 10% aqueous solution of sodium carbonate, 150 ml, was added slowly with stirring and the two phase system was stirred in the cold for 30 minutes. The organic layer was separated, washed with water and dried over sodium sulfate. The solution was filtered and evaporated. Crystallization of the residue from methylene chloride/ether yielded 61 g (90%) of 2-bromo-N-[2-(2-chlorobenzoyl)-4-iodophenyl]acetamide with m.p. 150°–152° C. A solution of 50 g of this material in 1 liter of methylene chloride was added to 800 ml of liquid ammonia with dry-ice cooling. After refluxing for 16 hours, the cooling was discontinued and the ammonia was allowed to evaporate. The remaining solution was washed with water, dried over sodium sulfate and evaporated under reduced pressure. The residue was dissolved in 1 liter of ethanol and the solution was heated to reflux for 30 minutes after the addition of 15 ml of acetic acid. The crystals separated from the cooled reaction mixture were collected to leave 38 g (89%) of 5-(2-chlorophenyl)-1,3-dihydro-7-iodo-2H-1,4-benzodiazepin-2-one which melted at 260°–262° C. after recrysyallization from tetrahydrofuran/ethanol.

EXAMPLE 8

6-(2-Chlorophenyl)-B-iodo-1-methyl-4H-[1,2,4]triazolo[4,3-a][1,4]benzodiazepine

A solution of 15.7 g (0.04 mol) of 5-(2-chlorophenyl)-7-iodo-1,3-dihydro-2H-1,4-benzodiazepin-2-one in 350 ml of tetrahydrofuran was cooled to −30° C. potassium t-butoxide. 4.9 g (0.044 mol) was added and stirring under nitrogen was continued for 30 minutes at −10° to −5° C. Diethyl chlorophosphate, 6.6 ml, was then added and the mixture was stirred at this temperature for another 30 minutes. Following the addition of 3.4 g of acetyl hydrazine, stirring without cooling was continued for 1 hour and 150 ml of n-butanol was added. The tetrahydrofuran was distilled out of the reaction mixture over a period of 45 minutes. The residue was partitioned between water and toluene. The organic phase was washed with brine, dried over sodium sulfate and evaporated down to a small volume. The precipitated crystals were collected to leave 14 g of crude product which was purified by chromatography over 250 g of silica gel using 5% ethanol (V/V) in methylene chloride. The clean fractions were combined and evaporated. Crystallization from tetrahydrofuran/ethanol gave 8.5 g (49%) of 6-(2-chlorophenyl)-8-iodo-1-methyl-4H-[1,2,4]triazolo[4,3-a][1,4]benzodiazepine with m.p. 290°–292° C.

EXAMPLE 9

2-[3-[1-Ethyl-6-(2-fluorophenyl)-4H-[1,2,4]triazolo[4,3-a][1,4]benzodiazepin-8-yl]-2-propynyl]-1H-isoindole-1,3(2H)dione semihydrate.

A mixture of 435 mg (1 mmol) of 1-ethyl-6-(2-fluorophenyl)-8-iodo-4H-[1,2,4]triazolo[4,3-a][1,4]benzodiazepine, 220 mg of N-propargylphthalimide, 80 mg of triphenylphosphine, 20 mg of cuprous iodide, 0.5 ml of triethylamine and 10 ml of dimethylformamide was stirred and degassed with a stream of argon for 10 minutes. Palladium acetate, 30 mg, was then added and stirring under argon was continued for 48 hours. The reaction mixture was partitioned between methylene chloride and saturated agueous sodium bicarbonate solution. The organic phase was dried and evaporated under reduced pressure, at the end azeotropically with xylene. The residue was chromatographed over 30 g silica gel (Merck 70–230 mesh) using 5% (V/V) of ethanol in methylene chloride. Crystallization of the combined clean fractions from ethyl acetate yielded 0.41 g of 2-[3-[1-ethyl 6-(2-fluorophenyl)-4H-[1,2,4]triazolo[4,3-a][1,4]benzo-diazepin-8-yl]-2-propynyl]-1H-isoindole-1,3(2H)-dione semihydrate with m.p. 216°–219° C. The starting material was prepared as described in Example 10.

EXAMPLE 10

1-Ethyl-6-(2-fluorophenyl)-8-iodo-4H-[1,2,4]triazolo[4,3-a][1,4]-benzodiazepine

A mixture of 1 g of 5-(2-fluorophenyl)-7-iodo-2-hydrazino-7-iodo-3H-1,4-benzodiazepine (see example 3), 5 ml of triethyl orthopropionate and 10 ml of xylene was heated to reflux for 1 hour. The solvents were partially distilled over and the residue was diluted with hexane. The precipitated crystals were collected and recrystallized from methanol/ethyl acetate to leave 1.05 g (97%) of 1-ethyl-6-(2-fluorophenyl)-8-iodo-4H-[1,2,4]triazolo[4,3-a][1,4]benzodiazepine with m.p. 209°–211° C.

EXAMPLE 11

1-[3-[6-(2-Chlorophenyl)-1-methyl-4H-[1,2,4]triazolo[4,3-a]-[1,4]benzodiazepin-8-yl]-2-propynyl]-1H-indole-2,3-dione This compound was prepared by reacting 6-(2-chlorophenyl)-8-iodo-1-methyl-4H-[1,2,4]triazolo[4,3-a][1,4]benzodiazepine with 1-(2-propynyl)-1H-indole-2,3-dione [ref. A. Lindquist, p. Lagerstrom and R. Dahlbom, Acta Pharm. Suecica 9, 99 (1972)] as described in Example 9. The crude product was purified by chromatography over 40 fold amount of silica gel using 5% (V/V) of ethanol in methylene chloride. Crystallization from ethyl acetate qave yellow crystals of 1-[3-[6-(2-chlorophenyl)-1-methyl-4H-[1,2,4]triazolo[4,3-a][1,4]benzodiazepin-8-yl]-2-propynyl]-1H-indole 2,3-dione with m.p. 210°–212° C. These crystals contained according to microanalysis and pmr-spectrum 0.25 molar amounts of ethyl acetate.

EXAMPLE 12

2-[3-[6-(2-Chlorophenyl)-1-methyl-4H-[1,2,4]triazolo[4,3-a][1,4]benzodiazepin-8-yl-2-proynyl]-1H-benz[de]isoquinoline-1,3(2H)-dione This compound was obtained from the reaction of 6-(2-chlorophenyl)-8-iodo-1-methyl-4H-[1,2,4]triazolo[4,3-a][1,4]benzodiazepine with 2-(2-propynyl)-1H-benz[de]isoquinoline-1,3(2H)-dione as described in example 9. The crude product was chromatographed over 40 fold amount of silica gel using 4% (V/V) of ethanol in methylene chloride for elution. Crystallization from methylene chloride/ether and recrystallization from tetrahydrofuran/ethanol gave colorless crystals with m.p. 213°–215° C., containing 0.66 molar amounts of water according to pmr-spectrum and analysis.

The preparation of the acetylenic reaction component is described in Example 13.

EXAMPLE 13

2-(2-propynyl)-1H-benz[de]isoquinoline-1,3(2H)-dione

Potassium t-butoxide, 6.2 g (0.055 mol) was added to a solution of 9.9 g (0.05 mol) of naphthalimide in 50 ml of dimethylformamide cooled to −20° C. After stirring in the cold for 1 hour, 5 ml (0.055 mol) of propargyl bromide in 20 ml of dimethylformamide was added and the mixture was allowed to warm to room temperature. It was then heated to 45° C. for 45 minutes. After cooling, 15 ml of glacial acetic acid was added and the product was precipitated by addition of water. The solids were collected and recrystallized from ethyl acetate to leave 10 g (84%) of colorless crystals of 2-(2-propynyl)-1H-benz[de]isoquinoline-1,3-(2H)-dione with m.p. 235°–237° C.

EXAMPLE 14

8-[3-(1H-Benzimidazol-1-yl)-1-propynyl]-6-(2-chlorophenyl)-1-methyl-4H-[1,2,4]triazolo[4,3-a][1,4]benzodiazepine semihydrate This compound was similarly obtained by reacting 6-(2-chlorophenyl) 8-iodo-1-methyl-4H-[1,2,4]triazolo[4,3-a][1,4]benzodiazepine with 1-(2-propynyl)-1H-benzimidazole [ref. I. I. popov, P. V. Tkachenko and A. M. Simonov, Khim. Geterots. Soedin. 551, (1973)]. The product was isolated by chromatography over 40 fold amount of silica gel using 5%(V/V) of ethanol in methylene chloride. Crystallization from ethanol yielded colorless crystals with m.p. 165°–168° C. Analytical and spectroscopic data indicated a semihydrate.

EXAMPLE 15

3-8

3-[6-(2-Chlorophenyl)-1-methyl-4H-[1,2,4]triazolo[4,3-a][1,4]benzodiazepin-8-yl]-2-propynyl]-2,3-dihydro-1,3-benzoxazol-2-one hydrate Reaction of 6-(2-chlorophenyl)-8-iodo-1-methyl-4H-[1,2,4]triazolo[4,3-a][1,4]benzodiazepine with 3-(2-propynyl)-2,3-dihydro-1,3-benzoxazol-2-one [ref. A. Lindquist et al., Acta Pharm. Suecica 9, 99 (1972)] yielded after chromatography over 40 fold amount of silica gel with 3% (V/V) of ethanol in methylene chloride and crystallization from ethanol colorless crystals of 3-[3-[6-(2-chlorophenyl)-1-methyl-4H-[1,2,4]triazolo[4,3-a][1,4]benzodiazepin8-yl]-2-propynyl]-2,3-dihydro-1,3-benzoxazol-2-one hydrate with m.p. 158°–160° C. They analyzed for a monohydrate.

EXAMPLE 16

1-[3-[6-(2-Chlorophenyl)-1-methyl-4H-[1,2,4]triazolo[4,3-a][1,4]benzodiazepin-8-yl-2-propynyl]-1,3-dihydro-2H-indol-2-one This compound was prepared by coupling 6 (2-chlorophenyl)-8-iodo-1-methyl-4H-[1,2,4]triazolo[4,3-a][1,4]benzodiazepine with 1,3-dihydro-1-(2-propynyl)-2H-indol-2-one [ref. A. Lindquist et al., Acta Pharm. Suecica 9, 99 (1972)]. It was isolated and purified by chromatography over the 40 fold amount of silica gel using 5% (V/V) of ethanol in methylene chloride. Crystallization from ethanol gave a solvent with m.p. 141°–143° C. containing 0.33 mol of ethanol and 0.66 mol of water.

EXAMPLE 17

1-[3-[6-(2-Fluorophenyl)-1-methyl-4H-[1,2,4]triazolo-[4,3-a][1,4]-benzodiazepin-8-yl]-2-propynyl]benz[cd-]=indole-2(1H)-one A mixture of 0.84 g (2 mmol) of 6-(2-fluorophenyl)-8-iodo-1-methyl-4H-[1,2,4]triazolo[4,3-a][1,4]benzodiazepine, 0.5 g (2.4 mmol) of 1-(2- propynyl)benz[cd]indol-2(1H)-one, 90 mg of triphenylphosphine, 20 mg of cuprous iodide, 1 ml of triethylamine and 20 ml of dimethylformamide was degassed with a slow stream of argon for 15 minutes. Palladium acetate, 30 mg, was then added and the mixture was stirred under argon for five hours at room temperature. The reaction mixture was partitioned between methylene chloride and saturated aqueous sodium bicarbonate solution. The organic phase was dried and evaporated and the residue was chromatographed over 40 g of silica gel using 5% (V/V) of ethanol in methylene chloride for elution. Crystallization of the clean fractions from methanol-/ethyl acetate yielded light yellow crystals of the title compound with m.p. 224°–226° C.

The acetylenic starting material was prepared as described in Example 18.

EXAMPLE 18

1-(2-propynyl)benz[cd]indol-2(1H)-one

Potassium-t-butoxide, 6.17 g (0.055 mol) was added to a solution of 8.46 g (5 mmol) of benz[cd]indol-2(1H)-one in 100 ml of dimethylformamide. After stirring for 10 minutes at room temperature, 4.9 ml (0.055 mol) of propargyl bromide was added and the mixture was stirred for 1 hour at room temperature. The reaction mixture was acidified with acetic acid and partitioned between methylene chloride and saturated aqueous sodium bicarbonate solution. The organic layer was dried and evaporated and the residue was crystallized from tetrahydrofuran/ethanol to leave 8 g (77%) of product with m.p. 183°–186° C. The title compound was recrystallized for analysis twice from methylene chloride/ethyl acetate and had m.p. 185°–187° C.

EXAMPLE 19

4-[3-[6-(2-Fluorophenyl)-1-methyl-4H-[1,2,4]triazolo[4,3-a][1,4]benzodiazeoin-8-yl]-2-propynyl]-2H-1,4-benzothiazin-3(4H)-one Reaction of 0.84 g of 6-(2-fluorophenyl)-8-iodo 1-methyl-4H-[1,2,4]triaolo [4,3-a][1,4]benzodiazepine with 0.53 g (2.6 mmol) of 4-(2-propynyl)-2H-1,4-benzothiazin-3(4H)-one [ref. R. N. Prasad and K. Tietje, Can. J. Chem. 44, 1247 (1966)]as described in Example 17 yielded after chromatographic purification (5% ethanol in methylene chloride on silica gel) and crystallization from ethyl acetate 0.5 g (51%) of yellowish crystals of the title compound with m.p. 203°–206° C. These crystals contained according to pmr-spectrum and analysis 0.166 molar amounts of ethyl acetate.

EXAMPLE 20

4-[3-[6-(2-Fluorophenyl)-1-methyl-4H-[1,2,4]triazolo4,3-a][1,4]benzodiazepin-8-yl]-2-propynyl]-2H-1,4-benzoxazin-3(4H)-one This compound was similarly obtained by coupling 0.84 g of 6-(2-fluorophenyl)-8-iodo-1-methyl-4H-[1,2,4]triazolo[4,3-a][1,4]benzodiazepine with 4-(2-propynyl)-2H-1,4-benzoxazin-3(4H)-one [ref. A. Lindquist et al., Acta Pharm. Suecica 9, 99 (1972)]as described in Example 17. The product was isolated and purified by chromatography and was crystallized from ethyl acetate to give 0.55 g (56%) of light yellow crystals with m.p. 238°–240° C. These crystals contained 0.166 mol of ethyl acetate according to spectral and analytical data.

EXAMPLE 21

3-[3-[6-(2-Fluorophenyl)-1-methyl-4H-[1,2,4]triazolo[4,3-a][1,4]benzodiazeoin-8-yl]-2-propynyl]-4(3H)-quinazolinone monohydrate Reaction of 0.84 g (2 mmol) of 6-(2-fluorophenyl) 8-iodo-1-methyl-4H-[1,2,4]triazolo[4,3-a][1,4]benzodiazepine with 0.48 g (2.6 mmol) of 3-(2-propynyl)-4(3H)-quinazolinone [ref. J. Maillard et al., Chimie There. 3, 202 (1967)] as described in example 17 yielded 0.6 g (59%) of off-white product, crystallized from ethyl acetate. The crystals of the title compound with m.p. 199°–201° C. contained 1 mol of water and 0.166 molar amounts of ethyl acetate.

EXAMPLE 22

3-[3-[6-(2-Fluorophenyl)-1-methyl-4H-[1,2,4]triazolo[4,3-a][1,4]benzodiazepin-8-yl]-2-propynyl]-2-methyl-4(3H)-quinazolinone This compound was obtained by coupling 6-(2-fluorophenyl)-8-iodo-1-methyl-4H-[1,2,-4]triazolo[4,3-a][1,4]benzodiazepine with 2-methyl-3-(2-propynyl)-4(3H)-quinazolinone [ref. B. Danielsson, L. Kronberg and B. Akerman, Acta Pharm. Suecica, 6, 379, (1969)] as described in ex. 17. It was isolated in 57% yield and crystallized from ethyl acetate. m.p. 241°–244° C. with decomposition. The crystals contained 0.66 molar amounts of water.

EXAMPLE 23

2-[3-[6-(2-Fluorophenyl)-1-methyl-4H-[1,2,4]triazolo[4,3-a][1,4]benzodiazepin-8-yl]-2-propynyl]-2,3-dihydro-1H-isoindol-1-one Reaction of 6-(2-fluorophenyl)-8-iodo-1-methyl-4H-[1,2,4]triazolo[4,3-a][1,4]benzodiazepine with 2,3-dihydro-(2-propynyl)-1H-isoindol-1-one [ref. J. I. Neumeyer, U. V. Moyer, J. A. Richman, F. J. Rosenberg and D. G. Teiger, J. Med. Chem. 10, 615 (1967)] gave after chromatographic purification as described in example 17 and crystallization from ethyl acetate colorless crystals of the title compound with m.p. 165°–168° C. According to spectral and analytical data, these crystals contained 0.5 molar amounts of water and traces of ethyl acetate.

EXAMPLE 24 rac-2,3-Dihydro-2-[3-[6-(2-fluorophenyl)-1-methyl-4H-[1,2,4]triazolo[4,3-a][1,4]benzodiazepin-8-yl]-2-propynyl]-3-methoxy-1H-isoindol-1

This compound was prepared as described in example 1 by reacting 6-(2-fluorophenyl)-8-iodo 1-methyl-4H-[1,2,4]triazolo[4,3-a][1,4]benzodiazepine with rac. 2,3-dihydro-3-methoxy-2-(2-propynyl)-1H-isoindol-1-one. The product was not obtained in crystalline state and was characterized spectroscopically. For testing the compound was precipitated from tetrahydrofuran by addition of hexane and the resulting amorphous powder was dried under vacuum. Nmr(CDCl$_3$): 2.64 ppm (s, 3, CH3), 2.96 (s, 3, OMe), 4.1 (d,1) and 5.54 (d,1) (AB-system J=7 Hz, CH2), 4.2 (d,1) and 4.88 (d,1) (AB-system, J=9 Hz, CH2 of propynyl), 6.07 (s,1,C3-H). 6.9–8.0 (m, 11, aromatic H). The preparation of the acetylenic reaction component is described in Example 25.

EXAMPLE 25 rac. 2,3-Dihydro-3-methoxy-2-(2-propynyl)-1H-isoindol-1-one

A solution of 2 g of 2,3-dihydro-3-hydroxy-2-(2-propynyl)-1H-isoindol-1-one in 20 ml of thionyl chloride was allowed to sit at room temperature over night. The reagent was evaporated under reduced pressure, at the azeotropically with toluene. The residue was dissolved in 20 ml of methanol and the solution was treated with 5 ml of triethylamine. After heating on the steam bath for 5 minutes, the mixture was evaporated and the residue was partitioned between methylene chloride and saturated aqueous sodium bicarbonate solution. The organic layer was separated, dried and evaporated. The residue was crystalized from ether/hexane to leave 0.8 g of colorless crystals of the title compound with m.p. 85°–87° C.

The preparation of the starting material is described in Example 55.

EXAMPLE 26

2-[3-[6-(2-Fluorophenyl)-1-methyl-4H-[1,2,4]triazolo[4,3-a][1,4]benzodiazepin-8-yl]-2-propynyl]-1,2,4-triazolo[4,3-a]pyridin-3(2H)-one This compound was obtained as described in example 17 by coupling of 6-(2-fluorophenyl)-8-iodo-1-methyl-4H-[1,2,4]triazolo[4,3-a][1,4]benzodiazepine with 2-(2-propynyl)-1,2,4-triazolo[4,3-a]pyridin-3(2H)-one. The product was purified by chromatography in the usual fashion and crystallized from ethyl acetate/ethanol. Recrystallization from ethanol gave light yellow crystals with m.p. 170°–173° C. They contained 0.66 molar amounts of water. The synthesis of the required acetylene is described in Example 27.

EXAMPLE 27

2-(2-propynyl)-1,2,4-triazolo[4,3-a]pyridin-3(2H)-one

Potassium-t-butoxide, 3 g (2.6 mmol), was added to a solution of 3.25 g (2.4 mmol) of 1,2,4-triazolo[4,3-a]pyridin-3(2H)-one in 75 ml of dimethylformamide. After stirring under nitrogen for 15 minutes, 2.35 ml (2.6 mmol) of propargyl bromide was added and stirring at room temperature was continued for 1 hour. The solvent was evaporated under reduced pressure, at the end azeotropically with xylene. The residue was extracted with methylene chloride and the solution was evaporated. Chromatographic purification of the residue on silica gel (5% ethanol in methylene chloride) and crystallization of the clean fractions from methanol yielded 1.7 g of colorless crystals of the title compound with m.p. 126°–128° C.

EXAMPLE 28

6-(2-Fluorophenyl)-1-methyl-8-[3-(1H-indazol-1-yl)-1-propynyl]-4H-[1,2,4]triazolo[4,3-a][1,4]benzodiazepine This compound was obtained as described in example 17 by reaction of 6-(2-fluorophenyl)-8-iodo-1-methyl-4H-[1,2,4]triazolo[4,3-a][1,4]benzodiazepine with 1-(2-propynyl)-1H-indazole [ref. p. V. Tkachenko, I. I. popov, A. M. Simonov and Yu. V. Medvedov, Khim. Geterotsikl. Soedin. 11, 1542 (1975)]. The chromatographically isolated product was crystallized from ethyl acetate to give yellowish crystals with m.p. 148°–151° C.

EXAMPLE 29

1-[3-[6-(2-FluorophenVl)-1-methyl-4H-[1,2,4]triazolo[4,3-a][1,4]benzodiazepin-8-yl]-2-propynyl]-1,3-dihydro-2H-indol-2-one hydrate Coupling of 6-(2-fluorophenyl)-8-iodo-1-methyl-4H-[1,2,4]triazolo [4,3-a][1,4]benzodiazepine with 1,3-dihydro-1-(2-propynyl)-2H-indol-2-one [ref. A. Lindquisr et al., Acta Pharm. Suecica 9, 99 (1972)] as described in Example 17 qave colorless crystals of the title compound from ethyl acetate, which analyzed for a hydrate and had m.p. 233°–235° C.

EXAMPLE 30

2-[3-[6-(2-Fluorophenyl)-1-methyl-4H-[1,2,4]triazolo[4,3-a][1,4]benzodiazeoin-8-yl]-2-propynyl]-1,2-benzisothiazol-3(2H)-one 1,1-dioxide semihydrate This compound was prepared according to the procedure of example 17 by reacting 6-(2-fluorophenyl)-8-iodo-1-methyl-4H-[1,2,4]triazolo[4,3-a][1,4]benzodiazepine with 2-(2-propynyl)-1,2-benzisothiazol-3(2H)-one 1,1-dioxide [ref. R. Granger and J. Giroux, Frech patent No. 1,273,867, February 1962; C. A. 57, 7285i (1963)]. The product was isolated and purified by chromatography and crystallized from methylene chloride/ethyl acetate to yield colorless crystals with m.p. 238°–240° C. The crystals analyzed for a semi hydrate.

EXAMPLE 31

2-[3-[6-(2-Fluorophenyl)-1-methyl-4H-[1,2,4]triazolo[4,3-a][1,4]benzodiazeoin-8-yl]-2-propynyl]-tetrahydro-1H-pyrrolo[1,2-c]imidazole-1,3(2H)-dione semihydrate Coupling of 6-(2-fluorophenyl)-8-iodo-1-methyl 4H-[1,2,4]triazolo[4,3-a][1,4]benzodiazepine with 2-(2-propynyl)-tetrahydro-1H-pyrrolo[1,2-c]imidazole-1,3(2H)-dione under the conditions described in Example 17 yielded after chromatographic purification and crystallization from ethanol off-white crystals of the title compound with m.p. 158°–161° C. which analyzed for a semihydrate.

The synthesis of the acetylenic reaction component is outlined in Example 32.

EXAMPLE 32

2-(2-Propynyl)-tetrahydro-1H-pyrrolo1,2-c]imidazole-1,3(2H)-dione

Potassium-t-butoxide, 1.23 g (11 mmol), was added to a solution of 1.4 g (10 mmol) of tetrahydro-1H-pyrrolo[1,2-c]imidazole-1,3(2H)-dione (L-proline-hydantoin) [ref. T. Suzuki, K. Igarashi, K. Hase and K. Tuzimura, Agr. Biol. Chem., 37, 411 (1973)] in 20 ml of dimethylformamide. After stirring for 10 minutes at room temperature, 1 ml (11 mmol) of propargyl bromide was added and stirring under nitrogen was continued for 2 hours. The reaction mixture was acidified with acetic acid and evaporated under reduced pressure. The residue was slurried with methylene chloride and filtered. The filtrate was evaporated and the residue was chromatographed over 45 g of silica gel using 5% (V/V) of ethanol in methylene chloride. The clean fractions were combined and evaporated to leave the title compound as a colorless viscous oil. Nmr(CDC13): 1.72 ppm, (m,1,C6-H), 1.9–2.4 (m,3,C6-H,C7-H), 2.22 (t,1,J=1.5 Hz, acetylenic H), 3:24 (m,1,C5-H), 3.70 (m,1,C5-H), 4.11 (dd, 1, J=4 Hz and 3.5 Hz, C7a-H), 4.23 (d,2,J=1.5 Hz, CH2).

EXAMPLE 33

2-[3-[6-(2-Fluorophenyl)-1-methyl-4H-[1,2,4]triazolo[4,3-a][1,4]benzodiazepin-8-yl]-2-propynyl]-3a,4,7,7a-tetrahydro-1H-isoindole-1,3(2H)-dione This compound was obtained by reaction of 6-(2-fluoro-phenyl)-8-iodo-1-methyl-4H-[1,2,4]triazolo[4,3-a][1,4]benzodiazepine with N-propargyl-tetrahydrophthalimide [ref. W. E. Hahn and A. Sokolowska, Soc. Sci. Lodz. Acta Chim. 18. 187 (1974)] following the procedure described in example 1. The product was isolated chromatographically and was crystallized from ethanol to give colorless crystals of the title compound with m.p. 259°–261° C. According to analytical data, these crystals contained 0.33 molar amounts of water.

EXAMPLE 34

1-[3-[6-(2-Fluorophenyl)-1-methyl-4H-[1,2,4]triazolo[4,3-a][1,4]benzodiazepin-8-yl]-2-propynyl]-3,4-dihydro-4-methyl-1H-1,4-benzodiazepine-2,5-dione Coupling of 6-(2-Fluorophenyl)-8-iodo-1-methyl-4H[1,2,4]triazolo[4,3-a] [1,4]benzodiazepine with 3,4-dihydro-4-methyl-1-(2-propynyl)-1H-1,4-benzodiazepine 2,5-dione as described in example 17 gave after chromatography and crystallization from ethyl acetate colorless crystals with m.p. 179°–182° C. The crystals of the title compound contained according to analytical and nmr-data 0.16 mol of ethyl acetate and 0.66 mol of water. The preparation of the required acetylene is described in Example 54.

EXAMPLE 35

6-(2-Chlorophenyl)-1-methyl-8-[3-(3-pyridinyloxy)-1-propynyl]-4H-[1,2,4] triazolo[4,3a][1,4]benzodiazepine Coupling of 6-(2-chlorophenyl)-8-iodo-1-methyl-4-H[1,2,4]triazolo[4,3-a] [1,4]benzodiazepines with 1-(3-pyridinyloxy)-2-propyne [ref. J. Bruhn, J. Zsindely, H. Schmid and G. Frater, Helv. Chim. Acta 61, 2542 (1978)] as described in example 1 gave after chromatography and crystallization from ethanol/ether colorless crystals of the title compound with m.p. 128°–130° C. These crystals contained 0.66 molar amounts of water according to analytical data.

EXAMPLE 36

5

6-(2-Chlorophenyl)-1-methyl-8-(3-phenoxy-1-propynyl)-4H-[1,2,4]triazolo [4,3-a][1,4]benzodiazepine This compound was obtained by coupling 6-(2-chlorophenyl)-8-iodo-1-methyl-4H-[1,2,4]triazolo[4,3-a][1,4]benzodiazepine with 1-phenoxy-2-propyne as described in example 1. Chromatographic isolation and crystallization from ethyl acetate gave colorless crystals with m.p. 160°–162° C.

EXAMPLE 37

2-[3-[4-(2-Chlorophenyl)-9-methyl-6H-thieno[3,2-f][1,2,4]triazolo[4,3-a][1,4]diazepin-2-yl]-2-propynyl]-1H-benzde]isoquinoline-1,3(2H)-dione A mixture of 0.88 g (2 mmol) of 4-(2-chlorophenyl)2-iodo-9-methyl-6H-thieno[3,2-f][1,2,4]triazolo[4,3-a][1,4]diazepine, 565 mg (2.4 mmol) of 2-(2-propynyl)-1H-benz[de]-isoquinolin-1,3(2H)-dione, 1 ml of triethylamine, 20 mg of cuprous iodide, 90 mg of triphenylphosphine and 20 ml of dimethylformamide was degassed by a slow stream of argon for 15 minutes. Palladium acetate, 30 mg, was then added and the mixture was stirred at room temperature under argon for 20 hours. Thin layer chromatography indicated practically complete reaction after 5 hours. The reaction mixture was partitioned between methylene chloride and saturated aqueous sodium bicarbonate solution. The organic layer was separated, dried over sodium sulfate and evaporated under reduced pressure, at the end azeotropically with xylene to drive over the residual dimethylformamide. The residue was chromatographed over 40 g silica gel using 5%(V/V) of ethanol in methylene chloride for elution. The clean fractions were combined and evaporated. Crystallization from methanol/ethyl acetate gave 0.58 g (53%) of of the title compound with m.p. 188°–192° C. A different crystalline modification with m.p. 252°–254° C. was also observed.

EXAMPLE 38

1-[3-[4-(2-Chlorophenyl)-9-methyl-6H-thieno[3,2-f][1,2,4]triazolo[4,3-a][1,4]diazepin-2-yl]-2-propynyl]-1H-indole-2,3-dione This compound was prepared as described in Example 37 by coupling of 4-(2-chlorophenyl)-2-iodo-9-methyl 6H-thieno[ 3,2-f][1,2,4]triazolo[4,3-a] [1,4]diazepine with 1-(2-propynyl)-1H-indole-2,3-dione [ref. A. Lindquist et al., Acta Pharm. Suecica 9, 99 (1972)]. Chromatographic isolation and crystallization from methanol/ethyl acetate gave orange crystals with m.p. 185°–190° C. with foaming at 130°–140° C. These crystals contained according to analytical and spectral data molar amounts of ethyl acetate.

EXAMPLE 39

1-[3-[4-(2-Chlorophenyl)-9-methyl-6H-thieno[3,2-f][1,2,4]triazolo[4,3-a][1,4]diazepin-2-yl]-2-propynyl]-benz[cd]indol-2(1H)-one Reaction of 4-(2-chlorophenyl)-2-iodo-9-methyl-6H-thieno[3,2-f][1,2,4] triazolo[4,3-a][1,4]diazepine with 1-(2-propynyl)-benz[cd]indol-2(1H)-one as described in Example 37 yielded after chromatographic purification and slow crystallization from ethyl acetate yellow crystals with m.p. 202°–205° C. These crystals contained according to analytical data 0.75 mol of water. Treatment of this product with ethanolic hydrogen chloride and addition of ethyl acetate gave a crystalline hydrochloride of the title compound with m.p. 219°–222° C.

EXAMPLE 40

1-[3-[4-(2-Chlorophenyl)-9-methyl-6M-thieno[3,2-f][1,2,4]triazolo[4,3-a][1,4]diazepin-2-yl]-2-propynyl]-1,3-dihydro-2H-indol-2-one This compound was prepared by reacting 4-(2-chlorophenyl)-2-iodo-9-methyl-6H-thieno[3,2-f][1,2,4]triazolo[4,3-a][1,4]diazepine with 1,3-dihydro-1-

(2-propynyl)-2H-indol-2-one [ref. A. Lindquist et al., Acta Pharm. Suecica. 9, 99 (1972)] as described in Example 37. It was isolated be chromatography and crystallized from ethyl acetate to give yellowish crystals with m.p. 203°–206° C. These crystals contained according to nmr-spectral and analytical data 0.66 molar amounts of water and traces of ethyl acetate.

EXAMPLE 41

2-[3-(1H-Benzimidazol-1-yl)-1-propynyl]-4-(2-chlorophenyl)-9-methyl-6H-thieno[3 2-f][1,2,4]triazolo[4,3-a][1,4]diazepine Coupling of 4-(2-chlorophenyl)-2-iodo-9-methyl-6H-thieno[3,2-f][1,2,4] triazolo[4,3-a][1,4]diazepine with 1-(2-propynyl)-1H-benzimidazole [ref. I. I. popov et al., Khim. Geterosikl. Soedin., 551, (1973)] yielded after chromatographic isolation and crystallization from ethanol/hexane off-white crystals with m.p. 215°–217° C. The crystals of the title compound contained 0.66 molar amounts of water based on the analytical data.

EXAMPLE 42

2-[3-[4-(2-Chloroohenyl)-9-methyl-6H-thieno[3,2-f][1,2,4]tri-azolo[4,3-a][1,4]diazepin-2-yl]-2-propynyl]-1,2,4-triazolo[4,3-a]pyridin-3(2H)-one This compound was obtained by coupling 4-(2-chlorophenyl)-2-iodo-9-methyl-6H-thieno[3,2-f][1,2,4]triazolo[1,4]diazepine with 2-(2-propynyl)-1,2,4-triazolo[4,3-a]pyridin-3(2H)-one as described in Example 37. It was isolated by chromatography using 7.5% (V/V) of ethanol in methylene chloride for elution. Crystallization from ethanol gave 0.55 g (55%) of yellow crystals with m.p. 220°–223° C. According to analytical and nmr-spectral data, these crystals contained 0.25 molar amounts of ethanol.

EXAMPLE 43

2-[3-[4-(2-Chlorophenyl)-9-methyl-6H-thieno[3,2-f][1,2,4]triazolo[4,3-a][1,4]diazepin-2-yl]-2-propynyl]-1,2-benzisothiazol-3(2H)-one 1,1-dioxide The title compound was prepared by reacting 4-(2-chlorophenyl)2-iodo-9-methyl-6H-thieno[3,2-f][1,2,4]triazol[4,3-a][1,4]diazepine with 2-(2-propynyl)-1,2-benzisothiazol-3(2H)-one 1,1-dioxide [ref. R. Granger and J. Giroux, French patent No. 1,273,867 February 1962] as described in Example 37. It was isolated by chromatography and crystallized from ethyl acetate to give colorless crystals with m.p. 232°–234° C.

EXAMPLE 44

4-(2-Chlorophenyl)-9-methyl-2-[3-(3-pyridinyloxy)-1-propynyl]-6H-thieno [3,2-f][1,2,4]triazolo[4,3-a][1,4]diazepine Coupling of 4-(2-chlorophenyl)-2-iodo-9-methyl -6H-thieno[3,2-f][1,2,4] triazolo[4,3-a][1,4]diazepine with 1-(3-pyridinyloxy)-2-propyne [ref. J. Bruhn J., Zsindely, H. Schmid and G. Frater, Helv. Chim. Acta 61, 2542 (1978)] under conditions described in EXAMPLE 37 yielded after the usual chromatographic isolation resinous material containing the title compound which did not crystallize and was therefore characterized spectroscopically only. Nmr (CDCl3): 2.72 ppm (s,3,Me) 4.95 (s,4,CH2; C6-H), 6.8 (s.1,C3-H) 7.2–7.6 (m,6,aromatic H), 8.26 (m,1,) and 8.36 (broad s,1) pyridine C2 and C6-H).

EXAMPLE 45

4-(2-Chlorophenyl)-9-methyl-2-[3-(1H-indazol-1-yl)-1-propynyl]-6H-thieno [3,2-f][1,2,4,]triazolo[4,3-a][1,4]diazepine This compound was prepared as described in Example 37 by reaction of 4-(2-chlorophenyl)-2-iodo-9-methyl-6H-thieno[3,2-f][1,2,4]triazolo[4,3-a] [1,4]diazepine with 1-(2-propynyl)-1H-indazole [ref. P. V. Tkachenko et al., Khim. Gertersikl. Soedin., 1542 (1975)]. The product was isolated and purified by chromatography and was crystallized from ethyl acetate/ether to yield off-white crystals with m.p. 170°–173° C.

EXAMPLE 46

6-(2-Fluorophenyl)-8-[3-(1H-indol-1-yl)-1-propynyl]-1-methyl-4H-[1,2,4] triazolo[4,3-a][1,4]benzodiazepine Coupling of 6-(2-fluorophenyl)-8-iodo-1-methyl-4H-1,2,4]triazolo[4,3-a] [1,4]benzodiazepine with 1-(2-propynyl)-1H-indole [ref. A. J. Hubert and H. Reimlinger, J. Chem Soc. C. 606 (1968)] as described in Example 17 gave after chromatography and crystallization from ethyl acetate/ether off-white crystals with m.p. 167°–169° C.

EXAMPLE 47

1-[3-[6-(2-Fluorophenyl)-1-methyl-4H-[1,2,4]triazolo4,3-a][1,4]benzodiazepin-8-yl]-2-propynyl]-3,7-dihydro-3,7-dimethyl-1H-purine-2,6-dione Reaction of 6-(2-fluorophenyl)-8-iodo-1-methyl4-H-1,2,4]triazolo[4,3-a] [1,4]benzodiazepine with 3,7-dihydro-3,7-dimethyl-1-(2-propynyl)-1H-purine-2,6-dione [ref. J. W. Daly, W. L. padgett and M. T. Shamim, J. Med. Chem. 29,1305, (1986)] yielded after chromatography and crystallization from methylene chloride/ethanol off-white crystals of the title compound with m.p. 290°–292° C. These crystals contained 0.75 molar amounts of water according to analytical data.

EXAMPLE 48

2-[4-[6-(2-Fluorophenyl)-1-methyl-4H-[1,2,4]triazolo[4,3-a][1,4]benzodiazepin-8-yl]-3-butynyl]-1H-isoindole-1,3(2H)-dione This compound was obtained by coupling of 6-(2-fluorophenyl)8-iodo-1-methyl-4H-[1,2,4]triazolo[4,3-a][1,4]benzodiazepine with 2-(3-butyn-1-yl)-1H-isoindole-1,3(2H)-dione [ref. K. J. Hoffmann, P. Stenberg, C. Ljunggren, U. Svensson, J. L. G. Nilsson, O. Erikson, A. Hartkoorn and R. Lunden, J. Med. Chem 18, 278 (1975)] as described in Example 1. The product was isolated by chromatography and crystallized from ethanol to give colorless crystals with m.p. 128°–130° C. with foaming. These crystals contained according to analytical and spectral data molar amounts of ethanol.

EXAMPLE 49

4-[3-[4-(2-Chlorophenyl)-9-methyl-6H-thieno[3,2-f][1,2,4]triazolo[4,3-a][1,4]diazepin-2-yl]-2-propynyl]-2H-1,4-benzoxazin-3(4H)-one This compound was prepared by reaction of 4-(2-chlorophenyl)-2-iodo-9-methyl-6H-thieno[3,2-f][1,2,4]triazolo[4,3-a][1,4]diazepine with 4-(2-propynyl) 2H-1,4-benzoxazin-3(4H)-one [ref. A. Lindguist et al., Acta Pharm. Suecica, 9, 99 (1972)] as described in Example 37. After chromatographic isolation, the product was crystallized from ethyl acetate to give yellowish crystals with m.p. 190°-192° C. Treatment with ethanolic hydrogen chloride yielded a crystalline hydrochloride with m.p. 215°-218° C.

EXAMPLE 50

1-[3-[4-(2-Chlorophenyl)-9-methyl-6H-thieno[3,2-f][1,2,4]triazolo[4,3-a][1,4]diazepin-2-yl]-2-propynyl]-3,7-dihydro-3,7-dimethyl-1H-purine-2,6-dione This compound was obtained by coupling 4-(2-chlorophenyl)-2-iodo-9-methyl-6H-thieno[3,2-f][1,2,4,)triazolo[4,3-a][1,4]diazepine with 3,7-dihydro-3,7-dimethyl-1-(2-propynyl)-1H-purine-2,6-dione [Ref. J. W. Daly, W. L. Padgett and M. T. Shamim, J. Med. Chem. 29, 1305 (1986)] as described in Example 37. The product was isolated by chromatography and crystallized from ethyl acetate to yield yellow crystals with m.p. 277°-280° C.

EXAMPLE 51

7-[3-[4-(2-Chloroohenyl)-9-methyl-6H-thieno[3,2-f][1,2,4]triazoolo-4,3-a][1,4]diazepin-2-yl]-2-propynyl]-3,7-dihydro 1,3-dimethyl-1H-purine-2,6-dione Reaction of 4-(2-chlorophenyl)-2-iodo-9-methyl-6H-thieno[3,2-f][1,2,4] triazolo[4,3-a][1,4]diazepine with 3,7-dihydro-1,3-dimethyl-7-(2-propynyl)-1H-purine-2,6-dione [ref. J. W. Daly, W. L. Padgett and M. T. Shamim, J. Med. Chem. 29, 1305 (1986)] followed by chromatographic isolation and crystallization from ethyl acetate/ethanol gave yellow crystals of the title compound with m.p. 229°-232° C. These crystals contained 0.125 molar amounts of ethyl acetate according to analytical and spectral data.

EXAMPLE 52

2-[4-[4-(2-Chlorophenyl)-9-methyl-6H-thieno[3,2-f][1,2,4]triazolo[4,3-a][1,4]diazepin-2-yl]-3-butynyl]-1H-benz[de]isoquinoline-1,3(2H)-dione Coupling of 4-(2-chlorophenyl)-2-iodo-9-methyl-6H-thieno[3,2-f][1,2,4] triazolo[4,3-a][1,4]diazepine with 2-(3-butyn-1-yl)-1H-benz[de]isoquinoline-1,3(2H)-dione as described in Example 37 yielded after chromatography and crystallization from ethyl acetate light yellow crystals of the title compound with m.p. 175°-179° C. A higher melting crystalline modification with m.p. 227°-229° C. was also observed.

The preparation of the acetylenic reaction component is described in Example 53.

EXAMPLE 53

2-(3-Butyn-1-yl)-1H-benz[de]isoquinoline-1,3(2H)-dione

A mixture of 6 g (0.03 mol) of 1H-benz[de]isoquinoline-1,3(2H)-dione. 4 g (0.0355 mol) of potassium t-butoxide, 9 g (0.04 mol of 4-tosyloxy-1-butyne [ref. G. Eglinton and M. C. Whiting, J. Chem. Soc. 3650 (1950)] and 150 ml of dimethylformamide was heated on the steam bath with stirring for 1.5 hours. The bulk of the solvent was then removed under reduced pressure and the remaining suspension was filtered. The filtrate was diluted with water and the precipitated product was collected by filtration and dissolved in methylene chloride. The solution was dried and passed over a plug of silica gel using methylene chloride for elution. The fractions containing clean product were combined and evaporated. Crystallization from methylene chloride/ethanol gave the title compound as colorless needles with m.p. 191°-193° C.

EXAMPLE 54

3,4-Dihydro-4-methyl-1-(2-propynyl-1H-1,4-benzodiazepine2,5(2H)-dione propargyl bromide, 2.6 g (22 mmol), was added to a mixture of 3.8 g (20 mmol) of 3,4-dihydro-4-methyl-1H-1,4-benzodiazepine-2,5(2H)-dione [ref. M. Uskokovic and W. Wenner, U.S. Pat. No. 3,261,828, July 1966], 3.4 g of barium oxide and 100 ml of dimethylformamide. After stirring at room temperature for 2 hours, the reaction mixture was partitioned between water and methylene chloride. The organic phase was separated, washed with water, dried and evaporated. The residue was dissolved in ethyl acetate and the product was crystallized by addition of hexane to give the title compound as colorless crystals with m.p. 148°-150° C.

EXAMPLE 55 rac.
2,3-Dihydro-3-hydroxy-2-(2-propynyl)-1H-isoindol-1-one

A mixture of 10 g of N-propargylphthalimide and 2 g of sodium borohydride in 100 ml of ethanol was heated on the steam bath for 15 minutes with stirring. The resulting solution was concentrated under reduced pressure to one third of the volume and the product was crystallized by addition of ice and saturated sodium bicarbonate solution. The precipitated crystals of the title compound were collected by filtration, washed with water and sucked dry. After drying in vacuum they had m.p. 157°-159° C.

EXAMPLE 56

6-(2-Fluorophenyl)-1-methyl-8-[(trimethylsilyl)ethynyl]-4H-1,2,4triazolo[-4,3-a][1,4]benzodiazipine A mixture of 2.52 g of 6-(2-fluorophenyl)-8-iodo-1-methyl-4H-[1,2,4]triazolo[4,3-a][1,4]benzodiazepine, 270 mg of triphenylphosphine, 60 mg of cuprous iodide, 1.5 ml of triethylamine and 60 ml of dimethylformamide was stirred and degassed by a slow stream of argon for 10 minutes. Trimethylsilylacetylene, 1.2 ml, was then added and degassing was continued for 2 minutes. At this time 90 mg of palladium acetate was added and the mixture was stirred under argon for 4 hours at room temperature. The reaction mixture was partitioned between methylene chloride and saturated sodium bicarbonate solution. The organic layer was washed with water, dried and evaporated at the end azeotropically with xylene. The residue was chromatographed over 60 g of silica gel (Merck, 70-230 mesh) using 5% of ethanol in methylene chloride for elution. Crystallization of the combined clean fractions from ethyl acetate/hexane gave 2.05 g (86%) of colorless crystals of the title compound with m.p. 218°-220° C.

EXAMPLE 57

6-(2-Chlorophenyl)-1-methyl-8-[(trimethylsilyl)ethynyl]-4H[1,2,4]triazolo[4,3-a][1,4]benzodiazepine This compound was similarly prepared by coupling of 6-(2-chlorophenyl)-8-iodo-1-methyl-4H-[1,2,4]triazolo[4,3-a][1,4]benzodiazepine with trimethylsilylacetylene as described in Example 56. The product was isolated by chromatography and was crystallized from ethyl acetate/ hexane to give colorless crystals of the title compound with m.p. 243°–245° C.

EXAMPLE 58

4-(2-Chlorophenyl)-9-methyl-2-[(trimethylsilyl)ethynyl]-6H-thieno[-3,2-f][1,2,4]triazolo[4,3-a][1,4]diazeoine Reaction of 4-(2-chlorophenyl)-2-iodo-9-methyl-6H-thieno[3,2-f][1,2,4]triazolo[4,3-a][1,4]diazepine with trimethylsilylacetylene as described in Example 56 yielded after chromatographic isolation and crystallization from ethyl acetate hexane off-white crystals of the title compound with m.p. 135°–138° C.

EXAMPLE 59

8-Ethynyl-6-(2-fluoroohenyl)-1-methyl-4H-[1,2,4]triazolo [4,3-a][1,4]benzodiazepine Sodium hydroxide. 1 ml 10N, was added to a solution of 2.3 g of 6-(2-fluorophenyl)-1-methyl-8-[(trimethylsilyl) ethynyl]-4H-[1,2,4]triazolo [4,3-a][1,4]benzodiazepine in 50 ml of ethanol. The mixture was stirred under argon at room temperature for 1 hour and was then partitioned between methylene chloride and saturated agueous sodium bicarbonate solution. The organic phase was separated, dried and evaporated. The residue was filtered over a pad of silica gel using 5% of ethanol in methylene chloride for elution. The filtrate was evaporated and the residue was crystallized from ethyl acetate/hexane to yield colorless crystals of the title compound with m.p. 258°–260° C.

EXAMPLE 60

6-(2-Chlorophenyl)-8-ethynyl-1-methyl-4H-[1,2,4]triazolo [4,3-a][1,4]benzodiazepine This compound was similarly obtained by treatment of 6-(2-chlorophenyl)-1-methyl-8-[(trimethylsilyl)ethynyl]-4H-[1,2,4]triazolo[4,3][1,4-]benzodiazepine with sodium hydroxide in ethanol. The product was crystallized from ethanol to give colorless crystals of the title compound with m.p. 304°–306° C.

EXAMPLE 61

4-(2-Chlorophenyl)-2-ethynyl-9-methyl-6H-thieno[3,2-f][1,2,4]triazolo [4,3-a][1,4]diazepine Treatment of 4-(2-chlorophenyl)-9-methyl-2[(trimethylsilyl)ethynyl]-6H-thieno[3,2-f][1,2,4]triazolo [4,3-a][1,4]diazepine with sodium hydroxide in ethanol gave after chromatographic purification and crystallization from methanol/ethyl acetate colorless crystals of the tirle compound with m.p. 232°–233° C.

EXAMPLE 62

6-(2-Fluorophenyl)-1-methyl-8-(5-pyrimidinyl)ethynyl-4H[1,2,4]triazolo[4,3-a][1,4]benzodiazepine A mixture of 316 mg (1 mmol) of 8-ethynyl-6-(2-fluorophenyl)-1-methyl-4H-[1,2,4]triazolo[4,3-a][1,4]benzodiazepine 200 mg (1.25 mmol) of 5-bromopyrimidine, 45 mq of triphenylphosphine, 10 mg of cuprous iodide, 0.5 ml of triethylamine and 10 ml of dimethylformamide was stirred and degassed for 10 minutes by a slow stream of argon. Palladium acetate, 15 mg, was then added and stirring under argon was continued for 24 hours. The reaction mixture was partitioned between aqueous sodium bicarbonate solution and methylene chloride. The organic layer was washed with water, dried and evaporated, at the end azeotropically with xylene. The residue was chromatographed over 20 g of silica gel (Merck 70–230 mesh) using 5% of ethanol in methylene chloride. The combined clean fractions were evaporated and the residue was crystalized from ethyl acetate to give off-white crystals of the title compound with m.p. 143°–146° C.

EXAMPLE 63

6-(2-Chlorophenyl)-1-methyl-8-(2-thienylethynyl)-4H-[1,2,4]triazolo [4,3-a][1,4]benzodiazepine This compound was prepared by coupling of 6-(2-chlorophenyl)-8-ethynyl-1-methyl-4H-[1,2,4]triazolo[4,3-a]1,4]benzodiazepine with 2-iodothiophene as described in Example 62. The product was isolated and purified by chromatography and was crystallized from ethyl acetate to give crystals with m.p. 160°–163° C. These crystals contained according to analytical and spectral data 0.25 molar amounts of ethyl acetate and molar amounts of water.

EXAMPLE 64

1-{3-[4-(2-Chlorophenyl)-9-methyl-6H-thieno[3,2-f][1,2,4]triazolo[4,3-a][1,4]diazepin-2-yl]-2-propynyl-2(1H)quinolinone The title compound was prepared by reacting 4-(2-chlorophenyl)-2-iodo-9-methyl-6H thieno[3,2-f][1,2,4]triazolo[4,3-a][1,4]diazepine with 1-(2-propynyl)-2(1H)quinolinone [ref. A. Lindquist et al., Acta Pharm. Suecica, 9,99 (1972)]as described in EXAMPLE 37. It was isolated by chromatography over 50 g of silica gel using 5% (v/v) of ethanol in methylene chloride and was further purified by rechromatography over 50 g of silica gel using tetrahydrofuran. Crystallization from ethyl acetate/methanol gave off-white crystals of 1-{3-[4-(2-chlorophenyl)-9-methyl-6H-thieno[3,2-f][1,2,4]triazolo[4,3-a][1,4]diazepin-2-yl] 2-propynyl}-2(1H)-quinolinone with m.p. 162–165°. These crystals contained according to analytical data 0.5 molar amounts of water.

EXAMPLE 65

1-3-[4-(2-Chlorophenyl)-9-methyl-6H-thieno[3,2-f][1,2,4]triazolo[4,3-a][1,4]diazepin-2-yl]-2-propynyl]-3.4-dihydro2(1H)-quinolinone A mixture of 33 g (0.075 mol) of 4-(2-chlorophenyl) 2-iodo9-methyl-6H-thieno[3,2-f][1,2,4]triazolo[4,3-a][1,4]diazepine, 21 g (0.113 mol) of 3,4-dihydro-1-(2-propynyl)-2(1H) quinolinone [ref. A. Lindquist et al., Acta Pharm. Suecica, 9, 99 (1972)], 0.75 g of triphenylphosphine. 0.2 g of cuprous iodide, 60 ml of triethylamine and 600 ml of dimethylformamide was stirred and degassed by a stream of argon for 30 minutes. At this time 0.225 g of palladium acetate was added and the mixture was stirred at room temperature under argon for 3 days. The mixture was poured into 2.5 L of saturated aqueous sodium bicarbonate solution and ice. After stirring for 15 minutes, the precipitate was filtered off, washed with water and sucked dry. This material was dissolved in methylene chloride and the solution was washed with bicarbonate solution and dried over sodium sulfate. The solvent was removed under reduced pressure and the residue was dissolved by warming in ethyl acetate. After seeding and cooling, the crystallized product was collected and recrystallized from methanol/ethyl acetate to leave off-white crystals of 1-{3-[4-(2 chlorophenyl)-9-methyl-6H-thieno[3,2- f][1,2,4]triazolo[4,3.a][1,4]diazepin-2-yl]-2-propynyl}-3,4-dihydro 2(1H) quinolinone with m.p. 180°–182°.

EXAMPLE 66

2-3-[4-(2-Chlorophenyl)-9-methyl-6H-thieno[3,2-f][1,2,4]triazolo[4,3-a][1,4]diazepin-2-yl]-2-propynyl]-2,3-dihydro-1H-benz[de]isoquinolin-1-one The title compound was obtained by coupling 4-(2-chlorophenyl)-2-iodo-9-methyl-6H-thieno[3,2-f][1,2,4]triazolo[4,3-a][1,4]d.iazepine with 2,3-dihydro-2-(2-propynyl)-1H-benz[de]isoquinolin 1 one under the conditions described in Example 37. The product was isolated by chromatography over 40 fold amount of silica gel using tetrahydrofuran for elution. The fractions containing the title compound were combined and rechromatographed over the 30 fold amount of silica gel using 5% (v/v) of ethanol in methylene chloride. The combined clean fractions crystallized from methanol/ethyl acetate to give yellowish crystals of 2-{3-[4-(2-chlorophenyl)-9-methyl-6H-thieno[3,2-f][1,2,4]triazolo[4,3-a][1,4]diazepin-2-yl]-2-propynyl}-2,3-dihydro. 1H-benz[de]isoquinolin-1-one with m.p. 205°–210° with dec. These crystals contained 0.66 molar amounts of water according to the analytical and spectral data.

The preparation of the required propargyl derivative is described in Example 67.

EXAMPLE 67

2.3-Dihydro-2-(2-propynyl)-1H-benz[de]isoquinolin-1-one A mixture of 2 g of 2-(2-propynyl)-1H-benz[de]isoquinoline1.3(2H)-dione. 0.75 g of sodium borohydride, 50 ml of ethanol and 50 ml of tetrahydrofuran was warmed on the steam bath until solution was complete. An additional portion of 0.25 g of sodium borohydride was then added and the tetrahydrofuran was boiled off on the steam bath within 30 minutes. The remaining mixture was cooled, diluted with ice-water, buffered with acetic acid and diluted with agueous sodium bicarbonate solution. The precipitated product was filtered off after stirring over ice, was sucked dry and dissolved in about 250 ml of methylene chloride. The solution was dried and evaporated and the residue was slurried with methylene chloride/hexane. The crystals were collected and washed with ether to leave 0.67 g of 2,3-dihydro-3-hydroxy-2-(2-propynyl)-1H-benz-[de]isoguinolin-1-one which was reduced further as follows.

Sodium borohydride, 0.3 g. was added in small portions to a stirred solution of 0.6 g of the above intermediate in 6 ml of trifluoroacetic acid. After 15 minutes of reaction time, the mixture was partitioned between ice, ammonium hydroxide and methylene chloride. The organic layer was separated, dried and evaporated to leave a crystalline residue which was chromatographed over 30 g of silica gel using 10% (v/v) of ethyl acetate in methylene chloride. Crystallization of the combined clean fractions from ethyl acetate/hexane gave colorless of 2,3-dihydro-2-(2-propynyl)-1H-benz-[de]isoquinolin-1-one with m.p. 139°–140°.

EXAMPLE 68

1-{3-[4-(2-Chlorophenyl)-9-methyl-6H-thieno[3,2-f][1,2,4]triazolo[4,3-a][1,4]diazepin-2-yl]-2-propynyl}-1.3-dihydro-3-methyl-2H-benzimidazol-2-one The title compound was obtained by reacting 4-(2-chlorophenyl)-2-iodo-9-methyl-6H-thieno[3,2.f][1.2,4]triazolo[4,3-a][1,4]diazepine with 1,3-dihydro 1.methyl-3-(2-propynyl)-2H-benzimidazol-2-one under the conditions described in Example 37. The product was isolated by chromatography over the 50 fold amount of silica gel using tetrahydrofuran. Crystallization of the combined homogenous fractions from ethanol gave light yellow crystals of 1-{3-[4-(2-chlorophenyl)-9-methyl-6H-thieno[3,2-f][1,2,4]triazolo[4,3-a][1,4]diazepin-2-yl]-2-propynyl]-1,3-dihydro.3. methyl-2H-benzimidazol-2-one with m.p. 188°–191°.

The preparation of the required acetylene is described in Example 69.

EXAMPLE 69

1,3-Dihydro-1-methyl-3-(2-propynyl)-2H-benzimidazol-2-one potassium tert.-butoxide, 2.1 g (18.5 mmol). was added to a solution of 2.5 g (16.9 mmol) of 1,3-dihydro-1-methyl-2H-benzimidazol-2-one in 25 ml of dimethylformamide. After stirring under nitrogen for 15 minutes, 2.21 g (18.5 mmol) of propargyl bromide was added and the mixture was stirred at room temperature for 30 minutes. It was diluted with ice-water and the precipitate was filtered off washed with water and sucked dry. The crude product was passed over silica gel using 10% (v/v) of ethyl/acetate in methylene chloride for elution. Crystallization from ethyl acetate/hexane gave colorless crystals of 1,3-dihydro-1-methyl-3-(2-propynyl)-2H-benzimidazole-2-one with m.p. 110°–112°.

EXAMPLE 70 rac-2a-[3-[4-(2-Chlorophenyl)-9-methyl-6H-thieno[3,2-f][1,2,4]triazolo[4,3-aj[1,4]diazepin-2-yl-2-propynyl}-2a,3,4,5tetrahydrobenz[cd]indol-2(1H)-one The title compound was prepared by coupling 4-(2-chlorophenyl)-2-iodo-9-methyl-6H-thieno[3,2-f][1,2,4]triazolo[4,3-a][1,4]diazepine with rac-2a,3,4,5-tetrahydro-2a-(2-propynyl)benz[cd]indol-2(1H)-one under the conditions described in Example 17. The product was isolated by chromatography over the 50-fold amount of silica gel using 5% (v/v) of ethanol in methylene chloride for elution. The combined clean fractions were evaporated and the residue was crystalized from ethyl acetate/ether to give colorless crystals of rac-2a-{3-[4-(2-chlorophenyl)-9-methyl-6H-thieno[3,2-f][1,2,4]triazolo[4,3-a][1,4]diazepin 2-yl]-2 propynyl}-2a,3,4,5-tetrahydrobenz[cd]indol-2(1H) one with m.p. 215°–217°.

The preparation of the required propargyl compound is described in Example 71.

EXAMPLE 71 rac-2a,3,4,5-Tetrahydro-2a-(2-propynyl)benz[cd]indol-2(1H) -one

Potassium tert.-butoxide, 4.94 g (0.044 mol), was added to a solution of 6.92 g (0.04 mol) of rac-2a,3,4,5-tetrahydro-benz[cd]indol-2(1H)-one in 50 ml of dimethylformamide. After stirring for 15 minutes under nitrogen, 5.23 g or 3.9 ml of propargyl bromide was added and stirring was continued for 30 minutes. The mixture was diluted with water and ice and the precipitate was collected by filtration, washed with water and sucked dry. The solids were dissolved in methylene chloride and the solution was dried and evaporated. Crystallization of the residue from ethyl acetate gave crude product of rac-2a,3,4,5-tetrahydro-2a-(2-propynyl)benz[c,d]indol-2(1H)-one with m.p. 174–177° which was recrystallized from ethyl acetate to melt at 177°–180°.

EXAMPLE 72

2-[3-(9H-Carbazol-9-yl)-1-propynyl]-4-(2-chlorophenyl)-9-methyl-6H-thieno[3,2-f][1,2,4]triazolo[4,3-a][1,4]diazepine dihydrochloride The title compound was obtained by reacting 4-(2-chlorophenyl)-2-iodo-9-methyl-6H-thieno[3,2-f][1,2,4]triazolo[4,3-a][1,4]diazepine with 5-(2-propynyl)-5H-carbazole [ref. J. L. Dumont et al.. Bull. Soc. Chim. Fr. 1197, (1967)]under the conditions described in Example 37. The product was purified by chromatography over the 60-fold amount of silica gel using 5% (v/v) of ethanol in methylene chloride. The combined clean fractions did not crystallize and the viscous resin was converted to a crystalline dihydrochloride by treatment with excess ethanolic hydrogen chloride in ethanol/ethyl acetate. The yellow crystals of 2-[3-(9H-carbazol-9-yl)-1-propynyl]4-(2-chlorophenyl) 9-methyl 6H-thieno[3,2-f][1,2,4]triazolo[4,3-a][1,4]diazepine dihydrochloride had m.p. 180°–184°.

EXAMPLE 73

5-{3-[4-(2-Chlorophenyl)-9-methyl-6M-thieno[3,2-f][1,2,4}triazolo[4,3-a][1,4]diazepin-2-yl]-2-propynyl]-phenanthridin6(5H)-one A mixture of 44 g (0.1 mol) of 4-(2-chlorophenyl)-2-iodo.9-methyl-6H-thieno[3,2-f][1,2,4]triazolo[4,3-a][1,4]diazepine, 28 g (0.12 mol) of 5-(2-propynyl)-6(5H)-phenanthridinone, [ref. R. F. Cookson et al. J. Herterocyclic Chem., 9, 475 (1972)]. 1 g of triphenylphosphine, 0.25 g of cuprous iodide, 80 ml of triethylamine and 800 ml of dimethylformamide was degassed by as slow stream of argon for 30 minutes. Palladium acetate, 0.3 g, was then added and the mixture was stirred under argon for 4 days at room temperature. The insoluble material was removed by filtration over celite and the filtrate was concentrated to about 400 ml under reduced pressure. This solution was poured into 2 L of saturated aqueous sodium bicarbonate with stirring. The precipitate was collected by filtration after 10 minutes and was washed with water and sucked dry. The solids were partitioned between 2 L of methylene chloride containing 5% (v/v) of ethanol and sodium bicarbonate solution. The organic layer was dried over sodium sulfate, filtered and evaporated partially. After dilution with 500 ml of ethyl acetate. the solution was concentrated on the steam bath with crystallization of the product. After cooling, the crystals were collected and washed with ethyl acetate and ether to leave 56.5 g of the title compound. The analytical sample was recrystallized once from ethanol and then from tetrahydrofuran/ethyl acetate to give off-white crystals of 5-{3-[4-(2-chlorophenyl)-9-methyl-6H-thieno[3,2-f][1,2,4]triazolo[4,3-a][1,4]diazepin-2 yl]-2 propynyl}-phenanthridin-6(5H)-one with m.p. 247°–249°.

EXAMPLE 74

6-3-[4-(2-chlorophenyl)-9-methyl-6H-thieno[3,2-f][1,2,4]triazolo[4,3-a][1,4]diazepin-2-yl]-2-propynyl}-5H-dibenzc,e]azepine-5,7(6H)-dione The title compound was synthesized by reacting 4-(2-chlorophenyl)-2-iodo-9-methyl-6H-thieno[3,2.f][1,2,4]-triazolo[4,3-a][1,4]diazepine with 6-(2-propynyl)-5H.dibenz[c,e]azepine-5,7(6H)-dione [ref. J. R. Grunder et al., J. pharm. Sci., 62, 1204 (1973)]under the conditions used in Example 37. The product was purified by chromatography over the 50-fold amount of silica gel using 5% (v/v) of ethanol in methylene chloride. The combined clean fractions were evaporated and the residue was crystallized from ethanol/ethyl acetate to give off-white crystals of6-{3-[4-(2-chlorophenyl)-9-methyl 6H-thieno[3,2-f][1,2,4]triazolo[4,3-a][1,4]diazepin.2-yl]-2 propynyl}-5H-dibenz[c,e]azepine-5,7(6H)-dione with m.p. 220°–223°. These crystals contained 0.166 molar amounts of ethyl acetate according spectral and analytical data.

EXAMPLE 75

1-3-[4-(2-Chlorophenyl)-9-methyl-6H-thieno[3,2-f][1,2,4]triazolo[4,3-a][1,4]diazeoin-2-yl]-2-propynyl]-2a,3,4,5-tetrahydro-2a-methylbenz[c,d]indol-2-(1H)-one dihydrochloride The title compound was obtained by coupling of 4-(2-chlorophenyl)-2-iodo-9-methyl-6H-thieno[3,2-f]1,2,4]triazolo[4,3-a][1,4]diazepine with rac-2a,3,4,5-tetrahydro-2a-methyl-1- (2-propynyl)-benz[c,d]indol. 2(1H).one under the conditions used in Example 37. The product was purified by chromatography over the 50-fold amount of silica gel using 5% (v/v) of ethanol in methylene chloride for elution. The combined clean fractions were evaporated to leave a resinous material which did not crystallize but yielded a crystalline dihydrochloride upon treatmnent with excess ethanolic hydrogen chloride and ethyl acetate. These crystals contained 0.33 molar amounts of ethanol according spectral and analytical data. The pale yellow crystals of 1-{3-[4-(2-chlorophenyl)-9-methyl-6H-thieno[3,2-f][1,2,4]triazolo[4,3-a][1,4]diazepin-2-yl]-2-propynyl}-2a,3,4,5-tetrahydro-2a-methylbenz[c,d]indol-2-(1H)-one dihydrochloride had m.p. 175°–178°.

The propargyl starting material was synthesized as described in Example 76.

EXAMPLE 76 rac-2a,3,4,5-Tetrahydro-2a-methyl-1-(2-propynyl)-benz[c,d]indol2(1H)-one

Potassium tert.-butoxide, 4.94 g (0.044 mol), was added to a solution of 6.92 g (0.04 mol) of rac-2a,3,4,5-tetrahydro. benz[cd]indol-2(1H)-one in 50 ml of dimethylformamide. After stirring for 15 minutes under nitrogen, 6.24 g or 2.75 ml (0.044 mol) of methyl iodide was added and stirring was continued for 30 minutes. After dilution with water and ice, it was extracted with methylene chloride. The extracts were dried over sodium sulfate and evaporated. The residue was chromatographed over silica gel using 10% (v/v) of ethyl acetate in methylene chloride. The combined clean fractions were evaporated and the residue was crystallized from ether to give 3.2 g of colorless rac-2a,3,4,5-tetrahydro.-2amethylbenz[c,d]indol-2(1H).one with m.p. 148 150°.

This material, 2.5 g (13.3 mmol), was dissolved in 20 ml of dimethylformamide. The solution was treated with 1.65 g (14.7 mmol) of potassium tert.-butoxide and was stirred under nitrogen for 15 minutes. propargyl bromide, 1.75 g or 1.31 ml (14 mmol), was then added and stirring at room temperature was continued for 30 minutes. The reaction mixture was diluted with ice and saturated sodium bicarbonate solution. The precipitate was collected by filtration and the solids were washed with water and sucked dry. It was dissolved in methylene chloride and the dried solution was filtered over a plug of silica gel. The filtrate was evaporated and the residue was crystallized from ethyl acetate/hexane to give colorless crystals of rac-2a,3,4,5-tetrahydro-2a-methyl-1-(2-propynyl)benz[c,d]indol-2(1H)-one with m.p. 127°–130°.

EXAMPLE 77

4-(2-ChIorophenyl)-9-methyl-2-[3-(phenoXy)-1-propynyl]-6H-thieno 3,2-f][1,2,4]triazolo[4,3-a1[1,4]diazeoine dihydrochloride The title compound was obtained by coupling 4-(2-chlorophenyl)-2-iodo-9-methyl-6H-thieno[3,2.f][1,2,4]-triazolo[4,3-a][1,4]diazepine with 3-phenoxy.1-propyne under the conditions described in Example 37. The product was purified by chromatography over the 50-fold amount of silica gel using 5% (v/v) of ethanol in methylene chloride. The evaporated clean fractions left a viscous oil which did not crystallize but yielded a crystalline dihydrochloride upon treatment with excess ethanolic hydrogen chloride and ethyl acetate. The pale yellow crystals of 4-(2-chlorophenyl)-9-methyl-2-[3-(phenoxy)-1-propynyl-6H-thieno[3,2-f][1,2,4]triazolo[4,3-a][1,4]diazepine dihydrochloride melted with foaming at 48°–151° and analyzed for a hydrate.

EXAMPLE 78

1-{3-[4-(2-Chlorophenyl)-9-methyl-6H-thieno[3,2-f][1,2,4]triazolo[4,3-a][1,4]diazepin-2-yl]-2-propvnyl}-3-methyl-2,4 (1H,3H)-quinazolinedione A mixture of 0.88 g of 4-(2-chlorophenyl)-2-iodo.9-methyl-6H-thieno[3,2-f][1,2,4]triazolo[4,3-a][1,4]diazepine, 0.65 g of 3-methyl-1-(2-propynyl)-2,4(1H,3H)-quinazolinedione [ref. B. Danielsson et al., Acta Pharm. Suecica, 2, 167 (1965)]. 90 mg of triphenylphosphine, 20 mg of cuprous iodide, 2 ml of triethylamine and 50 ml of dimethylformamide was degassed with argon for 10 minutes. Palladium acetate, 30 mg, was then added and the mixture was heated up to 90°–95° within 30 minutes with stirring under argon. The temperature was maintained at 90°–95° for 15 minutes and the bulk of the dimethylformamide was evaporated under reduced pressure. The residue was partitioned between methylene chloride and aqueous sodium bicarbonate solution. The organic layer was dried and evaporated, at the end azeotropically with xylene. The residue was chromatographed over 30 g of silica gel using tetrahydrofuran/hexane 4:1 for elution. The combined clean fractions were evaporated and the resin obtained was crystallized from ethanol to give colorless crystals of 1-{3-[4-(2-chlorophenyl)-9-methyl-6H-thieno[3,2.f][1,2,4]triazolo[4,3-a][1,4]diazepin-2-yl]-2-propynyl}-3-methyl-2,4(1H,3H)-quinazolinedione with m.p. 167°–170°. These crystals contained 0.5 molar amounts of water according to analytical and spectral data.

EXAMPLE 79

5-{3-[4-(2-Chlorophenyl)-9-methyl-6H-thieno[3,2-f][1,2,4]triazolo4,3-a][1,4]diazepin-2-yl]-2-propynyl]-5H-dibenz[-b,e]azeoine-6,11-dione The title compound was obtained by coupling 4-(2-chlorophenyl)-2-iodo-9-methyl-6H-thieno[3,2-f][1,2,4]triazolo[4,3-a][1,4]diazepine with 5-(2-propynyl)-5H-dibenz[b,e]azepine-6,11-dione under the conditions described in EXAMPLE 37. The product was purified by chromatography over the 50-fold amount of silica gel using tetrahydrofuran/hexane 4:1 for elution. The resin left after evaporation of the combined clean fractions was crystallized from ethyl acetate to give colorless crystals of 5-{3-[4-(2-chlorophenyl)-9-methyl.6H. thieno[3,2-f][1,2,4]triazolo[4,3-a][1,4]diazepin-2 yl]-2-propynyl }-5H-dibenz[b,e]azepine-6,11-dione with m.p. 245°–247°. These crystals contained 0.33 molar amounts of ethyl acetate according the analytical and spectral data.

The acetylenic starting material was prepared as described in Example 80 below.

EXAMPLE 80

5-(2-propynyl)-5H-dibenz[b.e]azepine-6,11-dione potassium tert.-butoxide, 2.5 g, was added to a suspension of 4.5 g of 5H-dibenz[b,e]azepine-6,11-dione in 50 ml of dimethylformamide. After stirring under nitrogen for 30 minutes, 2 ml of propargyl bromide was added and stirring was continued for I hour at room temperature. The reaction mixture was acidified with acetic acid and diluted with water. The precipitate was filtered off and sucked dry. The solids were dissolved in methylene chloride. The solution was dried and evaporated and the residue was chromatographed over 120 g of silica gel using methylene chloride. The combined clean fractions containing product were evaporated and the residue was crystallized from ether/hexane to give colorless crystals of 5-(2-propynyl)-5H-dibenz[b,e]azepine-6,11-dione with m.p. 117°–118°.

EXAMPLE 81

6-Chloro-4-{3-[4-(2-chlorophenyl)-9-methyl-6H-thieno[3,2-f][1,2,4]triazolo[4,3-a][1,4]diazepin-2-yl]-2-oropynyl}-2H-1,4-benzoxazin-3-(4H)-one The title compound was prepared by coupling 4-(2-chlorophenyl)-2-iodo-9-methyl-6H-thieno [3,2-f][1,2,4]triazolo[4,3-a][1,4]diazepine with 6-chloro4-(2-propynyl)-2H-1,4-benzoxazin 3(4H)-one [ref. p. Rao et al. Indian J. Chem. 24 B, 1120 (1985)]as described in Example 37 but the reaction time was extended to 72 hours. The product was isolated by chromatography over the 100 -fold amount of silica gel (Merck 230–400 mesh) using 10% (v/v) of ethanol in methylene chloride. Crystallization of the residue obtained after evaporation of the combined clean fractions from ethyl acetate gave colorless crystals of 6-chloro-4-{3-[4-(2-chlorophenyl)-9-methyl-6H-thieno[3,2-f][1,2,4]triazolo[4,3 a][1,4]diazepin-2-yl]-2-propynyl}-2H-1,4-benzoxazin-3(4H)-one with m.p. 202°–205°.

EXAMPLE 82

1-{3-[4-(2-Chlorophenyl)-9-methyl-6H-thieno[3,2-f][1,2,4]triazolo[4,3-a][1,4]diazepin-2-yl]-2-propynyl}-2H-3,1-benzoxazin-2-one The title compound was prepared by reacting 4-(2-chlorophenyl)-2-iodo-9-methyl-6H-thieno[3,2-f][1,2,4]triazolo[4,3-a][1,4]diazepine with 1,4-dihydro-1-(2-propynyl)-3,2-benzoxazin 2-one under the conditions described in Example 37. The product was isolated by chromatography over the 50-fold amount of silica gel using 5% (v/v) of ethanol in methylene chloride and further purified by rechromatography over the 30-fold amount of silica gel using tetrahydrofuran/hexane 4:1 for elution. The clean fractions were evaporated and the residue was crystallized from methanol/ethyl acetate to give off-white crystals of 1-{3-[4-(2-chlorophenyl)-9-methyl-6H-thieno[3,2-f][1,2,4]triazolo[4,3-a][1,4]diazepin-2-yl]-2-propynyl}-2H-3,2-benzoxazin-2-one with m.p. 173°–176°. These crystals contained 0.33 molar amounts of water, according to the analytical data.

The required acetylene was synthesized as described in Example 83.

EXAMPLE 83

1,4-Dihydro-1-(2-propynyl)-3.1-benzoxazin-2-one potassium tert.-butoxide, 3.9 g (34.6 mmol) was added to a solution of 4.7 g (31 mmol) of 1,4-dihydro 3,2-benzoxazin-2-one in 30 ml of dimethylformamide. After stirring for 15 minutes under nitrogen, 4.1 g or 3.1 ml of propargyl bromide was added and stirring at room temperature was continued for 30 minutes. The reaction mixture was diluted with saturated aqueous sodium bicarbonate solution and the precipitated product was filtered off, washed with water and sucked dry. The residue was dissolved in methylene chloride and the solution was passed over a plug of silica gel.

The filtrate was evaporated and the residue was crystallized from methanol to give colorless crystals of 1,4-dihydro-1-(2-propynyl)-3,2-benzoxazin-2-one with m.p. 123°–125°.

EXAMPLE 84

4-(2-Chlorophenyl)-9-methyl-2-[2-(2-pyridinyl)ethynyl]-6H-thieno[-3,2-f][1,2,4]triazolo[4,3-a][1,4]diazepine The title compound was obtained by coupling 4-(2-chlorophenyl)-2-iodo-9-methyl-6H-thieno [3,2-f][1,2,4]triazolo[4,3-a][1,4]diazepine with 2-ethynylpyridine under the conditions used in Example 37. The product was isolated by chromatography over the 50-fold amount of silica gel using 5% (v/v) of ethanol in methylene chloride. The fractions homogenous by TLC were combined and evaporated. Crystallization of the residue from ethyl acetate and recrystallization from tetrahydrofuran/methanol gave off-white crystals of 4-(2-chlorophenyl)-9-methyl-2-[2-(2-pyridinyl)-ethynyl]-6H-thieno[3,2-f][1,2,4]triazolo[4,3-a][1,4]diazepine with m.p. 153°–155°.

EXAMPLE 85

2-{3-[4-(2-Chlorophenyl)-9-methyl-6H-thieno[3,2-f][1,2,4]triazolo[4,3-a][1,4]diazepin-2-yl]-2-propynyl}-1(2H)-isoquinolinone The title compound was prepared by coupling 4-(2-chlorophenyl)-2-iodo-9-methyl-6H-thieno[3,2-f][1,2,4]triazolo[4,3-a][1,4]diazepine with 2-(2-propynyl)-1(2H)-isoquinolinone under the conditions described in Example 37. The product was isolated by chromatography over the 50-fold amount of silica gel using tetrahydrofuran/hexane 4:1. The fractions clean by TLC were combined and evaporated and the residue was crystallized from ethanol/ethyl acetate to give colorless crystals of 2-{3-[4-(2-chlorophenyl)-9-methyl-6H-thieno[3,2-f][1,2,4]triazolo[4,3-a][1,4]diazepin-2-yl]-2-propynyl}-1(2H)isoquinolinone with m.p. 148°–150°. These crystals contained according to analytical data 0.66 molar amounts of water. The synthesis of the required acetylene is shown in Example 86.

EXAMPLE 86

2-(2-prooynyl)-1(2H)-isoquinolinone

A solution of 1 g (7 mmol) of isocarbostyril in 40 ml of dimethylformamide was treated with 0.86 g (7.7 mmol) of potassium-tert.-butoxide. After stirring under nitrogen for 30 minutes, 0.7 ml of propargyl bromide was added and stirring at room temperature was continued for 1 hour. The reaction mixture was acidified with acetic acid and diluted with water. The precipitated product was filtered off, washed with water and sucked dry. The residue was purified by chromatography over 30 g of silica gel using 5% (v/v) of ethanol in methylene chloride and crystallization from ether to give colorless crystals of 2-(2-propynyl)-1(2H)-isoquinolinone with m.p. 104°–105°. contains about. 0.125 molar amounts of $H_2O$.

EXAMPLE 87

1-{3-[4-(2-Chlorophenyl)-9-methyl-6H-thieno[3,2-f][1,2,4]triazolo[4,3-a](1,4)diazepin-2-yl]-2-propynyl)-1,3-dihydro-3-phenyl-2H-benzimidazol-2-one The title compound was prepared by reacting 4-(2-chlorophenyl)-2-iodo-9-methyl-6H-thieno-[3,2-f][1,2,4]triazolo[4,3-a][1,4]diazepine with 1,3-dihydro-1-phenyl 3-(2-propynyl)-2H-benzimidazol-2-one under the conditions used in Example 37. The product was isolated by chromatography over the 50-fold amount of silica gel using 5% (v/v) of ethanol in methylene chloride. The clean fractions were combined and evaporated and the residue was crystallized from methanol/ethyl acetate and recrystallized from methanol to yield off white crystals of 1-{3-[4-(2-chlorophenyl)-9-methyl-6H thieno [3,2-f][1,2,4]triazolo[4,3-a][1,4]diazepin-2-yl]-2-propynyl }-1,3-dihydro-3-phenyl-2H-benzimidazol-2-one with m.p.176°–179°. These crystals contained 0.66 mol of water according the analytical data.

The required propargyl derivative was synthesized as described in Example 88.

EXAMPLE 88

1,3-Dihydro 1-phenyl-3-(2-propynyl)-2H-benzimidazol-2-one

Potassium tert.-butoxide. 1.76 g (15.7 mmol) was added to a solution of 3 g (14.2 mmol) of 1.3-dihydro-1-phenyl 2H. benzimidazol-2-one in 30 ml of dimethylformamide and the mixture was stirred under nitrogen for 15 minutes. propargyl bromide, 1.4 ml (15 mmol) was then added and stirring was continued for 30 minutes at room temperature and 15 minutes on the steam bath. The product was precipitated by dilution with saturated aqueous sodium bicarbonate solution and was filtered off, washed with water and sucked dry. It was dissolved in methylene chloride and the solution was passed over a plug of silica gel using methylene chloride. The filtrate was evaporated and the residue was crystallized from methylene chloride/ethyl acetate to give colorless crystals of 1.3-dihydro-1-phenyl-3-(2-propynyl)-2H-benzimidazol-2 one with m.p. 145°–147°.

EXAMPLE 89

1-{3-[4-(2-Chloroohenyl)-9-methyl-6H-thieno[3,2-f][1,2,4]triazolo[4,3-a][1,4]diazepin-2-yl]-2-propynyl-6.s-dichloro3,4-dihydro-2(1H)-quinoline The title compound was synthesized by coupling 4-(2-chlorophenyl)-2-iodo-9-methyl-6H-thieno-[3,2-f][1,2,4]triazolo[4,3-a][1,4]diazepine with 6,8-dichloro-3,4 dihydro-1-(2-propynyl)-2(1H)-quinolinone under the conditions used in Example 37. The product was purified by chromatography over the 50-fold amount of silica gel using tetrahydrofuran/hexane 4:1. The fractions homogenous by TLC were combined and evaporated. The residue was crystallized from ethyl acetate to give colorless crystals of 1-[3-[4-(2-chloromethyl(-9-methyl-6H-thieno[3,2-f][1,2,4]triazolo[4,3-a]1,4]diazepin-2-yl]-2-propynyl-6,8-dichloro-3,4-dihydro 2(1H) quinolinone with m.p 163°–165°.

The required propargyl derivative was prepared as shown in Example 90.

EXAMPLE 90

6,8-Dichloro-3,4-dihydro-1-(2-propynyl)-2(1H)-quinolinone

A mixture of 1.5 g of 6,8-dichloro-3,4-dihydro.2(1H) quinolinone, 1.3 g of barium oxide, 40 ml of dimethylformamide and 0.8 ml of propargyl bromide was heated on the steam bath for 45 minutes and was stirred for an additional hours without heating. The product was precipitated by addit1on of ice and water and was collected by filtration. The solids were dissolved in methylene chloride and the solution was dried and evaporated. The residue was crystallized from ether/hexane to give colorless crystals of 6,8-dichloro-3,4-dihydro-1 (2-propynyl)-2(1H)-quinolinone with m.p. 92°–95°.

The starting material was obtained as follows:

A solution of 6 g of 3,4-dihydro-2(1H)-quinolinone in 50 ml of formic acid and 50 ml of conc. hydrochloric acid was added to 75 ml of 1,2-dichloroethane which had been saturated with chlorine. The mixture was stirred over ice for 30 minutes. Chlorine was introduced for 5 minutes and stirring in the cold was continued for 2 hours. It was then poured onto ice, was made basic with ammonium hydroxide and was extracted with methylene chloride. The extracts were dried and evaporated and the residue was chromatographed over 300 g of silica gel using 8% (v/v) of ethyl acetate in methylene chloride. Crystallization of the combined clean fractions from ether gave colorless crystals of 6,8-dichloro-3,4-dihydro-2(1H) quinolinone with m.p. 145°–146°.

EXAMPLE 91

2-[3-[4-(2-Chlorophenyl)-9-methyl-6H-thieno[3,2-f][1,2,4]triazolo[4,3-a][1,4]diazepin-2-yl]-2-propynyl]-3 4-dihydro1(2H)-isoquinolinone The title compound was synthesized by coupling 4-(2-chlorophenyl)-2-iodo-9-methyl-6H-thieno-[3,2-f][1,2,4]triazolo[4,3-a][1,4]diazepine with 3,4-dihydro-2.(2-propynyl)1(2H)-isoquinolinone [ref. W. Schneider et al. Arch. pharm., 291, 560 (1958)]under the conditions described in EXAMPLE 37. The product was isolated by chromatography over the 50-fold amount of solica gel using tetrahydrofuran/hexane 4:1 for elution. The clean fractions were combined and evaporated and the residue was crystallized from ethyl acetate to give colorless crystals of 2-{3-[4-(2-chlorophenyl) 9 methyl-6H-thieno[3,2-f][1,2,4]triazolo[4,3-a][1,4]diazepin-2.yl]-2-propynyl}-3,4-dihydro-1(2H)-isoquinolinone with m.p. 164°–166°.

EXAMPLE 92

4-{3-[4-(2-Chlorophenyl)-9-methyl-6H-thieno[3,2-f][1,2,4]triazolo[4,3-a][1,4]diazepin-2-v11–2-propynyl]-7-fluoro-2H-1,4-benzoxazin-3(4H)-one The title compound was prepared by reacting 4-(2-chlorophenyl)-2-iodo-9-methyl-6H-thieno-[3,2-f][1,2,4]triazolo[4,3-a][1,4]diazepine with 7-fluoro-4-(2-propynyl)-2H-1,4-benzoxazin-3(4H)-one under the conditions used in Example 37. The product was isolated by chromatography over the 50 fold amount of silica gel using 4 % (v/v) of ethanol in methylene chloride. The good fractions were combined and evaporated and the residue was crystallized from ethyl acetate to give colorless crystals of 4-{3-[4-(2-chlorophenyl)-9-methyl-6H-thieno[3,2-f][1,2,4]triazolo[4,3-a][1,4]diazepin.2.2-propynyl}-7-fluoro-2H-1,4-benzoxazin-3(4H)-one with m.p. 215°–217°.

The preparation of the required propargyl compound is shown in Example 93.

EXAMPLE 93

7-Fluoro-4-(2-propynyl)-2H-1,4-benzoxazin-3(4H)-one

A mixture of 1.7 g of 7-fluoro-2,4-dihydro.1,4-benzoxazin-3-one., 2 g of barium oxide. 1.3 ml of propargyl bromide and 40 ml of dimethyl formamide was heated on the steam bath for 45 minutes. The cooled reaction mixture was diluted with water and the precipitated product was collected by filtration. The precipitate was dissolved in methylene chloride and the solution was washed with water, dried and evaporated.

The residue was crystallized from ether/hexane to give colorless crystals of 7-fluoro-4-(2-propynyl)-2H-1,4-benzoxazin-3(4H)-one with m.p. 98°–100°.

EXAMPLE 94

4-(2-Chloroohenyl)-2–3-(1,2,3,4-tetrahydro-9H-carbazol-9-yl)-1propynyl]-9-methyl-6H-thieno-[3,2-f][1,2,4]triazolo[4,3-a][1,4]diazepine The title compound was obtained by coupling 4-(2-chlorophenyl)-2-iodo-9-methyl-6H-thieno-[3,2-f][1,2,4]triazolo[4,3-a][1,4]diazepine with 1,2,3,4-tetrahydro-9(2-propynyl)-9H-carbazole under the conditions used in Example 37. The product was isolated by chromatography over the 50-fold amount of silica gel using 8 % (v/v) of ethanol in methylene chloride for elution. The residue obtained after evaporation of the combined clean fractions containing product was crystallized from ethanol to give colorless crystals of 4-(2-chlorophenyl)-2-[3-(1,2,3,4-tetrahydro 9H-carbazol-9-yl)-1-propynyl]-9-methyl-6H-thieno-[3,2-f][1,2,4]triazolo[4,3-a][1,4]diazepine with m.p. 164°–166°. These crystals contained 0.66 molar amounts of ethanol according to analytical and spectral data.

The required propargyl compound was synthesized as shown in Example 95.

EXAMPLE 95

1,2,3,4-Tetrahydro-9-(2-propynyl)-9H-carbazole

Potassium tert.-buroxide, 3.6 g (33 mmol), was added to a solution of 5 g (30 mmol) of 1,2,3,4-tetrahydro-9H-carbazole in 50 ml of dimethylformamide. After stirring for 45 minutes under nitrogen, 3.9 g or 2.9 ml (33 mmol) of propargyl bromide was added and stirring was continued for 30 minutes at room temperature followed by 45 minutes on the steam bath. The cooled reaction mixture was diluted with water and the product was extracted with ether. The extracts were washed with water, dried over sodium sulfate and evaporated. The residue was passed over a plug of silica gel using methylene chloride/hexane 1:1. The fractions containing the least polar product were combined and evaporated. The residue was crystallized from hexane to give colorless crystals of 1,2,3,4-tetrahydro-9-(2-propynyl)-9H-carbazole with m.p. 74°-76°.

EXAMPLE 96

10-{3-[4-(2-Chloroohenyl)-9-methyl-6H-thieno[3,2-f][1,2,4]triazolo[4,3-a][1,4]diazeoin-2-yl]-2-propynyl]-9(10H)acridinone A mixture of 0.88 g (2 mmol) of 4-(2-chlorophenyl) 2-iodo-9-methyl-6H-thieno[3,2-f][1,2,4]triazolo[4,3 a][1,4]diazepine, 0.6 g (2.6 mmol) of 10-(2-propynyl)-9(10H) -acridinone [ref.A. R. Katritzky et al. J. Org. Chem. 50, 852 (1985)], 80 mg of triphenylphosphine, 20 mg of cuprous iodide, 5.6 ml of triethylamine and 50 ml of dimethylformamide was degassed with argon for 10 minutes. Palladium acetate, 25 mg. was then added and the mixture was heated to 80°-90° for 30 minutes. The product was precipitated by addition of saturated agueous sodium bicarbonate solution and was collected by filtration. The solids were dissolved in methylene chloride and the solution was dried and evaporated. The residue was chromatographed over 50 g of silica gel using 5% (v/v) of ethanol in methylene chloride for elution. The combined clean fractions were evaporated and the residue was crystallized from ethanol to yield yellow crystals of 10-{3-[4-(2-chlorophenyl)-9-methyl-6H-thieno[3,2-f][1,2,4]triazolo[4,3 a][1,4]diazepin-2-yl]-2-propynyl}-9(10H)-acridinone with m.p. 175°-180° with foaming. These crystals contained molar equivalents of water.

EXAMPLE 97

3,8-Dichloro-5-{3-[4-(2-chlorophenyl)-9-methyl-6H-thieno[3,2-f]1,2,4]triazolo[4,3-a][1,4]diazepin-2-yl]-2-propynyl}-6(5H)phenanthridinone The title compound was prepared by reacting 4-(2-chlorophenyl)-2-iodo-9-methyl-6H-thieno[3,2-f]1,2,4]triazolo[4,3-a][1,4]diazepine with 3.8-dichloro 5-(2-propynyl)-6(5H)-phenanthridinone under the conditions used in Example 37, but at the end, the reaction mixture was heated for minutes at 90°-95°. The product was isolated by chromatography over the 50-fold amount of silica gel using tetrahydrofuran/hexane 4:1 for elution. Crystallization of the combined clean fractions from tetrahydrofuran/ethyl acetate gave colorless crystals of 3,8-dichloro-5-{3-[4-(2-chlorophenyl)-9-methyl-6H-thieno[3,2-f][1,2,4]triazolo[4,3-a]1,4]diazepin-2-yl]-2-propynyl}-6(5H)-phenanthridinone with m.p. 218°-220°.

The propargyl derivative used for this experiment was prepared as shown in Example 98.

EXAMPLE 98

3,8-Dichloro-5-(2-propynyl)-6(5H)-phenanthridinone

A mixture of 5 g (19 mmol) of 3,8-dichloro-6(5H)phenanthridinone, 3,2 g (21 mmol) of barium oxide and 1.9 ml (21 mmol) of propargyl bromide in 40 ml of dimethylformamide was heated on the steam bath for 1 hour. After cooling, the product was precipitated by addition of water, filtered off and washed with water. It was dissolved in methylene chloride and the solution was dried and evaporated. The residue was chromatographed over 150 g of silica gel using 10% (v/v) of hexane in methylene chloride. The fractions containing the product were combined and evaporated. The solid residue was recrystallized from ethanol to give colorless crystals of 3,8-dichloro-5-(2-propynyl)-6(5H)-phenanthridinone with m.p. 248°-250°.

EXAMPLE 99

4-(2-Chlorophenyl)-9-methyl-2-(phenylethynyl)-6H-thieno[3,2-f][1,2,4]triazolo[4,3-a1[1,4]-diazepine The title compound was obtained by reacting 4-(2-chlorophenyl)-2-iodo-9-methyl-6H-thieno[3,2-f][1,2,4]triazolo[4,3-a][1,4]diazepine with phenylacetylene under the conditions described in EXAMPLE 37. The product was isolated by chromatography over the 50-fold amount of silica gel using 5% (v/v) of ethanol in methylene chloride for elution. The combined clean fractions were evaporated and the residue was crystallized from ethyl acetate to give colorless crystals of 4-(2-chlorophenyl)-9-methyl-2-(phenylethynyl)-6H-thieno[3,2-f][1,2,4]triazolo[4,3-a][1,4]-diazepine with m.p. 215°-217°.

EXAMPLE 100

1-[-{3-[6-(2-Fluorophenyl)-1-methyl-4H-[1,2,4]triazolo[4,3-a][1,4]}benzodiazepin-8-yl]-2-propynyl}-3,4-dihydro-2(1H)quinolinone A mixture of 0.84 g (2 mmol) of 6-(2-fluorophenyl)-8-iodo-1-methyl-4H-[1,2,4]triazolo[4,3-a][1,4]benzodiazepine, 0.48 g (2.6 mmol) of 3,4-dihydro-1-(2-propynyl)-2(1H)quinolinone, 80 mg of triphenylphosphine, 20 mg of cuprous iodide, 1.5 ml of triethylamine and 50 ml of dimethylformamide was deqassed with argon for 10 minutes. Palladium acetate, 25 mg, was then added and stirring was continued for 18 hours. The solvent was evaporated under reduced pressure and the residue was partitioned between methylene chloride and saturated aqueous sodium bicarbonate solution. The organic layer was separated. dried and evaporated and the residue was chromatographed over 50 g of silica gel using 5% (v/v) of ethanol in methylene chloride for elution. Crystallization of the combined clean fractions from ethyl acetate gave colorless crystals of 1-{3-[6-(2-fluorophenyl)-1-methyl-4H-[1,2,4]triazolo[4,3-a][1,4]benzodiazepin 8-yl]-2-propynyl}3,4 dihydro-2(1H)-quinolinone with m.p. 236°-239°.

EXAMPLE 101

6-(2-Fluorophenyl)-1-methyl-8-(4-phenyl-1-butvnyl)-4H-[1,2,4]triazolo4,3-a][1,4]benzodiazepine The title compound was obtained by reacting 6-(2-fluorophenyl)-8-iodo-1-methyl-4H-[1,2,4]triazolo[4,3 a][1,4]benzodiazepine with 4-phenyl-1-butyne under the conditions used in Example 9. The product was isolated by chromatography over the 40-fold amount of silica gel using 5% (v/v) of ethanol in methylene chloride for elution. The combined clean fractions were evaporated and the residue was crystallized from ethyl acetate with dry-ice cooling and was recrystallized from ethyl acetate/ether/hexane to give colorless crystals of 6-(2-fluorophenyl)-1-methyl-8-(4-phenyl-1-butynyl).4H [1,2,4]triazolo[4,3-a][1,4]benzodiazepine with m.p. 125°–128°.

EXAMPLE 102

2-{3-[6-(2-Fluorophenyl)-1-(trifluoromethyl)-4H-1,2,4]triazolo[4,3-a][1,4]benzodiazepin-8-yl]-2-propynyl]-1H-isoindole-1,3(2H)-dione A mixture of 0.94 g (2 mmol) of 6-(2-fluorophenyl) 8-iodo-1-(trifluoromethyl)-4H-[1,2,4]triazolo [4,3-a][1,4]-benzodiazepine, 0.55 g (3 mmol) of N-propargylphthalimide 80 mg of triphenylphosphine, 20 mg of cuprous iodide, 0.6 ml of triethylamine and 50 ml of dimethylformamide was degassed with argon for 10 minutes. Palladium acetate, 25 mg. was then added and the mixture was stirred for 3 days at room temperature. The product was precipitated by dilution with sodium bicarbonate solution and was collected by filtration. It was dissolved in methylene chloride and the solution was washed with bicarbonate solution, dried and evaporated. The residue was chromatographed over 40 g of silica gel using 5% (v/v) of ethanol in methylene chloride. The combined good fractions were evaporated and the residue was crystallized from ethyl acetate to give colorless crystals of 2-{3-[6-(2-fluorophenyl)-1-(trifluoromethyl)-4H-[1,2,4]triazolo[4,3-a][4,1]benzodiazepin-8-yl]-2-ProPynyl}-1H-isoindole-1,3(2H)-dione with m.p. 204°–206°.

The starting material was prepared as described in Example 103.

EXAMPLE 103

6-(2-Fluorophenyl)-1-(trifluoromethyl)-8-iodo-4H-[1,2,4]triazolo [4,3-a][1,4]benzodiazepine A mixture of 5 g of 5-(2-fluorophenyl)-2-hydrazino-7.iodo3H-4,1-benzodiazepine, 20 ml of trifluoroacetic acid, 5 ml of trifluoroacetic anhydride and 100 ml of methylene chloride was heated on the steam bath under a stream of nitrogen to distill off the methylene chloride. Toluene, 100 ml, was then added and heating on the steam bath was continued for 30 minutes. The mixture was partitioned between methylene chloride and saturated aqueous sodium bicarbonate solution. The organic phase was separated, dried and evaporated. The residue was crystallized from ether and recrystallized from ethanol to yield colorless crystals of 6-(2-fluorophenyl)-1-(trifluoromethyl)-8-iodo-4H-[1,2,4]triazolo[4,3-a][4,1]benzo. diazepine with m.p. 202°–204°.

EXAMPLE 104

(S)-1-{3-[6-(2-Fluorophenyl)-1,4-dimethyl-4H-1,2,4]triazolo [4,3-a][1,4]benzodiazepin-8-yl]-2-propynyl}-3,4-dihydro-2(1H)quinolinone The title compound was prepared by coupling (S)-6-(2-fluorophenyl)-8-iodo-4,1-dimethyl-4H[1,2,4]triazolo[4,3-a][4,1]benzodiazepine with 3,4-dihydro-1-(2-propynyl)-2(1H)-quinolinone under the conditions used in Example 100. The product was isolated by chromatography over the 50-fold amount of silica gel using 5% (v/v) of ethanol in methylene chloride for elution. The combined clean fractions were evaporated and the residue crystallized very slowly from ethanol/ether to give colorless crystals of (S)-1-{3-[6-(2-fluorophenyl)-4,1-dimethyl4H-[1,2,4]-triazolo[4,3-a][4,1]benzodiazepin-8-yl]-2-propynyl}3,4-dihydro-2(1H)-quinolinone with m.p. 155°–160° with foaming. These crystals contained both ethanol and water according analytical and spectral data. $[\alpha]D = +87.5°$ (c=1.0091 in $CH_2Cl_2$)

The starting material was obtained as described in Example 105.

EXAMPLE 105

(S)-6-(2-Fluorophenyl)-8-iodo-1,4-dimethyl-4H-[1.2.4]triazolo [4,3-a][1,4]benzodiazeoine A solution of 2 g (5.07 mmol) of (S)-5-(2-fluorophenyl)-1,1,3-dihydro-7-iodo-3-methyl-2H-4,1-benzodiazepin-2-one in 60 ml of tetrahydrofuran was cooled to $-30°$ and 0.57 g (5.7 mmol) of potassium tert.-butoxide was added. The mixture was stirred under nitrogen for 30 minutes while the temperature was allowed to climb to 5°. Diethyl chlorophosphate, 1.03 g (6.5 mmol), was added and stirring was continued for 30 minutes without cooling. After addition of 0.54 g (7.2 mmol) of acetyl hydrazide the mixture was stirred for another 30 minutes at room temperature. Butanol, 75 ml, was then added and the tetrahydrofuran was distilled out. A few drops of acetic acid were added and part of the butanol was distilled over as well. The reaction mixture was evaporated under reduced pressure and the residue was partitioned between methylene chloride and saturated aqueous sodium bicarbonate solution. The orqanic layer was separated. dried and eVaporated and the residue was chromatographed over silica gel using 5% (v/v) of ethanol in methylene chloride for elution. Crystallization of the material obtained from the combined clean fractions from ethyl acetate/-hexane gave colorless crystals of (S)-6-(2-fluorophenyl)-8-iodo-1,4-dimethyl-4H-[1,2,4]triazolo[4,3-a][1.4]benzodiazepine with m.p. 142°–145°. $[\alpha]D = =50.38°$ (c=0.9964 in $CH_2Cl_2$)

The starting material required for this experiment was prepared as shown in Example 106.

EXAMPLE 106

(S)-2-(2-Fluorophenyl)-1,3-dihydro-7-iodo-3-methyl-2H-1,4-benzodiazeoin-2-one

A mixture of 11 g of (S)-{2-[2-(2-fluorobenzoyl)-4iodophenyl]-amino}-1-methyl-2-oxoethyl-carbamic acid phenylmethyl ester and 30 ml of acetic acid containing 30 % of hydrogen bromide was stirred at room temperature for 3 hours. The reaction mixture was partitioned between water and ether. The aqueous phase was washed with ether and made alkaline by addition of ice and ammonia. The precipitated material was extracted with methylene chloride and the extracts were dried and evaporated. The residue was heated in 50 ml of ethanol containing 5 ml of acetic acid on the steam bath for 15 minutes. The solvent was evaporated under reduced pressure and the residue was partitioned between methylene chloride and 10% aqueous sodium carbonate solution. The orqanic phase was dried and evaporated and the residue was crystallized from ethyl acetate and recrystallized from methylene chloride- /ethyl acetate to yield colorless crystals of (S)-2-(2-fluorophenyl)-1,3-dihydro-7-iodo-3-methyl-2H-4,1-benzodiazepin-2-one with m.p. 223°–225°. [α]D = +100.79° (c=0.9891 in CH2Cl2)

The starting material for this experiment was obtained as shown in Example 107.

EXAMPLE 107

(S)-{2-[2-(2-Fluorobenzoyl-4-iodophenyl]amino}-1-methyl-2oxoethylcarbamic acid ohenYlmethyl ester A solution of 2.9 g (13 mmol) of N-benzyloxycarbonyl. L-alanine in 15 ml of tetrahydrofuran was cooled to −40°. phophorus pentachloride, 2.7 g (13 mmol). was added and the mixture was stirred for 30 minutes at −30°. A solution of 3.41 g (10 mmol) of 2-(2-fluorobenzoyl)-4-iodoaniline in 50 ml of methylene chloride was then added and stirring was continued for 15 minutes at 0°–10°. After addition of 10% aqueous sodium carbonate solution, the two-phase mixture was stirred at this temperature for 30 minutes. It was then extracted with ether. The extracts were washed with sodium carbonate solution and water, were dried and evaporated. The residue was passed over a plug of silica gel with methylene chloride. The filtrate was evaporated and the residue was crystallized from ethanol to give colorless crystals of (S)-{2-[2-(2-fluorobenzoyl-4iodophenyl]-amino}-1-methyl-2-oxoethylcarbamic acid phenylmethyl ester with m.p. 159°–161°. [α]D = −10.35° (c=0.985 in CH2Cl2)

EXAMPLE 108 rac-4-(2-Chlorophenyl)-2-iodo-6.9-dimethyl-6H-thieno[3.2-f][1,2,4]triazolo[4,3-a][1.41-diazepine A mixture of 2.08 g (5 mmol) of (S)-5-(2-chlorophenyl)-1,3-dihydro-7-iodo-3-methyl-2H-thieno-[2.3-e][4,1]diazepin2-one, 1,25 g of phosphorus pentasulfide, 1.3 g of sodium bicarbonate and 40 ml if diglyme was stirred under nitrogen at 80°–90° for 6 hours. Water and ice were added and the mixture was stirred for 15 minutes. The solids were filtered off, washed with water and sucked dry. The resulting thione was further dried under vacuum at 50° to leave 2.6 g of crude material which was further reacted as follows:

The crude thione was stirred with 1.3 ml of anhydrous hydrazine in 30 ml of tetrahydrofuran for 30 minutes at room temperature. The solvent was evaporated under reduced pressure and the residue was stirred with 15 ml of water and 15 ml of methylene chloride. The crystalline hydrazine derivative was collected by filtration, washed with water and ether and was added to 13 ml of ethyl acetate and 6.5 ml of triethylorthoacetate. This mixture was heated on the steam bath for 30 minutes and the crystals formed were filtered off after cooling. The product was recrystallized from methylene chloride/methanol to give colorless crystals of rac-4-(2-chlorophenyl)-2-iodo-6,9-dimethyl-6H-thieno[3,2-f][1,2,4]triazolo[4,3-a][4,1]-diazepine with m.p. 262°–264°. These crystals had no rotation, indicating total racemization had occurred.

The starting material used in this experiment was prepared as described in Example 109.

Examole 10

(S)-5-(2-Chlorophenyl)-1,3-dihydro-7-iodo-3-methyl-2H-thieno-2,3-e][4]diazepin-2-one A mixture of 7.7 g (26.5 mmol) of (S)-5-(2-chlorophenyl)-1,3-dihydro-3-methyl-2H-thieno[2,3-e][4,1]diazepin-2.one, 60 ml of methanol 60 ml of acetic acid 8.61 q (53 mmol) of iodine monochloride and 2.17 g (26.5 mmol) of sodium acetate was stirred at ambient temperature for 15 minutes. A solution of 9 g of sodium bisulfite in water was added to reduce the excess reagent. The reaction mixture was made alkaline by addition of ice and ammonium hydroxide. The precipitated material was collected, washed with water and sucked dry. It was recrystallized from methanol/ethyl acetate to give colorless crystals of (S)-5-(2-chlorophenyl)-1,3-dihydro-7 iodo-3-methyl 2H-thieno[2,3-e][4,1]diazepin-2-one with m.p. 235°–237°.

The starting material required for this experiment was prepared as shown in Example 110.

EXAMPLE 110

(S)-5-(2-Chlorophenyl)-1.3-dihydro-3-methyl-2H-thieno[2.3-e![1,4]diazepin-2-one

A solution of 22 g of (S)-{2-[3-(2-chlorobenzoyl)-2thienyl]amino}-1-methyl-2-oxoethylcarbamic acid phenylmethyl ester in 75 ml of acetic acid containing 30% of hydrogen bromide was allowed to sit at room temperature for 3 hours. The reaction mixture was partitioned between water and ether. The aqueous phase was washed with ether and was made basic by addition of ice and ammonium hydroxide. The precipitated material was extracted with methylene chloride. The extracts were dried and evaporated and the residue was dissolved in 500 ml of toluene. After addition of 66 g of silica gel, the mixture was stirred and heated to reflux for 3 hours with separation of the water formed. The silica gel was filtered off and washed well with methanol. The filtrate was evaporated and the residue was passed over 200 g of silica gel using ethyl acetate/methylene chloride 1 1 for elution. The product crystalized from methylene chloride/hexane and was recrystallized from ether for analysis to yield (S)-5-(2-Chlorophenyl)-1,3-dihydro-3 methyl-2H-thieno[2,3-e][4,1]diazepin-2-one m.p. 200°–203°.[α]D = −0.4° (c=1.0185 in CH2Cl2)

The starting material for this experiment was prepared as described in Example 111.

EXAMPLE 111

(S)-{2-[3-(2-Chlorobenzoyl)-2-thienyl]amino-1-methyl-2oxoethylcarbamic acid phenylmethyl ester A solution of 29 g of N-benzyloxycarbonyl-L-alanine in 100 ml of tetrahydrofuran was cooled to −40°. phophorus pentachloride, 27 g, was added and stirring was continued for 30 minutes at −30°. A solution of 23.7 g (0 1 mol) of 2-amino-3-(2-chlorobenzoyl)thiophene in 400 ml of methylene chloride was added and the mixture was stirred for 15 minutes at 0°–10°. It was layered with 300 ml of 10% aqueous sodium carbonate solution and the two-phase mixture was stirred at 0°–10° for 30 minutes. After dilution with ether, the organic layer was separated, washed with sodium carbonate solution, dried and evaporated. The residue was crystallized from ethanol with seeding. Seeds were obtained by chromatographing a 2 g sample over 60 g of silica gel using 10% (v/v) ethyl acetate in methylene chloride for elution. The clean fractions yielded crystals from ether/hexane which were recrystallized from ethanol to give colorless crystals of (S)-{2-[3-(2-chloro-benzoyl)-2-thienyl]amino}-1-methyl-2-oxoethylcarbamic acid phenylmethyl ester with m.p. 133°°–135°. [α]D = −26.92° (c=0.9546 in CH2Cl2)

EXAMPLE 112

5-{3-[4-(2-Chlorophenyl)-9-methyl-6H-thieno[3,2-f][1,2,4]triazolo[4,3-a][1,4]diazeoin-5-oxide-2-yl]-2-propynyl}-6(5H)phenanthridinone A mixture of 1.1 g (2 mmol) of 5-{3-[4-(2-chlorophenyl)-9-methyl-6H-thieno[3,2-f][1,2,4]triazolo[4,3-a][4,1]diazepin-2yl]-2-propynyl}-6(5H)-phenanthridinone and 0.68 g of m-chloroperoxybenzoic acid in 100 ml of methylene chloride was allowed to sit at room temperature for 20 hours. The solution was washed with 10% aqueous sodium carbonate solution, was dried and evaporated. The residue was crystallized from methanol/ethyl acetate to give off-white crystals of 5-{3-[4-(2-chlorophenyl)-9-methyl-6H-thieno[3,2-f][1,2,4]triazolo[4,3-a][4,1]diazepin-5-oxide-2-yl]-2-propynyl}-6(5H)ph ®nanthridinone with m.p. 260°–270° with decomposition. It was recrystallized for analysis from tetrahydrofuran/methanol/ ethyl acetate.

The title compound was also obtained by coupling 4-(2-chlorophenyl)-2-iodo-9-methyl-6H-thieno[2-f][1.2,4]triazolo[4,3-a][4,1]diazepine-5-oxide from Example 128 with 5-(2-propynyl)-6(5H)-phenanthridinone using the conditions described in Example 37.

EXAMPLE 113

5-{3-[6-Acetyloxy-4-(2-chlorophenyl)-9-methyl-6H-thieno[3,2-f][1.2,4]triazolo[4,3-a][1,4]diazepin-2-yl]-2-propynyl-6(5H)phenanthridinone A mixture of of 7 g of 5-{3-[4-(2-chlorophenyl)-9methyl-6H-thieno[3,2-f][1,2,4]triazolo[4,3-a][4,1]diazepin-5. oxide-2-yl]-2-propynyl}-6(5H)-phenanthridinone, 25 ml of acetic anhydride and 30 ml of pyridine was heated on the steam bath for 3 hours under argon. The reagents were removed under reduced pressure and the residue was chromatographed over 30 g of silica gel using 3 % (v/v) of ethanol in methylene chloride for elution. The clean fractions containing 5-{3-[6-acetyloxy4-(2-chlorophenyl)-9-methyl-6H-thieno[3,2-f][1,2,4]triazolo [4,3-a][4,1]diazepin-2-yl]-2-propynyl}-6(5H)phenanthridinone were combined and evaporated. The residue did not crystallize and was characterized spectroscopically only. NMR (CDCl ): 2.36 (s, 3, OAc), 2.68 (s, 3, 9-Me), 5.43 (s,2, ° —CH$_2$—), 6.78 (s, 2, C6-H and thienyl-H), 7.2–8.6 (m, 12, aromatic H).

EXAMPLE 114 rac-5-{3-[4-(2-Chlorophenyl)-6-hydroxy-9-methyl-6H-thieno-3,2-f1,2,4]triazolo[4,3-a][1,4]diazepin-2-yl]-2-propynyl]-6(5H)-phenanthridinone A solution of 0.25 g of 5-{3-[6-acetyloxy-4-(2-chlorophenyl)-9-methyl-6H-thieno[3,2-f][1,2,4]triazolo[4,3-a][1,4]diazepin-2-yl]-2-propynyl}-6(5H)-phenanthridinone in 30 ml of warm methanol was treated with 2 ml of 3N sodium hydroxide solution. After 15 minutes, the reaction mixture was acidified with acetic acid and was partitioned between methylene chloride and aqueous sodium bicarbonate solution. The organic phase was separated, dried and evaporated. The residue was chromatographed over 25 g of silica gel (Merck 230–400 mesh) using 5% (v/v) of ethanol in methylene chloride for elution. After elution of some rearranged rac-4-(2-chloro-phenyl)-4,5-dihydro-9-methyl-2-[3-(5,6-dihydro-6-oxo-5. phenanthridinyl)-1-propynyl]-6H-thieno[3 2-f][1.2,4]triazolo[4,3. a][1,4]diazepin-6-one with m.p. 225°–230° (from methanol/ethyl acetate), the fract ions containing rac-5-{3-[4-(2-chloro. phenyl)-6-hydroxy-9-methyl-6H-thieno-[3,2-f][1,2,4]triazolo. [4,3-a][4,1]diazepin-2-yl]-2-propynyl}-6(5H)-phenanthridinone were combined and evaporated. The residue was crystallized from methanol/ethyl acetate to give colorless crystals with m.p. 255°–258°.

The title compound was alternatively prepared by reacting 4-(2-chlorophenyl)-2-iodo-9-methyl-6H-thieno[3,2-f][1,2,4]triazolo[4,3-a][4,1]diazepine-6-ol from Example 130 with 5-(2-propynyl)-6(5H)-phenanthridinone under the conditions described in Example 37.

EXAMPLE 115 rac-2-{[6-(2-Fluorophenyl)-1-methyl-4H-[1,2,4]triazolo[4,3-a][1,4]benzodiazeoin-8-yl]ethynyl}-3.4-dihydro-2,5,7,8-tetramethyl-2H-1-benzopyran-6-ol The title compound was prepared by coupling 6-(2-fluoro-phenyl)-8-iodo-1-methyl-4H-[1,2,4]triazolo[4,3-a][4,1]benzodiazepine with rac-2-ethynyl-3,4-dihydro-2,5,7,8-tetramethyl-2H-1-benzopyran-6-ol [ref. H. Mayer et al., Helv. Chim. Acta, 67, 650 (1963)]under the conditions described in Example 37. The product was isolated by chromatography over the 50-fold amount of silica gel using 5% (v/v) of ethanol in methylene chloride. The clean fractions containing product were combined and evaporated. The residue was crystallized from ethanol/ethyl acetate to give colorless crystals of rac-2-{[6-(2-fluorophenyl)-1-methyl-4H-[1,2,4]triazolo[4,3-a][4,1]benzodiazepin-8-yl]ethynyl}-3,4-dihydro-2,5,7,8-tetramethyl-2H-1-benzopyran-6-ol with m.p. 265°–267°.

EXAMPLE 116 rac-2-[[4-(2-Chlorophenyl)-9-methyl-6H-thieno[3,2-f][1,2,4]triazolo[4,3-a][1,4]diazeDin-2-yl]ethynyl}-3,4-dihydro-2,5,7,8-tetramethyl-2H-1-benzopyran-6-ol The title compound was obtained by coupling 4-(2-chlorophenyl)-2-iodo-9-methyl-6H-thieno-[3,2-f][1,2,4]triazolo[4,3-a][4,1]diazepine with rac-2-ethynyl-3,4-dihydro-2,5,7,8-tetramethyl-2H-1-benzopyran-6-ol under the conditions described in Example 37. The product was isolated by chromatography over the 50-fold amount of silica gel using 5% (v/v) of ethanol in methylene chloride. The combined clean fractions were evaporated and the residue was crystallized from ethyl acetate to give colorless crystals of rac-2-{[4-(2-chlorophenyl)-9-methyl-6H-thieno[3,2-f][1,2,4]triazolo[4,3-a][4,1]diazepin-2-yl]ethynyl}-3,4-dihydro-2,5,7,8-tetramethyl-2H-1-benzopyran-6-ol with m.p. 155°–160° with foaming. These crystals contained 1.5 molar amounts of water on the basis of the analytical and spectral data.

EXAMPLE 117 rac-6-(2-Fluorophenyl)-4-hydroxy-8-iodo-1-methyl-4H-[1,2,4]triazolo[4,3-a][1,4]benzodiazepine A solution of 0.8 g of potassium tert.-butoxide in 20 ml of tetrahydrofuran and 15 ml of tert. butanol and 0.6 ml of triethylphosphite was cooled to −30° with stirring under argon. A solution of 0.8 g of 4-(2-chlorophenyl)-2-iodo-9-methyl-6H-thieno[3,2-f][1,2,4]triazolo[4,3-a][4,1]diazepine in 5 ml of dimethylformamide was added and stirring was continued for 1 hour at −20° to −10°. A stream of oxygen was introduced while the mixture was stirred for an additional hour at this temperature. The reaction mixture was acidified by addition of acetic acid and was partitioned between sodium carbonate solution and methylene chloride containing 10% (v/v) of ethanol. The organic layer was dried and evaporated and the residue was crystallized from methylene chloride/ethyl acetate and recrystallized from ethanol to give colorless crystals of rac-6-(2-fluorophenyl)-4-hydroxy-8-iodo-1-methyl-4H-[1,2,4]triazolo[4,3-a][4,1]benzodiazepine with m.p. 258°–260°.

EXAMPLE 118 rac-6-(2-Fluorophenyl)-B-iodo-4-methoxV-1-methyl-4H-[1,2,4]triazolo[4,3-a][1,4]benzodiazeoine A mixture of 0.435 g (1 mmol) of rac-6-(2-fluorophenyl)-4-hydroxy-8-iodo-1-methyl-4H-[1,2,4]triazolo[4,3-a][4,1]benzodiazepine, 3 ml of thionyl chloride and 20 ml of methylene chloride was stirred at room temperature for 2 hours. After evaporation under reduced pressure, the residue was dissolved in 20 ml of methanol and the solution was :reated with 3 ml of triethylamine. After heating on the steam bath for 5 minutes, the mixture was evaporated to dryness and the residue was partitioned between methylene chloride and aqueous sodium bicarbonate solution. The organic layer was dried and evaporated and the residue was crystallized from ethyl acetate to yield colorless crystals of rac-6-(2-fluorophenyl)-8-iodo-4-methoxy-1-methyl-4H-[1,2,4]triazolo[4,3-a][4,1]benzodiazepine with m.p. 240°–242°. The analytical sample was recrystallized from methanol/ethyl acetate and had m.p. 243°–244°.

EXAMPLE 119

1-{3-[6-(2-Fluorophenyl)-1-(trifluoromethyl)-4U-[1,2,4)triazolo[-4,3-a]1,4]benzodiazepin-8-yl]-2-propynyl}-3,4-dihydro-2(1H)-quinolinone The title compound was prepared by coupling 6-(2-fluorophenyl)-1-(trifluoromethyl)-8-iodo-4H-[1,2,4]triazolo [4,3-a][1,4]benzodiazepine with 3,4-dihydro-1-(2-propynyl)-2(1H)-quinolinone under the conditions used in Example 37. The product was purified by chromatoqraphy over the 50-fold amount of silica gel using 5% (v/v) of ethanol in methylene chloride. The clean fractions were combined and evaporated and the residue was crystallized from ethyl acetate to yield colorless crystals of 1-{3-[6-(2-fluorophenyl)-1-(trifluoromethyl)-4H-[1,2,4]triazolo[4,3-a][4,1]benzodiazepin-8-yl]-2-propynyl}-3,4-dihydro-2(1H)-quinolinone with m.p. 193°–196°.

EXAMPLE 120 rac-1-3-[6-(2-Fluorophenyl)-4-hydroxy-1-methyl-4H-[1,2,41triazolo[4,3-a][1,4]benzodiazepin-8-yl]-2-oropynyl}-3,4-dihydro-2(1H)-quinolinone The title compound was obtained by reacting rac-6-(2-fluorophenyl)-4-hydroxy-8-iodo-1-methyl-4H-[1,2,4]triazolo[4,3-a][4,1]benzodiazepine with 3,4-dihydro-1(2-propynyl)-2(1H)-quinolinone under the conditions used in Example 37. The product was isolated by chromatography over the 50-fold amount of silica gel using 5% (v/v) of ethanol in methylene chloride. The combined good fractions were evaporated and the residue was crystallized from methanol/ethyl acetate to give colorless crystals of rac-1-{3-[6-(2-fluorophenyl)-4-hydroxy-1-methyl-4H-[1,2,4]triazolo[4,3-a][4,1]benzodiazepin-8-yl]-2-propynyl}-3,4-dihydro-2(1H)-quinolinone with m.p. 253°–255° with decomposition. These crystals contained molar equivalents of water.

EXAMPLE 121 rac-1-{3-[6-(2-Fluorophenyl)-4-methoxy-1-methyl-4H-[1,2,4]triazolo4,3-a]1,4]benzodiazepin-8-yl]-2-oropynyl}-3,4-dihydro-2(1H)-quinolinone The title compound was prepared by coupling rac-6-(2-fluorophenyl)-8-iodo-4-methoxy-1-methyl-4H-[1,2,4]triazolo[4,3-a][4,1]benzodiazepine with 3,4-dihydro-1-(2-propynyl)-2(1H)-quinolinone under the conditions used in Example 37. The product was isolated by chromatography over the 50-fold amount of silica gel using 5% (v/v) of ethanol in methylene chloride for elution. The combined clean fractions were evaporated and the residue was crystallized from ethyl acetate/ether to give colorless crystals of rac-1-{3-[6-(2-fluorophenyl)-4-methoxy-1-methyl-4H[1,2,4]triazolo[4,3-a][1,4] benzodiazepin-8-yl]-2-propynyl}-3,4-dihydro-2(1H)-quinolinone with m.p. 155°–160°. These crystals contained 0.33 molar equivalents of water.

EXAMPLE 122

1-{3-[4-(2-Chlorophenyl)-9-methyl-6H-thieno[3,2-f][1,2,4]triazolo[4,3-a][1,4]diazepin-2-yl]-2-prooynyl]-spiro[cyclo-pentane-1,3′-[3H]indol]-2(1′H)-one dihydrochloride The title compound was obtained by reacting 4-(2-chlorophenyl)-2-iodo-9-methyl-6H-thieno[3.2-f][1,2,4]triazolo[4,3-a][1,4]diazepine with 1′-(2-propynyl)spiro [cyclopentane-1,3′-[3H]indol]-2′-(1′H)-one under the conditions described in Example 37. The product was isolated by chromatography over the 50-fold amount of silica gel using 5% (v/v) of ethanol in methylene chloride for elution. The combined good fractions were evaporated and the residue was converted to a crystalline dihydrochloride by treatment with excess ethanolic hydrogen chloride in ethanol/ethyl acetate. The light yellow crystals of 1-{3-[4-(2-chlorophenyl)-9-methyl-6H-thieno[3,2-f][1,2,4]triazolo[4,3-a][4,1]diazepin-2-yl]-2-propynyl} spiro[cyclopentane-1,3′-[3H]indol]-2(1′H) one dihydrochloride had m.p. 173°–176° with foaming and contained two molar equivalents of water and 0.66 molar equivalents of ethanol according to the analytical and spectral data.

The starting propargyl derivative used in this experiment was prepared as shown in Example 123.

EXAMPLE 123

1′-(2-propynyl)spiro[cyclopentane-1,3′-[3H]indol]-2′-(l′H)-one

Potassium tert.-butoxide, 0.37 g (3.3 mmol), was added to a solution of 0.56 g (3 mmol) of spiro[cyclopentane-1,3′[3H]indol]-2′-(1′H)-one [ref. R. J. Owellen, J. Org. Chem. 39, 69 (1974)]in 10 ml of dimethylformamide. The mixture was stirred for 15 minutes and 0 3 ml of propargyl bromide was added and stirring was continued for 30 minutes. The reaction mixture was then partitioned between xylene and saturated sodium bicarbonate solution. The organic phase was dried and evaporated and the residue was chromatographed over 20 g of silica gel using methylene chloride for elution. The combined clean fractions were evaporated and the residue was crystallized from ether/hexane to give colorless crystals of 1'-(2-propynyl)spiro[cyclopentane-1,3'-[3H]indol]-2'-(1'H)-one with m.p. 109°–111°.

EXAMPLE 124

1-{3-[4-(2-Chlorophenyl)-9-methyl-6H-thieno[3,2-f][1,2,4]triazolo[4,3-a][4,1]diazepin-5-oxide-2-yl)2-propynyl]-3,4-dihydro-2(1H)-quinolinone A mixture of 0.5 g (1 mmol) of 1-{3-[4-(2-chlorophenyl)-9-methyl-6H-thieno[3,2-f][1,2,4]triazolo[4,3-a][4,1]diazepin-2-yl]2-propynyl}-3,4-dihydro-2(1H)-quinolinone and 0.34 g (2 mmol) of m-chloroperoxybenzoic acid in 30 ml of methylene chloride was allowed to sit at room temperature over niqht. It was then washed with 10% aqueous sodium carbonate solution, dried and evaporated, The residue was purified by chromatography over 20 g of silica gel (230-400 mesh) using 5% (v/v) of ethanol in methylene chloride. The combined clean fractions were evaporated and the residue was crystallized from ethyl acetate and recrystallized from methanol/ethyl acetate to give colorless crystals of 1-[3-[4-(2-chlorophenyl)-9-methyl-6H-thieno[3,2-f][1,2,4]triazolo[4,3-a][1,4]diazepin-5-oxide-2-yl]2-propynyl}-3,4-dihydro-2(1H)-quinolinone with m.p. 225°–230° with decomposition. These crystals contained according to spectral and analytical data 0.166 molar amounts of ethyl acetate.

EXAMPLE 125

4-(2-Chlorophenyl)-2-iodo-9-methyl-6H-thieno3,2-f][1,2,4]triazolo[-4,3-a][1,4]diazepine A mixture of 64.4g of 5-(2-chlorophenyl)-1,3-dihydro-7-iodo-2H-thieno[2,3-e][4,1]diazepin-2-thione, 650 ml of tetrahydrofuran and 65 ml of hydrazine was stirred at room temperature for 30 minutes. The solvent was evaporated under reduced pressure and the residue was stirred with 275 ml of methylene chloride and 275 ml of water for 15 minutes. The precipitated crystalline material was filtered off and washed with water and ether. This crude 5-(2-chlorophenyl)-2-hydrazino-7-iodo-2H-thieno[2,3-e][4,1]diazepine was combined with 375 ml of ethyl acetate, 170 ml of triethyl orthoacetate and a few crystals of para-toluenesulfonic acid and the mixture was heated on the steam bath for 30 minutes. The product crystallized during this process and was collected after cooling. Recrystallization from methylene chloride/ethanol gave colorless crystals of the title compound with m.p. 254°–256°. The starting material was preparted as described in Example 126.

EXAMPLE 126

5-(2-Chlorophenyl)-1,3-dihVdro-7-iodo-2H-thieno[2,3-e][1,4]diazepine-2-thione

A mixture of 70 g of 5-(2-Chlorophenyl)-1.3-dihydro-7-iodo-2M-thieno[2,3-e][1,4]diazepin-2-one, 43.3 g of phosphorus pentasulfide, 45 g of sodium bicarbonate and 700 ml of diglyme was stirred and heated (o 70°–80° for 2 hours. After cooling to room temperature, a mixture of water and crushed ice was added and stirring was continued for 15 minutes. The precipitated product was collected by filtration, washed with water and sucked dry. This material was used directly in example 126. The starting material used was synthesized as shown in Example 127.

EXAMPLE 127

5-(2-Chlorophenyl)-1,3-dihydro-7-iodo-2H-thieno[2,3-e][1,4]diazepin-2-one.

A solution of 54.8 g of 5-(2-chlorophenyl)-1,3-dihydro-2H-thieno[2,3-e][4,1]diazepin-2-one [NL patent 7,205,730, Nov. 1972, Hoffmann-La Roche & Co., AG, Basle]in 350 ml of acetic acid and 350 ml of methanol was treated with 64.4 g of iodine monochloride and 16.2 g of sodium acetate. The mixture was stirred for 15 minutes at room temperature. A solution of 65 g of sodium bisulfite in 350 ml of water was then added and stirring was continued for 10 minutes. The mixture was neutralized by addition of 500 ml of conc. ammonia and 1 kg of ice. The precipitated product was filtered off and washed with water and ethanol. Recrystallization from tetrahydrofuran/ ethanol gave off-white crystals of the title compound with m.p. 229°–231°.

EXAMPLE 128

4-(2-Chlorophenyl)-2-iodo-9-methvl-6H-thieno[3.2-f!1.2 4]triazol o[4,3-a][1,4]diazepine-5-oxide.

Meta-chloroperoxybenzoic acid 3.4 g, was added to a solution of 4.4g of 4-(2-chlorophenyl)-2-iodo-9-methyl6H-thieno[3,2-f][1,2,4]triazolo[4,3-a][4,1]diazepine in 200 ml of methylene chloride. After sitting at room temperature in the dark for 18 hours. it was washed with 10% aqueous sodium carbonate solution. The orqanic phase was dried over sodium sulfate, filtered and evaporated. The residue was crystallized from tetrahydrofuran/methanol/ethyl acetate to give 3.3g of crude product. It was purified by passing over a plug of silica gel using 10% (v/v) of methanol in methylene chloride. the eluate was evaporated and the residue was crystallized from tetrahydrofuran/methanol to give off-white crystals of the title compound with m.p. 280°–283° with decomposition.

EXAMPLE 129 rac-6-Acetyloxy-4-(2-chlorophenyl)-2-iodo-9-methvl-6H-thieno[3,2-f][1,2,4]triazolo[4,3-a][1,4]diazeoine.

A mixture of 1g of 4-(2-chlorophenyl)-2-iodo-9-methyl6H-thieno[3,2-f][1,2,4]triazolo[4,3-a][4,1]diazepine-5-oxide 25 ml of pyridine and 15 ml of acetic anhydride was heated on the steam bath for 4 hours. The reagents were evaporated under reduced pressure, at the end azeotropically with xylene. The residue was chromatographed over 25g of silica gel using 5% (v/v) of ethanol in methylene chloride for elution. The combined clean fractions were evaporated and the product was crystallized from ethyl acetate and recrystallized from tetrahydrofuran/methanol/ethyl acetate to give colorless crystals of the title compound with m.p. 248°–250°.

EXAMPLE 130

Rac-4-(2-chlorophenyl)-2-iodo-9-methyl-6H-tbieno3.2-f][1 2,4]traizolo[4,3-a][1,4]diazepine-6-ol.

Sodium hydroxide, 1 ml 3-N, and lo ml of water was added to a solution of 0.3 g of rac-6-acetyloxy-4-(2-chlorophenyl)-2-iodo-9-methyl-6H-thieno[3,2-f][1,2,4]triazolo[4,3-a][4,1]diaz in 30 ml of methanol. After standing at room temperature for 30 minutes, the solution was acidified with acetic acid and partitioned between methylene chloride and aqueous sodium bicarbonate solution. The organic phase was separated, dried

EXAMPLE 131

1-{3-[6-(4-Chlorophenyl)-1-methyl-4H-[1,2,4]triazolo[4,3-a][1,4]benzodiazepin-8-yl]-2-propynyl-3.4-dihydro-2(1H)quinolinone.

This compound was prepared by coupling 6-(4-chlorophenyl)8-iodo-1-methyl-4H-[1,2,4]triazolo[4,3-a][4,1]benzodiazepine with 3,4-dihydro-1-(2-propynyl)-2(1H)-quinolinone under the conditions used in Example 37. The product was isolated by chromatography over the 50-fold amount of silica gel using 20% (v/v) of hexane in tetrahydrofuran for elution. Crystallization of the combined clean fractions from ethyl acetate and recrystallization from the same solvent gave colorless crystals of the title compound with m.p. 215°–217°. These crystals contained 0.33 molar amounts of water according to the analytical data. The starting material used in this experiment was prepared as described in example 132.

EXAMPLE 132

6-(4-Chlorophenyl)-8-iodo-1-methyl-4H-1,2,4]triazolo[4,3-a][1,4 benzodiazepine.

A mixture of 2.8 g of 5-(4-chlorophenyl)-2-hydrazino-7-iodo-3H-4,1-benzodiazepine, 40 ml of xylene and 10 ml of triethyl orthoacetate was heated to reflux for 1.5 hours. The crystals which separated from the cooled reaction mixture were filtered off and recrystallized from tetrahydrofuran/ethanol to give colorless crystals of title compound with m.p. 358°–360°. The hydrazino compound required was obtained as described in Example 13.3

EXAMPLE 133

5-(4-Chlorophenyl]-2-hydrazino-7-iodo-3H-1 4-benzodiazepine.

A mixture of 4g of 5-(4-chlorophenyl)-1,3-dihydro-7-iodo2H-4,1-benzodiazepine-2-thione, 50 ml of tetrahydrofuran, 20 ml of 2-propanol and 1.5 ml of hydrazine was stirred at room temperature for 30 minutes. This mixture was filtered over a plug of 10 g of silica gel using tetrahydrofuran for elution. The filtrate was evaporated and the residue was crystallized from ether. Recrystallization of this material from tetrahydrofuran-/ethanol gave colorless crystals of the title compound with m.p. 250°–252°. The required thione was prepared as shown in example 134.

EXAMPLE 134

5-(4-Chlorophenyl)-1,3-dihydro-7-iodo-2H-1,4-benzodiazepine-2thione.

A mixture of 12g of 5-(4-chlorophenyl)-1,3-dihydro-7-iodo-2H-1,4-benzodiazepin-2-one, 8 g of phosphorus pantasulfide, 8g of sodium bicarbonate and 100 ml of diglyme was stirred and heated to 80°–85° for 3 hours. Water and crushed ice was added after cooling and stirring was continued for 10 minutes. The precipitated product was collected by filtration and washed with water, 2-propanol and ether. For analysis it was recrystallized from tetrahydrofuran/ethanol to yield the title compound and melted at 260°–262°. The starting material was prepared as described in example 135.

EXAMPLE 135

5-(4-Chlorophenyl)-1,3-dihydro-7-iodo-2H-1,4-benzodiazeoin-2-one.

Bromoacetyl bromide, 5 ml, was added to a solution of 18 g of (2-amino-5-iodophenyl)(4-chlorophenyl)methanone on 250 ml of methylene chloride stirred with crushed ice for 15 minutes. The organic layer was separated,m washed with sodium bicarbonate solution, dried and evaporated. The residue was crystallized from methylene chloride/ether to give 18 g of bromoacetyl derivative. This material was dissolved in 200 ml of methylene chloride and added to 300 ml of liquid ammonia. The ammonia was allowed to gradually evaporate over night and the remaining methylene chloride was washed with water, dried and evaporated. The residue was dissolved in 300 ml of ethanol and heated to reflux for 30 minutes after the addition of 10 ml of acetic acid. The solvent was partially evaporated and the product was crystallized by cooling. Recrystallization from methylene chloride/ethanol gave colorless crystals of the title compound with m.p. 246°–248°. The required aminobenzophenone was prepared as described in Example 136.

EXAMPLE 136

(2-Amino-5-iodoohenyl)(4-chlorophenvl)methanone

A solution of 23 g of (2-aminophenyl)(4-chlorophenyl)methanone in 500 ml of methylene chloride was cooled to −50°. Iodine monochloride, 21 g or 15 ml, was added and the mixture was stirred in the cold for 4 hours. It was then allowed to warm to 0° and was quenched with a solution of sodium bisulfite in water. After stirring for 10 minutes, the organic layer was separated, dried and evaporated. The title compound was crystallized form toluene/hexane to give yellow crystals with m.p. 137°–139°.

EXAMPLE 137

1-{3-[6-(4-Chlorophenyl)-1-trifluoromethyl-4H-[1,2,4]triazolo-[4,3-a]1,4]benzodiazeDin-8-yl]-2-propynyl-3.4-dihydro-2(1H)-quinolinone.

This oompound was obtained by ooupIing 6-(4-ohIorophenyl)-1-trifluoromethyl-8-iodo-4H-[1,2,4]triazolo[4,3-a][4,1]benzodiazepine with 3,4-dihydro-1-(2-propynyl)-2(1H)-quinolinone under the conditions used in Example 37, but extending the reaction time to 48 hours. The product was isolated by chromatography over the 50-fold amount of silica gel using methylene chloride: ethyl acetate 1:1. The clean fraction containing the product were combined and evaporated and the residue was crystallized from ethyl acetate/hexane to give off-white crystals of the title compound with m.p. 220°–222°. These crystals contained 0.5 molar amounts of water according to analytical data. The starting material was prepared as shown in example 138.

EXAMPLE 138

6-(4-Chlorophenyl)-1-trifluoromethyl-8-iodo-4H-[1,2,4]triazolo[4,3-a][1,4]benzodiazeoine.

A mixture of 3.4g of 5-(4-chlorophenyl)-2-hydrazino-7-iodo-3H-4,1-benzodiazepine from example 133, 75 ml of methylene chloride. 5 ml of trifluoroacetic anhydride and 15 ml of trifluoroacetic acid was heated under nitrogen on the steam bath to remove the methylene chloride and evaporated. The residue was crystallized from methanol/ ethyl acetate to give colorless crystals of the title compound with m.p. 240°–243° dec.

within ca 30 minutes. Toluene, 100 ml, was then added and heating on the steam bath was continued for 30 minutes. the cooled mixture was washed with saturated sodium bicarbonate solution, was dried and evaporated. The residue was chromatographed over 200 g of silica gel using 10% (v/v) of ethyl acetate in methylene chloride for elution. The fractions containing the product were combined and evaporated. Crystallization from ethyl acetate gave colorless crystals of the title compound with m.p. 243°–245°.

EXAMPLE 139

Rac-5-{3-[4-(2-Chlorophenyl)-6,9-dimethvl-6H-thieno[3,2-f][1,2,4]triazolo[4,3-a)[4,1]diazepin-2-yl]-2-propynyl]-6(5H)phenanthridinone.

This compound was prepared by reacting rac-4-(2-chloro-phenyl)-2-iodo-6,9-dimethyl-6H-thieno-[3,2-f][1,2,4]triazolo[4,3a][4,1]diazepine (from example 108) with 5-(2-propynyl)-6(5H) phenanthridinone under the conditions described in example 37. The product was isolated by chromatography over the 50 -fold amount of silica gel using 5% (v/v) of ethanol in methylene chloride. The product was crystallized from ethanol to give yellowish crystals of the title compound with mp, 182°–186° with foaming. These crystals contained according to analytical data molar amounts of water.

EXAMPLE 140

4-(2-Chlorophenyl)-2-[(1-naphthyl)ethynyl]-9-methyl-6H-thieno[3,2-f][1,2,4]triazolo4,3-a][1,4]diazeoine.

A mixture of 0.34 g of 4-(2-chlorophenyl)-2-ethynyl-9-methyl-6H-thieno[3,2-f][1,2,4]triazolo[4,3-a][1,4]diazepine, 45 mg of triphenylphosphine, 10 mg of cuprous iodide, 1 ml of triethylamine, 0.38 g of 1-iodonaphthalene and 10 ml of dimethylformamide was degased for 10 minutes by a slow stream of argon. After addition of 15 mg of palladium acetate the mixture was stirred under argon for 2 hours at room temperature. The reaction mixture was poured into saturated sodium bicarbonate solution and ice. The precipitate was filtered off, washed with water and dissolved in methylene chloride. The solution was dried and evaporated and the residue was chromatographed over 15 g of silica gel using 25% (v/v) of hexane in tetrahydrofuran. The combined clean factions containing the product were evaporated and the residue was crystallized from ethyl acetate/hexane to give off-white crystals of the title compound with m.p. 197°–199°.

Example 141

| Suspension (oral) | |
|---|---|
| 2-[3-[4-(2-chlorophenyl)-9-methyl 6H-thieno[3,2-f][1,24]-triazolo [4,3-a][1,4]diazepin-2-yl]-2-propynyl]-1H-benz[de]isoquinoline-1,3(2H)-dione (microfine)(Compound A) | 5.0 gm |
| Hydroxypropylmethyl cellulose | 8.0 gm |
| Polysorbate 80 | 0.5 gm |
| Distilled Water q.s. and | 100.0 mL |

Procedure

1. Add Compound A (o a solution of polysorbate 80 and disperse.
2. In distilled water make a solution of hydroxypropylmethyl cellulose.
3. Mix the materials from step 1 and 2, then add distilled water to bring to 100 mL.

EXAMPLE 142

| Capsule Formulation | |
|---|---|
| | mg/capsule |
| 2-[3-[4-(2-chlorophenyl)-9-methyl 6H-thieno[3,2-f][1,2,4]-triazolo [4,3-a][1,4]diazepin-2-yl]-2-propynyl]-1H-benz[de]isoquinoline-1,3(2H)-dione (microfine)(Compound A) | 50.00 |
| Polyvinylpyrrolidone K-90 | 0.50 |
| Polysorbate 80 | 0.25 |
| Microcrystalline Cellulose | 99.00 |
| Distilled Water | q.s. |
| Magnesium Stearate | 0.25 |
| Total Weight | 150.00 mg |

Procedure

1. To Compound A add a sufficient amount of an aqueous solution of polyvinylpyrrolidone K-90 and polysorbate 80.
2. Granulate to consistency, dry and screen through a 40 mesh sieve.
3. Add the microcrystalline cellulose and Magnesium Stearate, then blend.

EXAMPLE 143

| Tablet Formulation | |
|---|---|
| | mg/tablet |
| 2-[3-[4-(2-chlorophenyl)-9-methyl 6H-thieno[3,2-f][1,2,4]-triazolo [4,3-a][1,4]diazepin-2-yl]-2-propynyl]-1H-benz[de]isoquinoline-1,3(2H)-dione (microfine)(Compound A) | 50.00 |
| Polyvinylpyrrolidone (fine) | 14.25 |
| Polyvinylpyrrolidone K-90 | 0.50 |
| Microcrystalline Cellulose | 35.00 |
| Sodium Starch Glycolate | 10.00 |
| Distilled Water | q.s. |
| Magnesium Stearate | 0.25 |
| Total Weight | 110.00 |

Procedure 1. prepare a blend of Compound A, sodium starch glycolate, and polyvinylpyrrolidone, then add a sufficient amount of an aqueous solution of polyvinylpyrrolidone K 90.
2. Granulate to consistency, dry and screen trough a 40 mesh sieve.
3. Add microcrystalline cellulose and magnesium stearate, then blend.

EXAMPLE 144

| Aerosol Suspension, 0.5 mg/actuation | |
|---|---|
| 2-[3-[4-(2-chlorophenyl)-9-methyl 6H-thieno[3,2-f][1,2,4]-triazolo [4,3-a][1,4]diazepin-2-yl]-2-propynyl]-1H-benz[de]isoquinoline-1,3(2H)-dione (microfine)(Compound A) | 120.00 mg |
| Sorbitan trioleate | 40.0 mg |
| Trichloromonofluoro methane | 1.80 mL |
| Dichlorodifluoro methane | 10.20 mL |

Procedure

1. To Compound A add a solution of Sorbitan Triolcate and trichloromonofluoro methane.
2. Homogenize and add the suspension to an aluminum container.
3. Crimp a 50 microliter metering valve to the container and pressure fill the dichlorodifluoro methane.

EXAMPLE 145

| Topical Solution 1% | |
|---|---|
| 2-[3-[4-(2-chlorophenyl)-9-methyl 6H-thieno[3,2-f][1,2,4]-triazolo [4,3-a][1,4]diazepin-2-yl]-2-propynyl]-1H-benz[de]isoquinoline-1,3(2H)-dione (microfine)(Compound A) | 1.0 gm |
| Polyethylene glycol 400 | 99.0 gm |

Procedure

1. Add Compound A to the polyethyleneglycol 400 and mix well until dissolved.

I claim:

1. A compound of formula

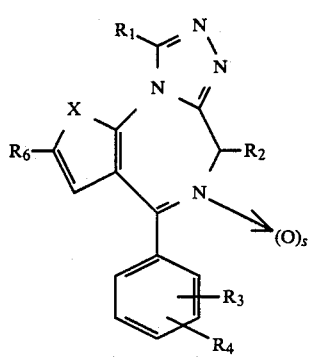

I wherein X is —CH=CH— or S;
  $R_1$ is lower alkyl, lower alkoxy or trifluoromethyl;
  $R_2$ is hydrogen, lower alkyl, lower alkoxy, hydroxy or acetyloxy;
  $R_3$ and $R_4$, independently, are hydrogen, chlorine, fluorine, lower alkyl or lower alkoxy;
  s is an integer from 0 to 1, provided that when s is 1, $R_2$ cannot be hydroxy, lower alkoxy or acetyloxy;
  $R_5$ is a radical of the formula
  $R_7$—O—$(CH_2)_m$—C≡C— wherein $R_6$ and $R_7$ are naphthyl, phenyl or phenyl or naphthyl mono-, di-, or trisubstituted by chlorine, fluorine, lower alkoxy or lower alkoxy or a heterocyclic radical selected from the group consisting of pyridinyl, imidazolinyl, thienyl, furyl, pyrimidinyl, oxazolinyl,

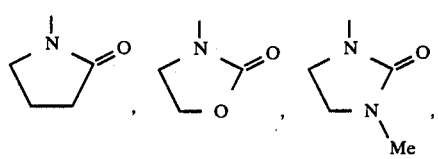

-continued

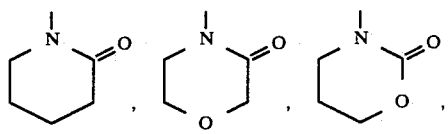

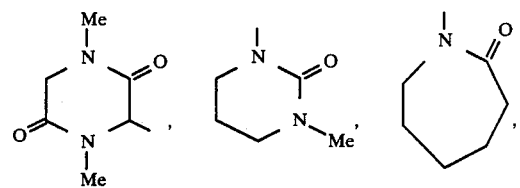

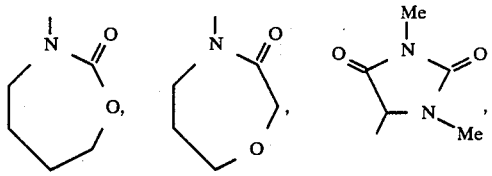

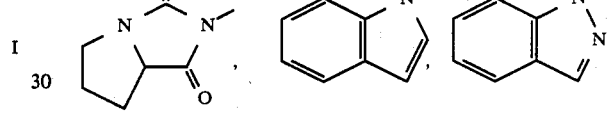

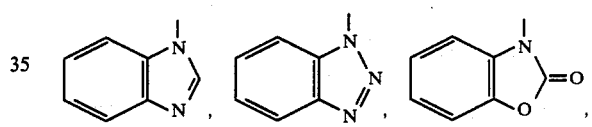

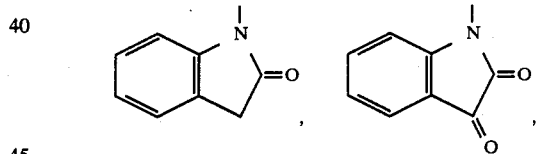

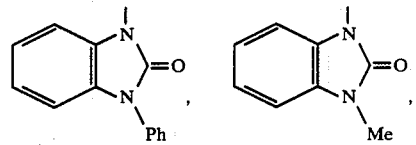

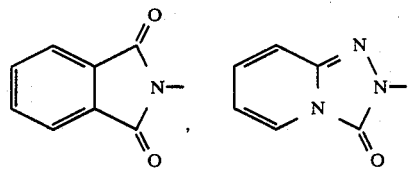

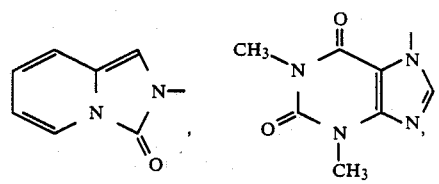

-continued
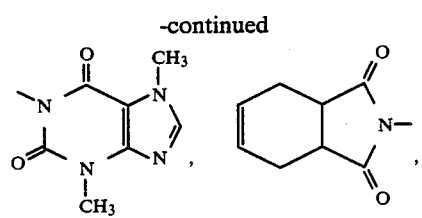
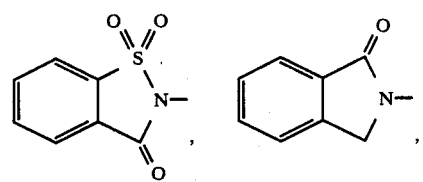
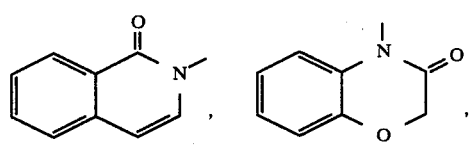
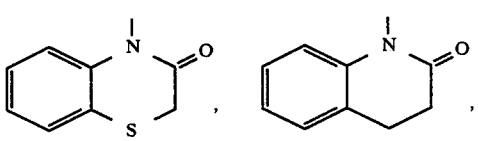
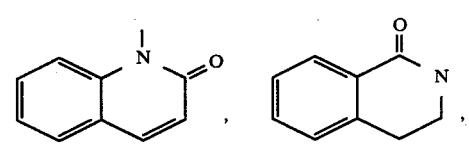
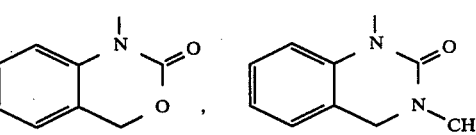
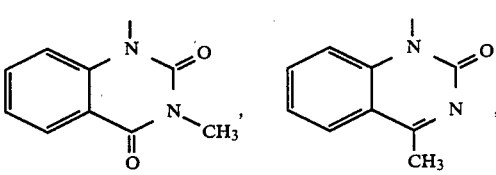
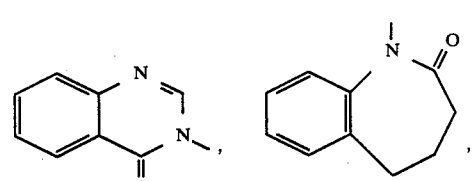
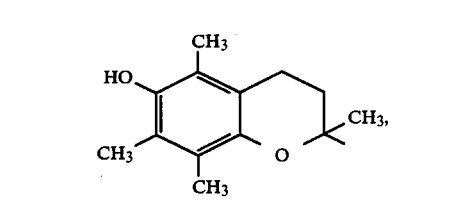
-continued
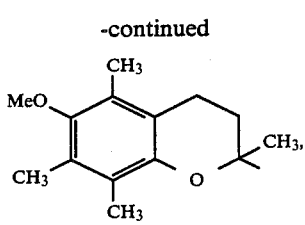
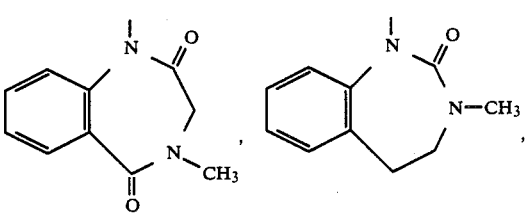
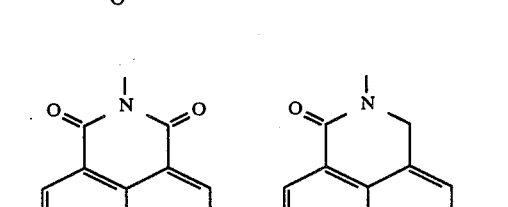
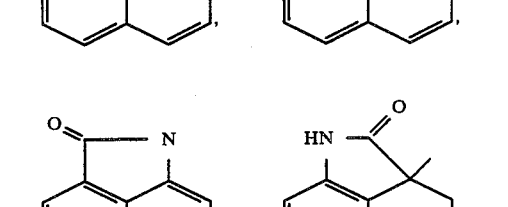
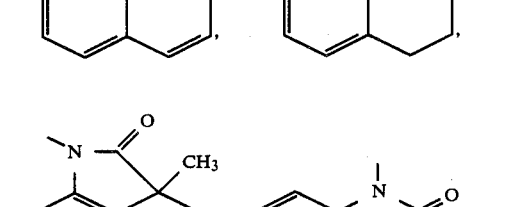
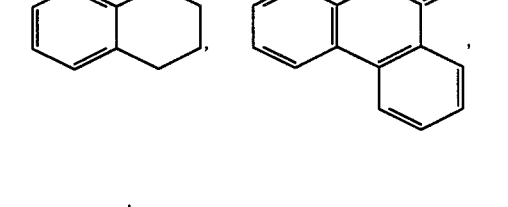
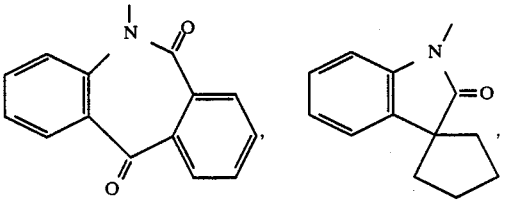
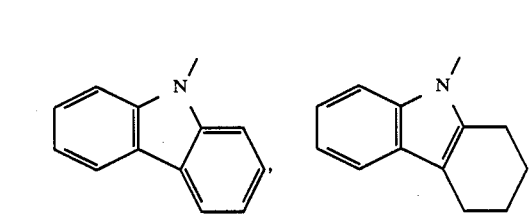

-continued

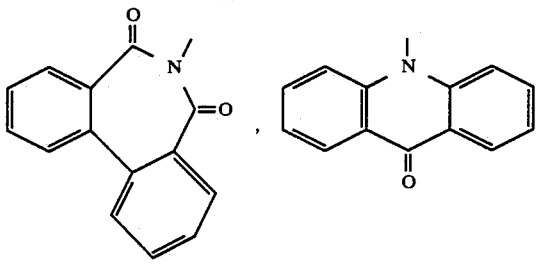

which can be substitutents selected from the group consisting of lower alkyl, lower alkoxy, chlorine and fluorine, n is an integer of from 0 to 2 and m is an integer of from 1 to 2, provided that, when n is 0 $R_6$ must be attached through a carbon to carbon bond, and provided that $R_7$ is always attached through a carbon to oxygen bond, or, when at least one asymmetric carbon is present, an enantiomer or racemate thereof, or a pharmaceutically acceptable acid addition salt thereof.

2. A compound in accordance with claim 1. wherein s is 0.

3. A compound, in accordance with claim 1, wherein s is 1.

4. A compound, in accordance with claim 2, wherein X is

5. A compound, in accordance with claim 2, wherein X is S.

6. A compound, in accordance with claim 4, wherein $R_5$ is $R_6-(CH_2)_n-C\equiv C-$.

7. A compound, in accordance with claim 4, wherein $R_5$ is $R_7-O-(CH_2)_m-C\equiv C-$.

8. A compound, in accordance with claim 5, wherein $R_5$ is $R_6-(CH_2)_n-C\equiv C-$.

9. A compound, in accordance with claim 5, wherein $R_5$ is $R_7-O-(CH_2)_m-C\equiv C-$.

10. A compound, in accordance with claim 8, wherein $R_6$ is a heterocyclic radical.

11. A compound, in accordance with claim 9, wherein $R_7$ is

12. A compound, in accordance with claim 10, wherein $R_1$, is methyl or ethyl, R2 is hydrogen, R is fluorine or chlorine, $R_4$ is hydrogen, s is 0 and n is 1 or 2.

13. A compound, in accordance with claim 10, wherein $R_1$ is methyl, $R_2$ is hydrogen, R is fluorine or chlorine at the 2-position of the phenyl moiety. $R_4$ is hydrogen. s is 0, n is 1 and $R_6$ is hetero-bicyclic or hetero-tricyclic group.

14. A compound, in accordance with claim 10, wherein $R_1$ is methyl, $R_2$ is hydrogen, $R_3$ is chlorine and at the 2-position of the phenyl moiety, $R_4$ is hydrogen, n is 1 and $R_6$ is selected from the group consisting of

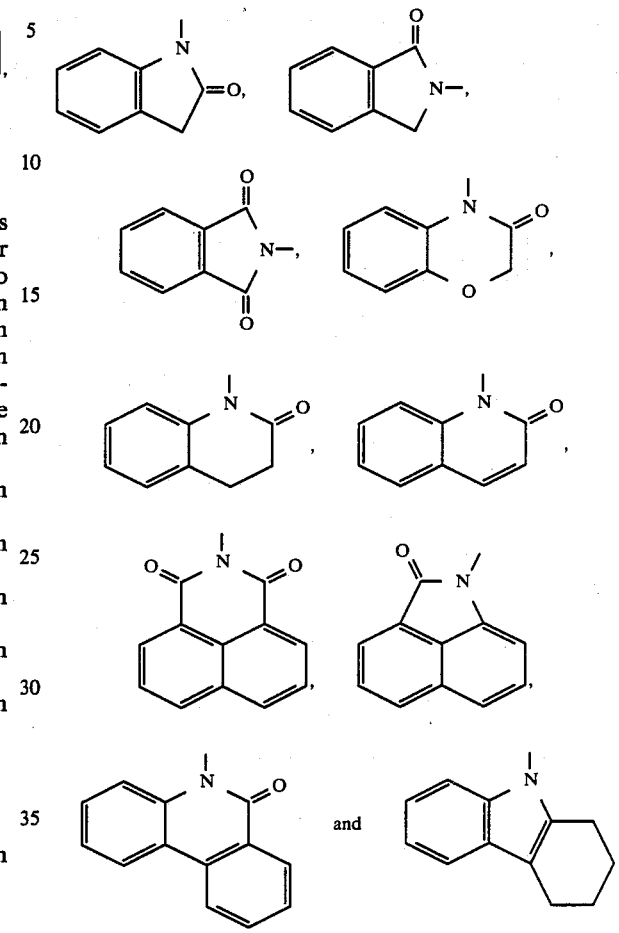

which can be substituted by one or two substituents selected from the group consisting of lower alkyl, lower alkoxy, chlorine and fluorine.

15. A compound, in accordance with claim 11, wherein $R_1$ is methyl or ethyl. $R_2$ is hydrogen, $R_3$ is fluorine or chlorine and $R_4$ is hydrogen.

16. A compound, in accordance with claim 11, wherein $R_1$ is methyl, $R_2$ is hydrogen, $R_3$ is fluorine or chlorine at the 2-position of the phenyl moiety, $R_4$ is hydrogen, m is and $R_7$ is phenyl, naphthyl or phenyl or naphthyl mono-, di- or trisubstituted by chlorine, fluorine, lower alkyl or lower alkoxy.

17. A compound, in accordance with claim 9, wherein $R_1$ is methyl, R2 is hydrogen, $R_3$ is chlorine and at the 2-position of the phenyl moiety, $R_4$ is hydrogen, n is 1 and $R_7$ is phenyl, naphthyl or pyridyl.

18. A compound, in accordance with claim 1, 1-[3-[4-(2-Chlorophenyl)-9-methyl-6H-thieno[3.2-f][1,2,4][4,3-a][4,1]diazepin-2-yl]-2-propynyl]-benz[cd]-indol-2(1H)-one.

19. A compound, in accordance with claim 1, 5-{3-[4-(2-chlorophenyl)-9-methyl-6H-thieno[3,2-f][1,2,4]triazol 4,3-a][4,1]diazepin-2-yl]-2-propynyl}-phenanthridin-6(5H)-one.

20. A compound, in accordance with claim 1, 4-(2-chlorophenyl)-2-[3-(1,2.3,4-tetrahydro-9H-carbazol-9-yl)1-propynyl]-9-methyl-6H-thi(®)no-[3,2-f]1,2,4]triazolo[4,3-a][1,4]diazepine.

21. A compound, in accordance with claim 1, 1-{3-[4-(2-chlorophenyl)-9-methyl-6H-thieno[3,2-f][1,2,4]triazolo[4,3-a][1,4]diazepin-2-yl]-2-propynyl}-3,4-dihydro2(1H)-quinolinone.

22. A compound, in accordance with claim 1, 4-[3-[4-(2-Chlorophenyl)-9-methyl-6H-thieno[3,2-f][1,2,4]triazolo[4,3-a][4,1]diazepin-2-yl]-2-propynyl]-2H-4,1-benzoxazin-3(4H)-one.

23. A compound, in accordance with claim 1, 1-[3-[4-(2-Chlorophenyl)-9-methyl-6H-thieno[3,2-f][1,2,4]triazolo[4,3-a][4,1]diazepin-2-yl]-2-propynyl]-1H-indole2,3-dione.

24. A compound in accordance with claim 1 1-[3-[4-(2-Chlorophenyl)-9-methyl-6H-thieno[3,2-f][1,2,4]triazolo[4,3-a][4,1]diazepin-2-yl]-2-propynyl].1,3-dihydro 2H-indol-2-one.

25. A compound, in accordance with claim 1. 2-[3-[4-(2-Chlorophenyl)-9-methyl-6H-thieno[3,2-f][1,2,4]triazolo[4,3-a][4,1]diazepin-2-yl]-2-propynyl]-1,2,4triazolo[4,3-a]pyridin-3(2H)-one.

26. A compound, in accordance with claim 1, 2-[3-[4-(2-Chlorophenyl)-9-methyl-6H-thieno[3,2-f][1,2,4]triazolo[4,3-a][4,1]diazepin-2-yl]-2-propynyl]-1,2-benziso-thiazol-3(2H)-one 1,1-dioxide.

27. A compound, in accordance with claim 1, 4-(2-Chlorophenyl)-2-[3-(1H-indazol-1-yl)-1-propynyl]-9-methyl-6H-thieno[3,2-f][1,2,4]triazolo[4,3-a][4,1]diazepine.

28. A compound, in accordance with claim 1, 2-[3-(1H-Benzimidazol-1-yl)-1-propynyl]-4-(2-chlorophenyl)-9-methyl-6H-thieno[3,2-f][1,2,4]triazolo[4,3-a][1,4]diazepine.

29. A compound, in accordance with claim 1, 2-[3-[6-(2-Fluorophenyl)-1-methyl-4H-[1,2 4]triazolo [4,3-a][4,1]benzodiazepin-8-yl]-2-propynyl]-1H-isoindole-1,3(2H)-dione.

30. A compound, in accordance with claim 1, 4-[3-[6-(2-Fluorophenyl)-1-methyl-4H-[1,2,4]triazolo [4,3-a][4,1]benzodiazepin-8-yl]-2-propynyl]-2H-4,1-benzoxazin-3(4H)-one.

31. A compound, in accordance with claim 1, 4-(2-chlorophenyl)-9-methyl-2-[3-(3-pyridyloxy-1-propynyl)-6H. thieno[3,2-f][1,2,4]triazolo[4,3-a][4,1]diazepine.

32. A pharmaceutical composition comprising an effective amount of a compound of formula

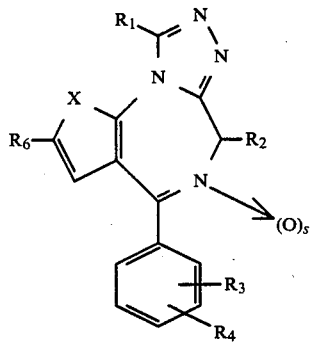

wherein X is —CH=CH— or S;

R₁ is lower alkyl, lower alkoxy or trifluoromethyl;
R₂ is hydrogen, lower alkyl, lower alkoxy, hydroxy or acetyloxy;
R₃ and R₄, independently, are hydrogen, chlorine, fluorine, lower alkyl or lower alkoxy;

s is an integer from 0 to 1, provided that when s is 1, R₂ cannot be hydroxy, lower alkoxy or acetyloxy;
R₅ is a radical of the formula
R₆—(CH₂)ₙ—C≡C— or R₇—O—(CH₂)ₘ—C≡C—
wherein R₆ and R₇ are naphthyl, phenyl or phenyl or naphthyl mono-, di- or trisubstituted by chlorine, fluorine, lower alkyl or lower alkoxy or a heterocyclic radical selected from the group consisting of pyridinyl, imidazolinyl, thienyl, furyl, pyrimidinyl, oxazolinyl,

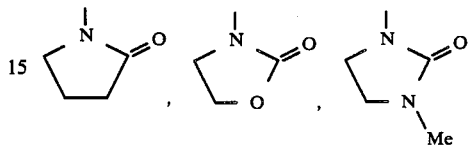

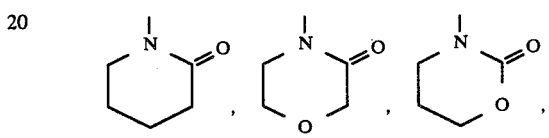

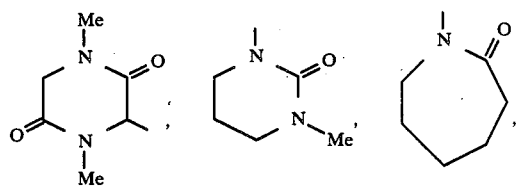

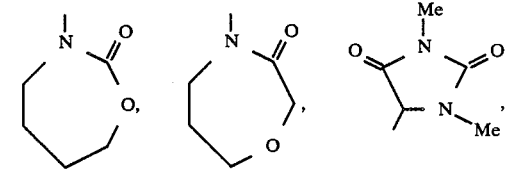

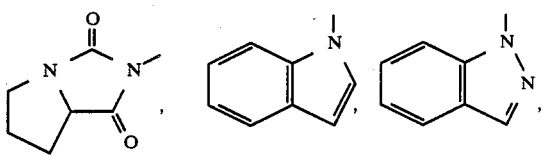

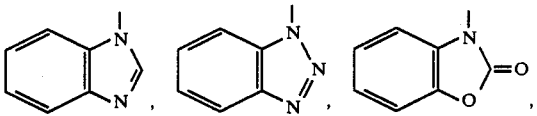

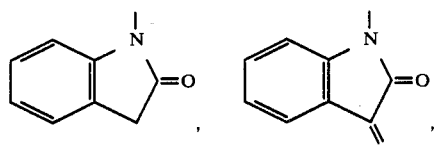

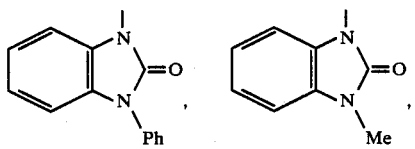

-continued
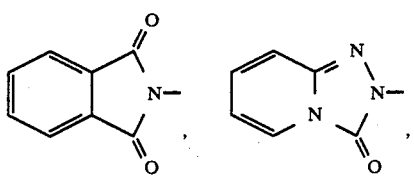
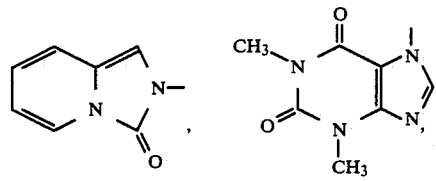
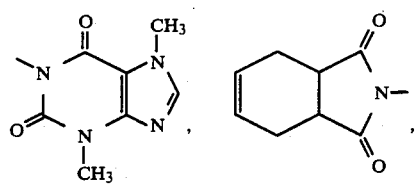
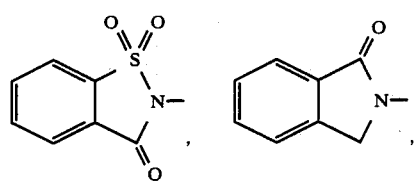
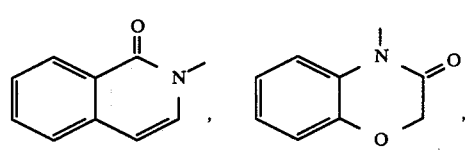
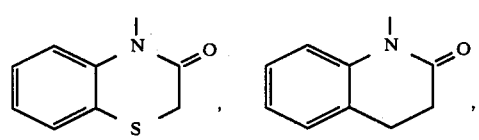
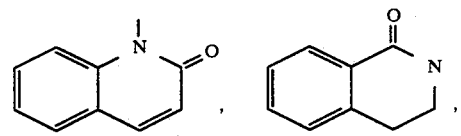
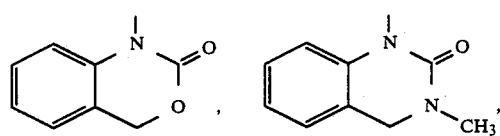
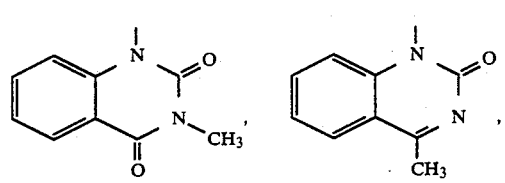
-continued
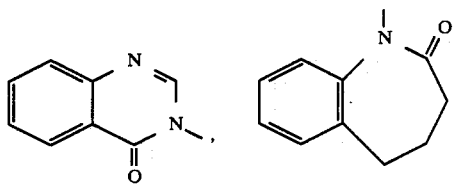
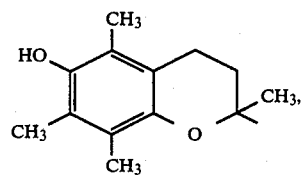
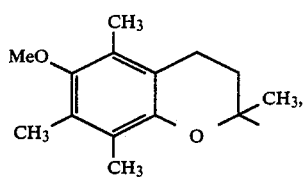
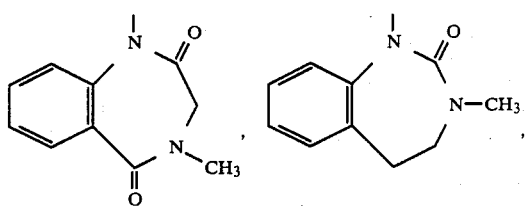
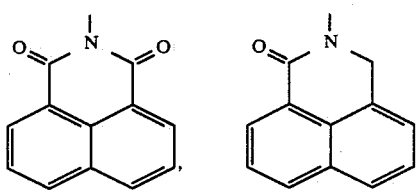
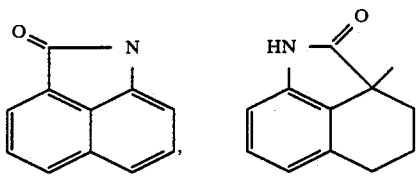
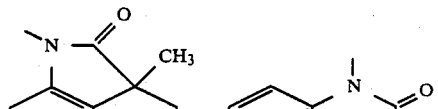
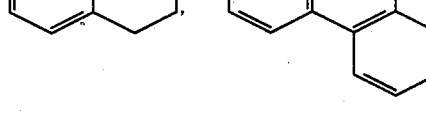
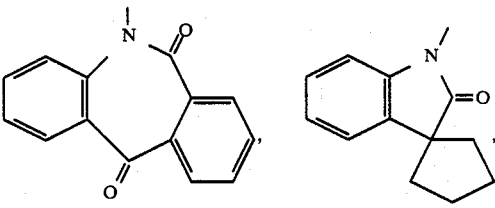

-continued

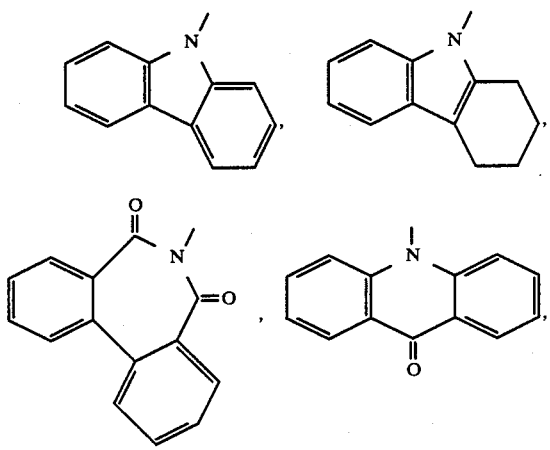

which can be substituted by one or two substituents selected from the group consisting of lower alkyl, lowr alkoxy, chlorine and fluorine, n is an integer of from 0 to 2 and m is an integer of from 1 to 2, provided that, when n is 0, R6 must be attached through a carbon to carbon bond, and provided that R7 is always attached through a carbon to oxygen bond, or, when at least one asymmetric carbon is present, an enantiomer or racemate thereof, or a pharmaceutically acceptable acid addition salt thereof, and an inert carrier material.

33. A pharmaceutical composition, in accordance wirh claim 32, wherein s is 0.

34. A pharmaceutical composition, in accordance with claim 33, wherein s is 1.

35. A pharmaceutical composition, in accordance with claim 33, wherein X is —CH=CH—.

36. A pharmaceutical composition, in accordance with claim 34, wherein X is S.

37. A pharmaceutical composition, in accordance with claim 35, wherien R5 is

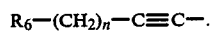
R6—(CH2)$_n$—C≡C—.

38. A pharmaceutical composition, in accordance with claim 35, wherein R5 ios

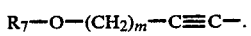
R7—O—(CH2)$_m$—C≡C—.

39. A pharmaceutical composition, in accordance with claim 36, wherein R5 is

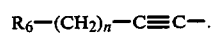
R6—(CH2)$_n$—C≡C—.

40. A pharmaceutical composition, in accordance with claim 36, wherein R5 is

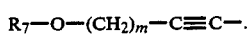
R7—O—(CH2)$_m$—C≡C—.

41. A pharmaceutical composition, in accordance with claim 32, wherein the compound of formula I is 2-[3-[4-(2-Chlorophenyl)-9-methyl-6H-thieno[3,2-f][1,2,4]triazolo[4,3-a][4,1]diazepin-2-yl]-2-propynyl]-1H-benz[de]isoquinoline-1,3(2H)-dione.

42. A pharmaceutical composition, in accordance with claim 32, wherein the compound of formula I is 1-[3-[4-(2-Chlorophenyl)-9-methyl-6H-thieno[3,2-f][1,2,4]triazolo[4,3-a][4,1]diazepin-2-yl]-2-propynyl]-benz[cd]indol-2(1H)-one.

43. A pharmaceutical composition, in accordance with claim 32, wherein the compound of formula I is 4-[3-[4-(2-Chlorophenyl)-9-methyl-6H-thieno[3,2-f][1,2,4]triazolo[4,3-a][4,1]diazepin-2-yl]-2-propynyl]-2H-1,4-benzoxazin-3(4H)-one.

44. A pharmaceutical composition, in accordance with claim 32, wherein the compound of formula I is 5-{3-[4-(2-chlorophenyl)-9-methyl-6H-thieno[3,2-f][1,2,4]triazolo[4,3-a][1,4]diazepin-2-yl]-2-propynyl]-phenanthridin-6(5H)-one.

45. A pharmaceutical composition, in accordance with claim 32, wherein the compound of formula 1 is 4-(2-chlorophenyl)-2-[3-(1,2,3,4-tetrahydro-9H-carbazol-9-yl)1-propynyl]-9-methyl-6H-thieno[3,2-f][1,2,4]-triazolo[4,3-a][4,1]diazepine.

46. A pharmaceutical composition, in accordance with claim 32, wherein the compound of formula I is 1-{3-[4-(2-chlorophenyl)-9-methyl-6H-thieno-[3,2-f][1,2,4]triazolo[4,3-a][4,1]diazepin-2-yl]-2-propynyl}-3,4-dihydro-2 (1H)-quinolinone.

47. A method which comprises administering to a host requiring a paltelet activating factor antagonist an effecting amount of a compound of the formula

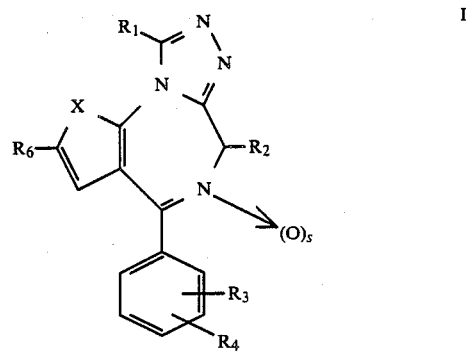

wherein X is —CH=CH— or S;
R1 is lower alkyl, lower alkoxy or trifuloromethyl;
R2 is hydrogen, lower alkyl, lower alkoxy, hydroxy or acetyloxy;
R3 and R4, independently, are hydrogen, chlorine, fluorine, lowr alkyl or lower alkoxy;
s is an integer from 0 to 1, provided that when s is 1, R2 cannot be hydroxy, lower alkoxy or acetyloxy;
R5 is a radical of the formula
R6—(CH2)$_n$—C≡C— or R7—O—(CH2)$_m$—C≡C— wherein R6 and R7 are naphthyl, phenyl or phenyl or naphthyl mono-, di- or trisubstituted by chlorine, fluorine, lower alkyl or lower alkoxy or a heterocyclic radical selected from the group consisting of pyridinyl, imidazolinyl, thienyl, furyl, pyrimidinyl, oxazolinyl,

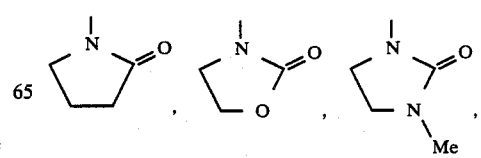

-continued
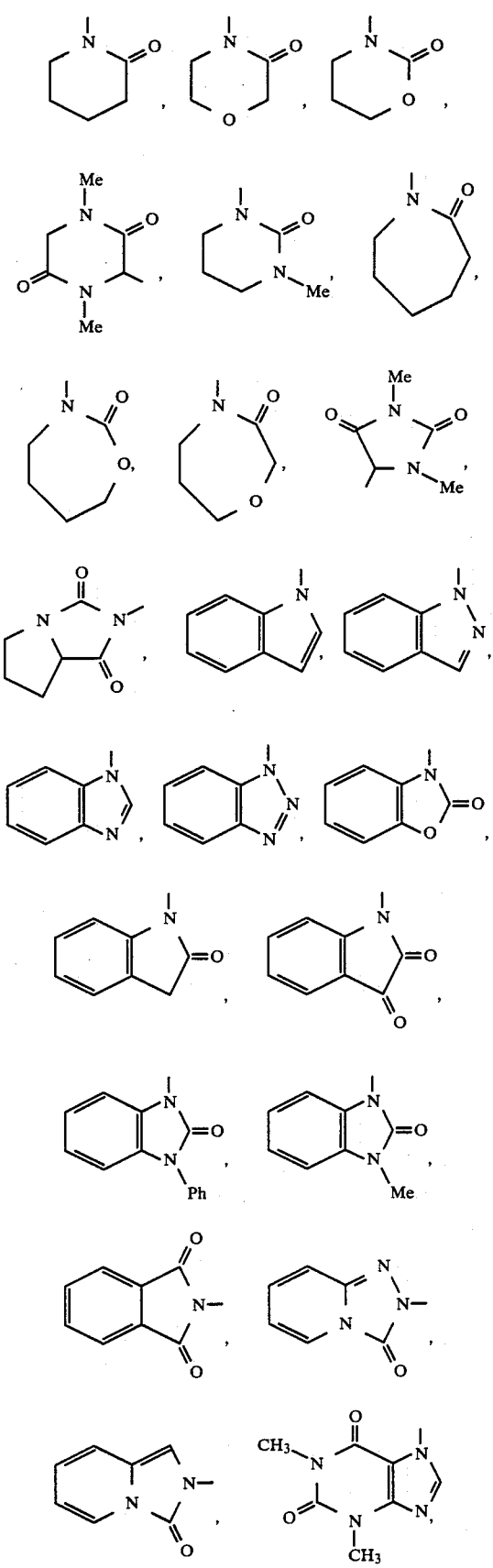
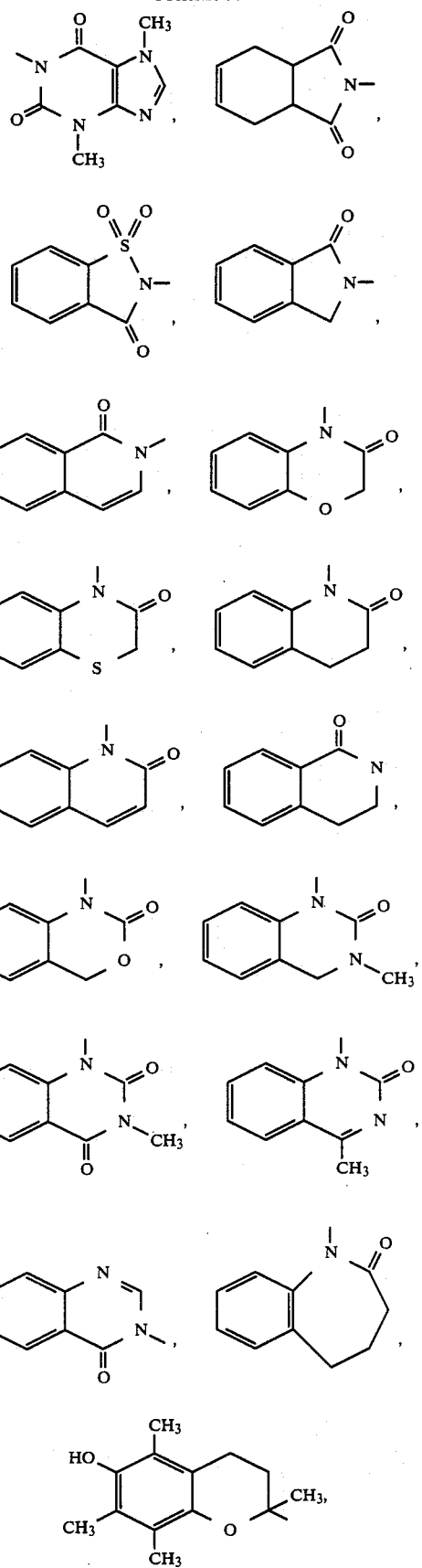

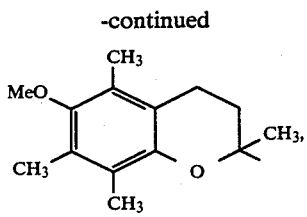

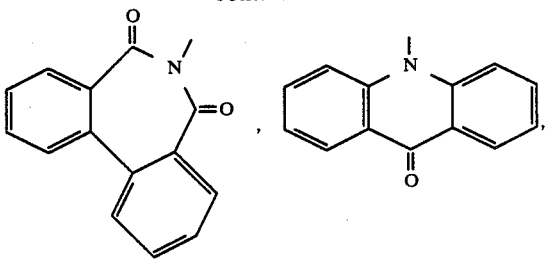

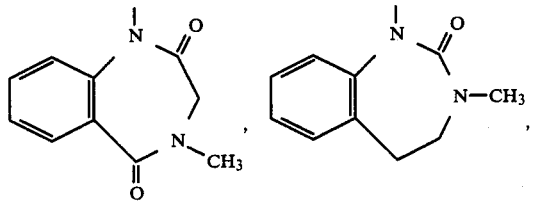

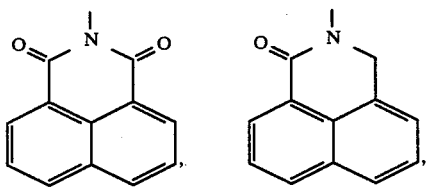

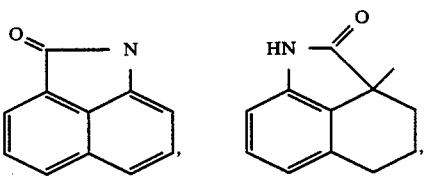

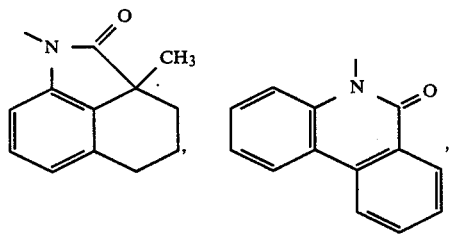

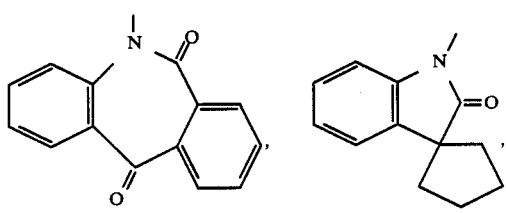

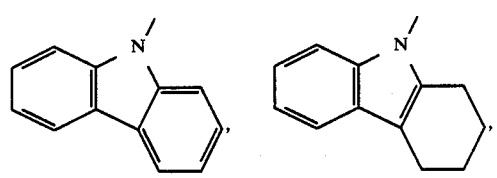

which can be substituted by one or two substituents selected from the group consisting of lower alkyl, lower alkoxy, chlorine and fluorine, n is an integer of from 0 to 2 and m is an integer of from 1 to 2, provided that, when n is 0, $R_6$ must be attached through a carbon to carbon bond, and provided that $R_7$ is always attached through a carbon to oxygen bond, or, when at least one asymmetric carbon is present, an enantiomer or racemate thereof, or a pharmaceutically acceptable acid addition salt thereof.

48. A method, in accordance with claim 47, wherein s is 0.

49. A method, in accordance with claim 47, wherein s is 1.

50. A method, in accordance with claim 48, wherein X is —CH=CH—.

51. A method, in accordance with claim 48, wherein X is S.

52. A method, in accordance with claim 50, wherein $$R_5 \text{ is } R_6-(CH_2)_n-C\equiv C-.$$

53. A method, in accordance with claim 50, wherein $$R_5 \text{ is } R_7-O-(CH_2)_m-C\equiv C-.$$

54. A method, in accordance with claim 51, wherein $$R_5 \text{ is } R_6-(CH_2)_n-C\equiv C-.$$

55. A method, in accordance with claim 51, wherein $$R_5 \text{ is } R_7-O-(CH_2)_m-C\equiv C-.$$

56. A method, in accordance with claim 47, wherein the compound of formula I is 2-[3-[4-(2-Chlorophenyl)-9-methyl6H-thieno[3,2-f][1,2,4]triazolo[4,3-a][1,4]diazepin-2-yl]-2propynyl]-1H-benz[de]isoquinoline-1,3(2H)-dione.

57. A method, in accordance with claim 47, wherein the compound of formula I is 1-[3-[4-(2-Chlorophenyl)-9-methyl-6H-thieno[3,2-f][1,2,4]triazolo[4,3-a][4,1]diazepin-2-yl]-2-proponyl]-benz[cd]indol-2(1H)-one.

58. A method, in accordance with claim 47, wherein the compound of formula I is 4-[3-[4-(2-Chlorophenyl)-9-methyl-6H-thieno[3,2-f][1,2,4]triazolo[4,3-a][4,1]diazepin-2-yl]-2-propynyl]-2H-4,1-benzoxazin-3(4H)-one.

59. A method, in accordance With claim 47, wherein the compound of formula I is 5-{3-[4-(2-chlorophenyl)-9-methyl-6H-thieno[3,2-f][1,2,4]triazolo[4,3-a][4,1]diazepin-2-yl]-2-propynyl}-phenanthridin-6(5H)-one.

60. A method, in accordance with claim 47, wherein the compound of formula I is wherein the compound of formula 1 is 4-(2-chlorophenyl)-2-[3-(1,2,3,4-tetrahydro-9H-carbazol-9-yl)-1-propynyl]-9-methyl-6H-thieno[3,2-f][1,2,4]triazolo[-triazolo -4,3-a][4,1]diazepine;

61. A method, in accordance with claim 47, wherein the compound of formula I is 1-{3-[4-(2-chlorophenyl)-9-methyl-6H-thieno-[3,2-f][1,2,4]triazolo[4,3-a][4,1]diazepin-2-yl]-2-propynyl}-3,4-dihydro-2(1H)-quinolone.

62. A compound in accordance with claim 1, 1-{3-[4-(b 2-chlorphenyl)-9-methyl-6H-thieno[3,2-f][1,2,4]-triazolo[4,3-a][1,4]diazepin-2-yl]-2-propynyl}-1,3-dihydro-3-methyl-2H-benzimidazo -2-one.

63. A compound in accordance with claim 1, 1{3-[4-(2-chlorphenyl)-9-methyl-6H-thieno[3,2-f][1,2,4]-triazolo triazolo [4,3-a][1,4]diazepin-2-yl]-2-propynyl}-1,3-dihydro-3-methyl-2,4(1H,3H)-quinzolinedione.

64. A compound in accordance with claim 1, 1-{3-[4-(b 2-chlorphenyl)-9-methyl-6H-thieno[3,2-f][1,2,4]-triazolo[4,3-a][1,4]diazepin-2-yl]-2-propynyl}-1,3-dihydro-3-phenyl-2H-benzimidazo 2-one.

* * * * *